United States Patent
Purandare et al.

(10) Patent No.: US 8,673,933 B2
(45) Date of Patent: *Mar. 18, 2014

(54) JAK2 INHIBITORS AND THEIR USE FOR THE TREATMENT OF MYELOPROLIFERATIVE DISEASES AND CANCER

(75) Inventors: Ashok V. Purandare, Pennington, NJ (US); James W. Grebinski, Lawrenceville, NJ (US); Amy C. Hart, Ewing, NJ (US); Jennifer Inghrim, Plainsboro, NJ (US); Gretchen M. Schroeder, Ewing, NJ (US); Honghe Wan, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,742

(22) Filed: Apr. 30, 2012

(65) Prior Publication Data

US 2013/0225551 A1  Aug. 29, 2013

Related U.S. Application Data

(63) Continuation of application No. 12/874,276, filed on Sep. 2, 2010, now Pat. No. 8,202,881.

(60) Provisional application No. 61/239,501, filed on Sep. 3, 2009.

(51) Int. Cl.
*A61K 31/437* (2006.01)
*C07D 487/14* (2006.01)

(52) U.S. Cl.
USPC .................. 514/290; 546/82; 546/85; 546/87

(58) Field of Classification Search
USPC .................. 514/290; 546/82, 85, 87
See application file for complete search history.

(56) References Cited

U.S. PATENT DOCUMENTS 5,532,261 A  7/1996  DiNinno et al.

FOREIGN PATENT DOCUMENTS

WO  WO 2006/122137  11/2006
WO  WO 2010/080474  7/2010

OTHER PUBLICATIONS

Freshney ( Culture of Animal Cells, A Manual of Basic Technique, Alan R. Liss, Inc., 1983.*
Dermer (Bio/Technology, 1994, 12:320.*
Anonymous, "Multiple Ascending Dose of BMS-911543"; Online: ClinicalTrials.gov, Identifier: NCT01236352 (2010).

* cited by examiner

*Primary Examiner* — Rita Desai
(74) *Attorney, Agent, or Firm* — Elliott Korsen

(57) ABSTRACT

The present invention provides compounds of formula I

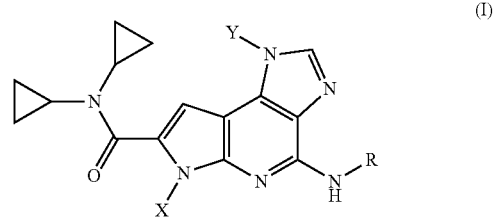

and pharmaceutically acceptable salts thereof. The formula I compounds inhibit tyrosine kinase activity of JAK2, thereby making them useful as antiproliferative agents for the treatment of cancer and other diseases.

3 Claims, 4 Drawing Sheets

Data for Example 26

In vivo data for Example 73

JAK2 INHIBITORS AND THEIR USE FOR THE TREATMENT OF MYELOPROLIFERATIVE DISEASES AND CANCER

RELATED APPLICATION

This application is a continuation of U.S. application Ser. No. 12/874,276 filed Sep. 2, 2010 now U.S. Pat. No. 8,202, 881, which claims the benefit of U.S. Provisional Application No. 61/239,501, filed Sep. 3, 2009, incorporated herein by reference in its entirety.

FIELD OF THE INVENTION

This invention relates to novel compounds that are useful as anti-cancer/antiproliferative agents. This invention also relates to a method of using the compounds in the treatment of proliferative diseases, such as cancer, and to pharmaceutical compositions containing the compounds.

BACKGROUND OF THE INVENTION

Efforts to identify new therapeutic approaches to Ph(−) myeloproliferative disease have been bolstered by the observations of constitutive activation of the JAK-Stat signaling pathway MPD patients. In particular, a single valine to phenyalanine mutation at residue 617 (JAK2-V617F) in JAK2 has been observed in the majority of PV (95%), ET (50-60%) and PMF (50-60%) patients (Table 2, Kralovics et al., 2005; Baxter et al., 2005; Tefferi et al., 2005). The V617F mutation resides in the region of the JAK2 gene encoding the pseudokinase domain which is thought to function as an autoinhibitory domain to regulate JAK2 tyrosine kinase activity. Mutations in exon 12 of JAK2 which also result in constitutive JAK2 kinase activity are also observed with a lesser frequency (<5% in PV and ET) and are mutually exclusive with JAK2V617F lesions (Pardanari et al., 2007; Scott et al., 2007). JAK2 is a member of a non-receptor tyrosine kinase family that also includes JAK1, Tyk2 and JAK3 and function as mediators of cytokine receptor signaling (for review see Murray, 2007). Upon cytokine binding to its cognate receptor, receptor-bound JAK family members are activated and phosphorylate a STAT, a latent transcription factor, which upon JAK-mediated phosphorylation undergoes dimerization and translocation to the nucleus to regulate gene expression. Genetic and biochemical studies have established distinct combinations of engagement of a JAK family member with an individual cytokine receptor. For instance, erythropoietin (EPO), thrombopoietin (TPO) and granuolocyte colony stimulating factor (GM-CSF) receptor engagement results in the predominant activation of JAK2 to mediate downstream signaling. Consistent with the pathophysiology of MPD associated with the JAK2-V617F mutation, these cytokines promote the differentiation and expansion of the cell types underlying PV, ET and PMF, respectively. Unlike other genetic activation events, expression of JAK2-V617F is not sufficient to promote transformation in cell based model systems and has been shown to require the co-expression of the type I cytokine receptors, highlighting an important functional co-dependence of the JAK-cytokine receptor interaction (Lu et al., 2005). Interestingly, activating mutations in the TPO receptor (MPL, tryptophan to leucine substitution at residue 515) have been identified in MPD patients afflicted with JAK2-V617F negative PMF and ET (5% and 1%, respectively) resulting in constitutive JAK2-Stat activation (Pikman et al., 2006). These observations indicate that JAK-Stat signal transduction can be activated through mutation in MPD at multiple points in the pathway in a mutually exclusive manner and suggest the possible presence of additional pathway mutations in JAK2-V617F and MPL-W515L negative MPD.

Important validation of JAK2 signaling as a driver of Ph(−) MPD emerged from rodent models where JAK2-V617F mutant signaling was reconstituted in the hematopoietic stem cell compartment. Several laboratories demonstrated that viral transduction of JAK2-V617F into mouse bone marrow and subsequent re-implantation into recipient mice reconstituted several aspects human MPD (Wernig et al. 2006, Lacout et al., 2006, Bumm et al., 2006, Zaeleskas et al., 2006). These features included elevated hematocrit, splenomegaly from extramedullary hematopoiesis, granulocytosis and bone marrow fibrosis all which are also manifested in polycythemia vera. Interestingly, unlike the human condition, thrombocytosis was not observed in these murine models and was suggested to be attributable to secondary genetic events that contribute to platelet expansion (Wernig et al., 2006). Similar reconstitution of the TPO receptor mutation (MPL-W515L) in rodent bone marrow resulted in a myeloproliferative disease with a more rapid onset than JAK2-V617F animals that was reminiscent of primary myelofribosis including splenomegaly, hepatomegaly, and reticulin fibrosis of bone marrow (Pikman et al., 2006). Also unlike the JAK2-V617F model, mice expressing MPL-W515L displayed dramatic thrombocytosis perhaps indicating a more dominant function of the receptor activation compared to JAK2-V617 in the expansion of this lineage. Nonetheless, these observations collectively underscore the role of both MPL-W515L and JAK2-V617F as driver mutations underlying the progression of human MPD.

A key question to the genetic basis of MPD is the role of additional genetic events that contribute to disease progression beyond JAK2 and MPL. Several lines of evidence suggest additional genetic alterations in MPD disease progression. In fact, mitotic recombination occurs frequently in MPD patients to generate two JAK2-V617F alleles indicating a selection for cell clones homozygous for the mutated kinase (Levine et al., 2005). In this regard it will be important to develop conditional JAK2-V617F knock-in animals and to determine the phenotypic consequences of the homozygous versus heterozygous JAK2-V617F burden. Additionally, there is evidence for an inherited germline allele that precedes and predisposes patients to acquire JAK2-V617F (Goerttler et al., 2005; Levine et al., 2006) as well as loss of chromosomal region 20q in some MPD patients. Although MPD conversion AML is observed clinically at moderate levels and activating JAK chromosomal translocations are observed in leukemia, epidemiological data suggest that it is questionable that JAK2-V617F is a genetic driver in this context suggesting additional genetic alterations are required for full leukemic transformation (Theocharides et al., 2007). These observations notwithstanding, JAK2 inhibition with small molecule inhibitors is sufficient to modulate disease progression in pre-clinical animal models suggesting that JAK2 activation is sufficient for maintaining MPD (Paradani et al., 2007). It will be important to identify these additional genetic alterations and decipher how these genetic changes contribute to the disease progression of PV, ET and PMF in the context of JAK2-V617F and MPL-W515L. It will also be important to implement approaches to identify if other JAK2 pathway components are mutated in MPD patients not associated with the acquisition of JAK2-V617F, JAK2 exon12 or MPL-W515L mutations.

The patent publication WO2006/122137 discloses compounds which are useful as IKK inhibitors. Example No. A171 discloses the compound of the formula

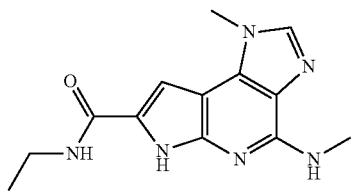 [SMILES: CCNC(=O)c1cc2c(nc(NC)c3ncn(C)c32)[nH]1]

which was found to have weak activity against JAK2 in the assay described hereinbelow.

BRIEF DESCRIPTION OF THE DRAWINGS

The invention is illustrated by reference to the accompanying drawings described below.

DETAILED DESCRIPTION OF THE INVENTION

Figure 1:
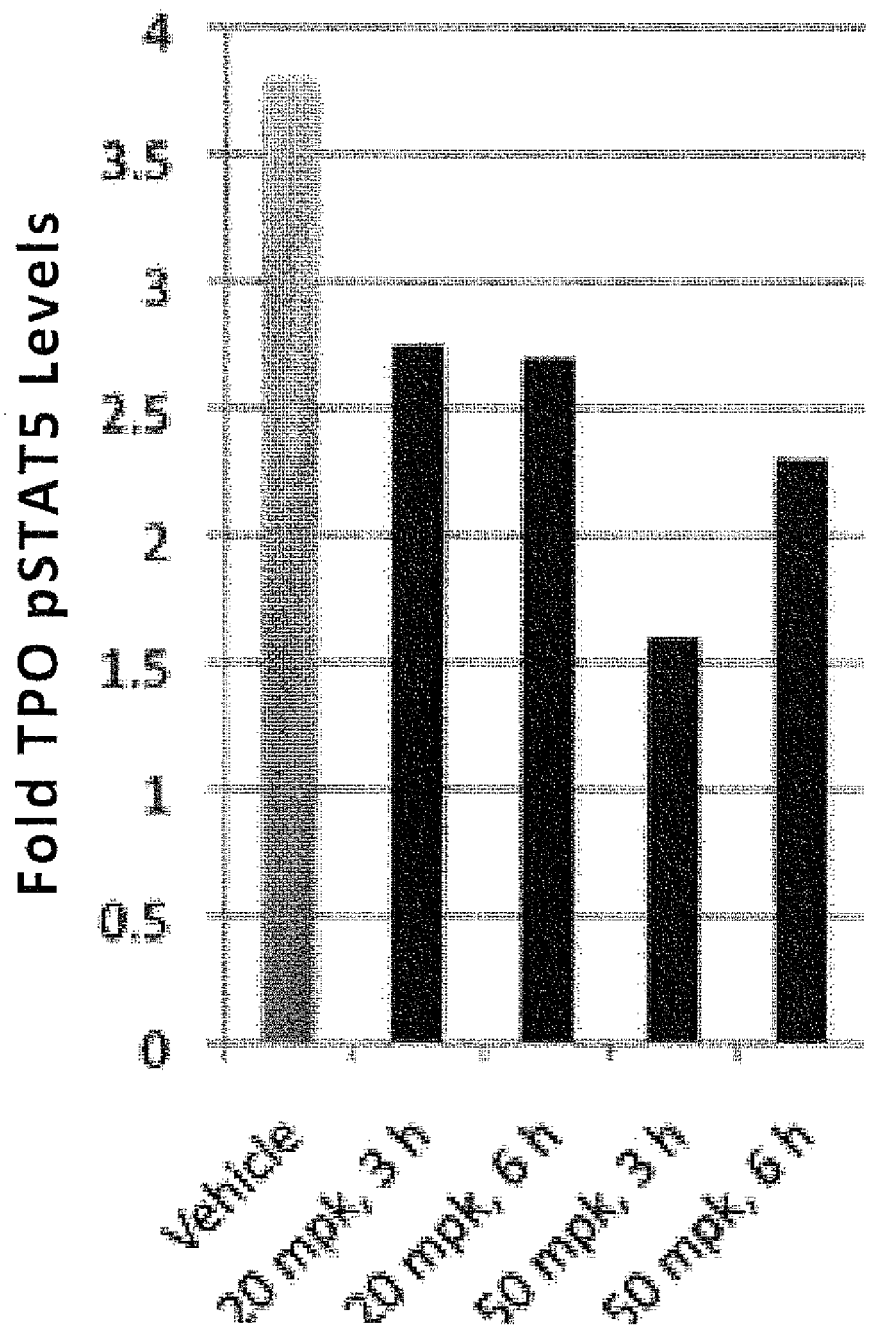
FIG. 1 shows in vivo data for the compound of Example 26.
Figure 2:
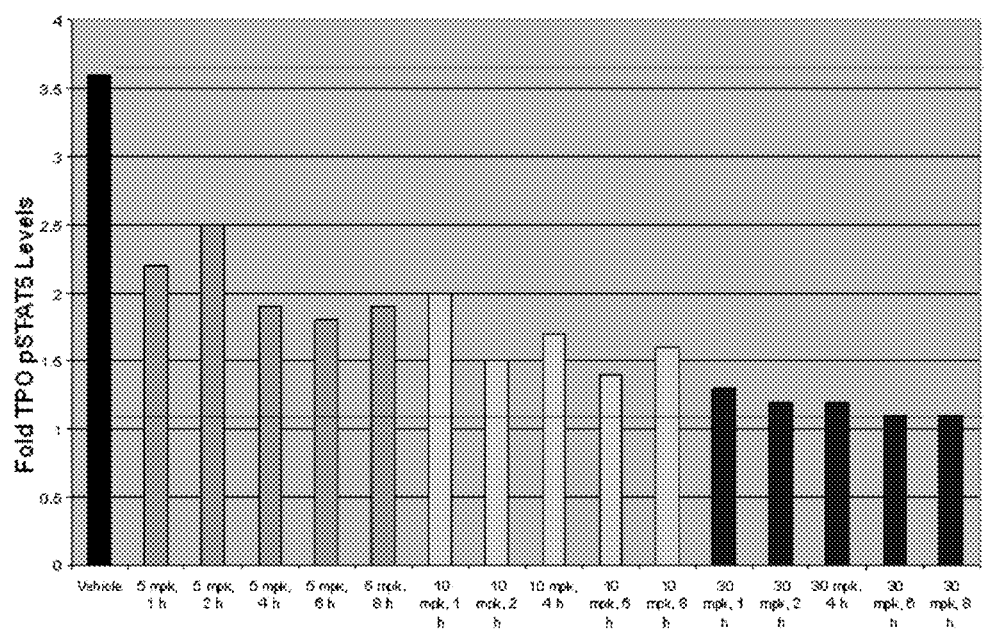
FIG. 2 shows in vivo data for the compound of Example 73.
Figure 3:
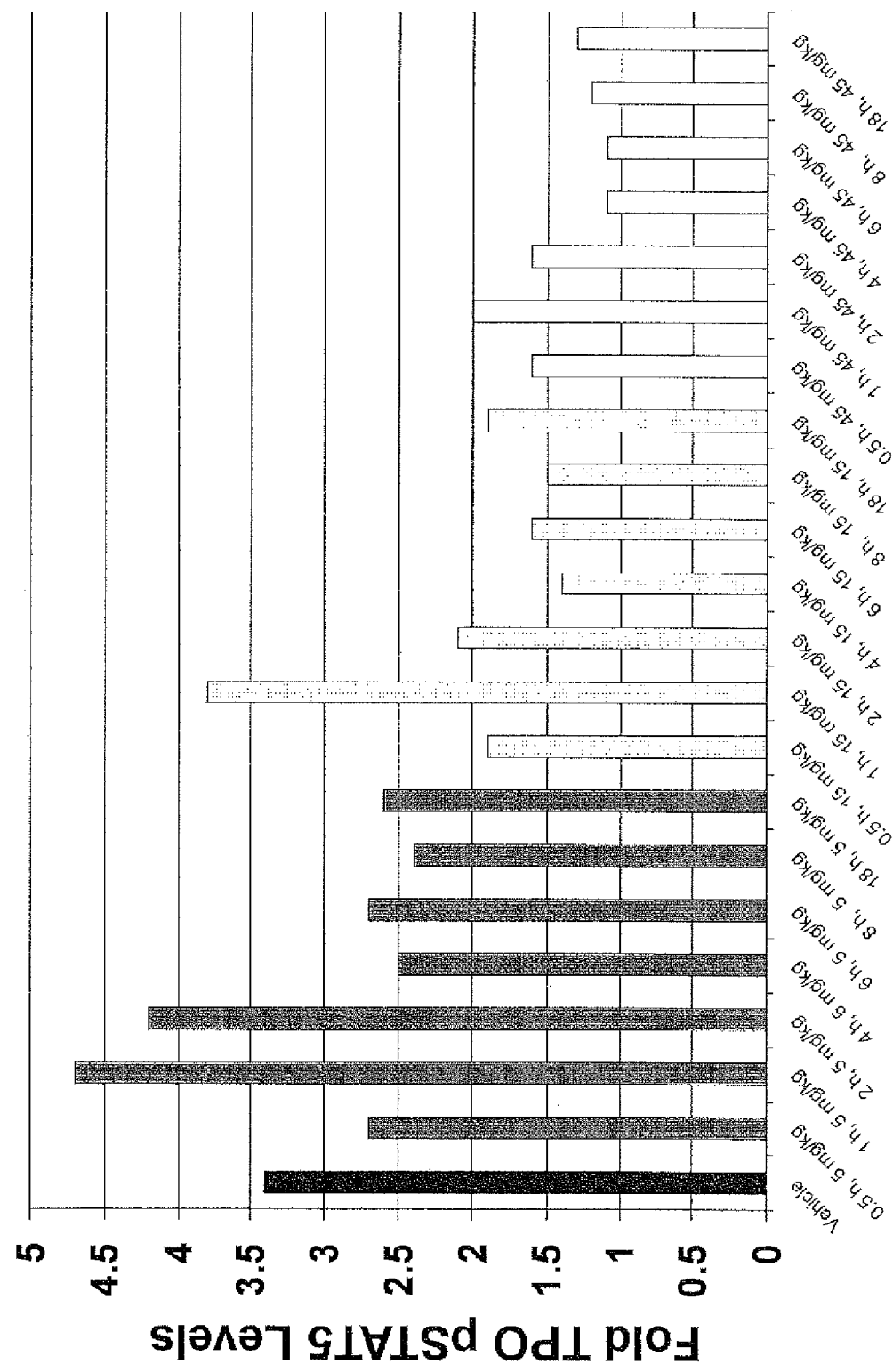
FIG. 3 shows in vivo data for the compound of Example 74.
Figure 4:
FIG. 4 shows in vivo data for the compound of Example 76.

The present invention provides for compounds of formula I, pharmaceutical compositions employing such compounds and for methods of using such compounds.
In accordance with the present invention, there are disclosed compounds of formula I

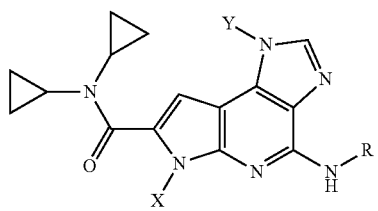

(I)

or a stereoisomer, tautomer, or pharmaceutically acceptable salt thereof, wherein:
Y is $C_{1-4}$ alkyl;
X is $C_{1-4}$ alkyl;
R is

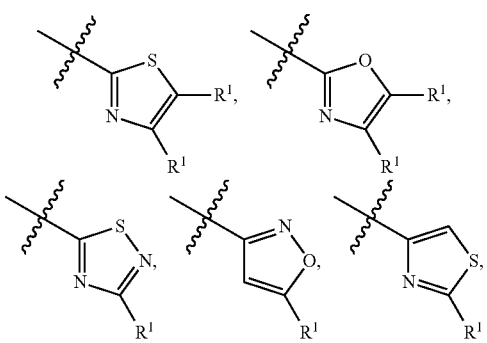

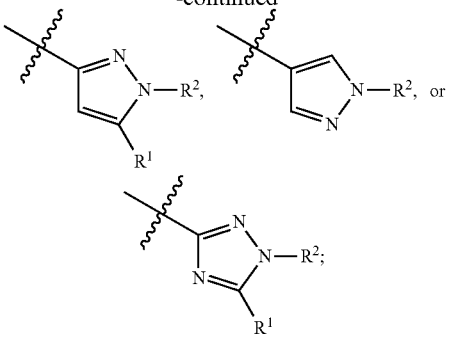

any of which are optionally fused with a 5 or 6 membered carbocycle or heterocycle having one heteroatom selected from $NR^3$ or S, said fused carbocycle or heterocycle being optionally substituted with 0-3 $R^1$.
$R^1$ is H, halo, CN, $C_{1-6}$ alkyl substituted with 0-3 $R^c$, $CF_3$, $CONR^aR^a$, $NR^aR^a$, $COOR^b$, $SO_2$—$C_{1-4}$alkyl, $C(O)R^d$, cycloalkyl substituted with 0-3 $R^e$, furanyl, tetrahydropyranyl, or pyridinyl;
$R^2$ is absent, H, $C_{1-6}$ alkyl substituted with 0-3 $R^c$, $C(O)$O—$C_{1-4}$alkyl, $SO_2$—$C_{1-4}$alkyl, cycloalkyl substituted with 0-3 $R^e$, or tetrahydropyranyl;
$R^3$ is absent, H, or $C(O)$O—$C_{1-4}$alkyl;
$R^a$ is H, $C_{1-6}$ alkyl substituted with 0-3 $R^e$, $C_{3-6}$ cycloalkyl substituted with 0-3 $R^e$, tetrahydropyranyl, or dioxotetrahydrothiophenyl;
$R^b$ is H or $C_{1-6}$ alkyl;
$R^c$ is H, halo, CN, OH, O—$C_{1-4}$alkyl, O—$C_{1-4}$alkyl-O—$C_{1-4}$alkyl, $NH_2$, $N(C_{1-4}$ alkyl$)_2$, $C(O)N(C_{1-4}$alkyl$)_2$, $SO_2$—$C_{1-4}$alkyl, or morpholinyl or piperazinyl, either of which are optionally substituted with 0-1 $C_{1-4}$alkyl;
$R^d$ is $C_{1-6}$ alkyl, or azeridinyl, azetidinyl, pyrrolidinyl, piperidinyl, morpholinyl, piperazinyl, dioxidothiomorpholinyl or tetrahydropyranyl, any of which are substituted with 0-2 $R^e$; and
$R^e$ is H, halo, CN, $C_{1-4}$ alkyl, OH, O—$C_{1-4}$alkyl, $SO_2$—$C_{1-4}$alkyl, NHC(O)—$C_{1-4}$alkyl, morpholinyl, OC(O)—$C_{1-4}$alkyl, $C(O)N(C_{1-4}$alkyl$)_2$, or O—$C_{1-4}$alkyl-O—$C_{1-4}$alkyl.
In another embodiment are compounds of Formula (I), wherein:
R is

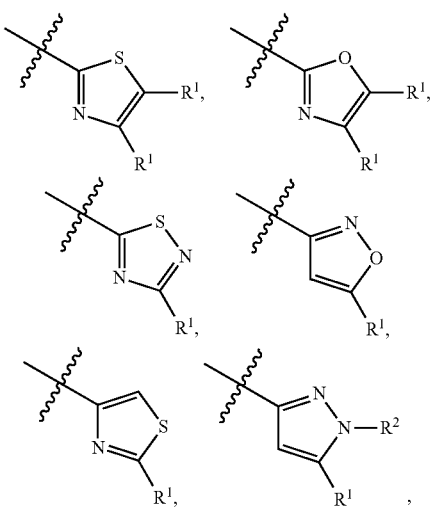

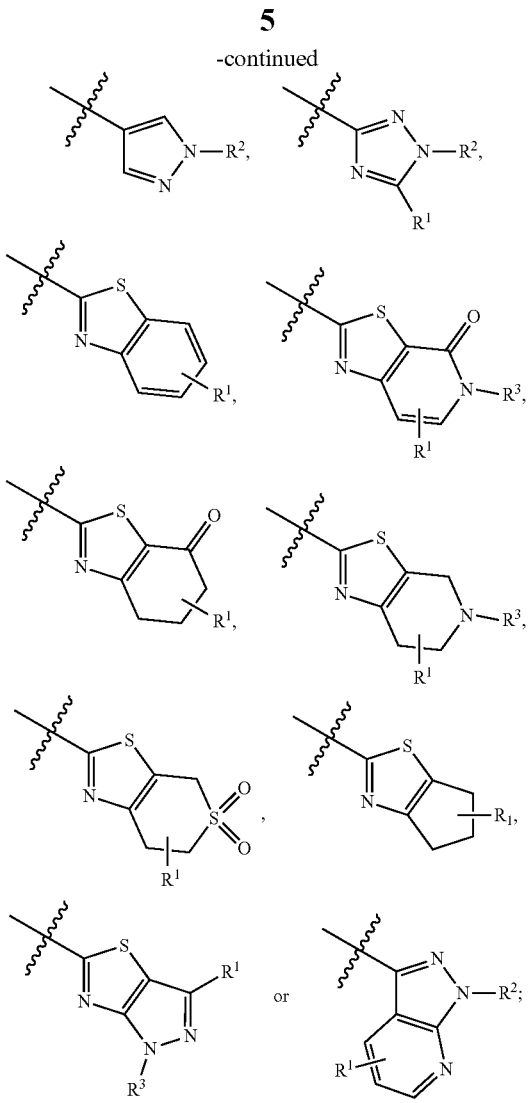

any of which are optionally substituted with 0-3 $R^1$.

In another embodiment are compounds of Formula (I), wherein:
Y is methyl; and
X is ethyl.

In another embodiment are compounds of Formula (I), wherein:
R is

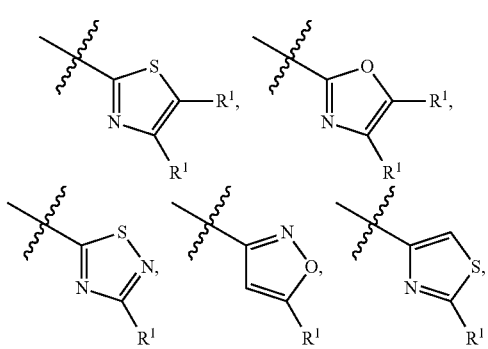

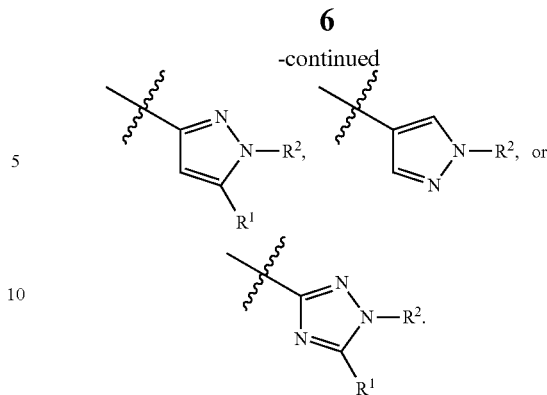

In another embodiment are compounds of Formula (I), wherein:
R is

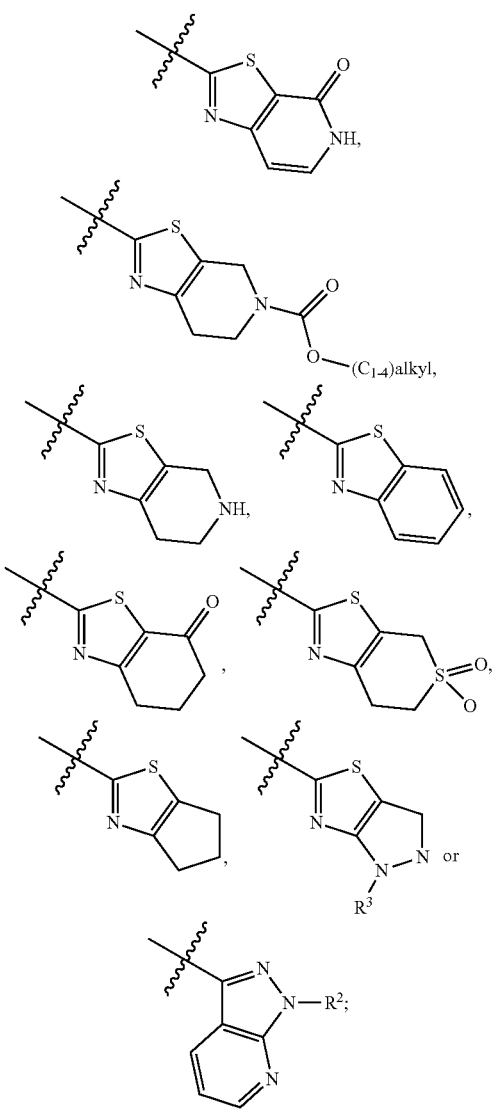

any of which are optionally substituted with 0-2 $R^1$

In another embodiment are compounds of Formula (I), wherein

R is

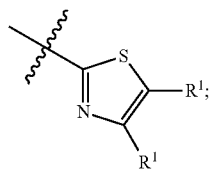

R[1] is H, halo, CN, $C_{1-6}$ alkyl substituted with 0-3 $R^c$, $CF_3$, $CONR^aR^a$, $COOR^b$, $SO_2$—$C_{1-4}$alkyl, $C(O)R^d$, cycloalkyl substituted with 0-3 $R^e$, or pyridinyl;

$R^a$ is H, $C_{1-6}$ alkyl substituted with 0-3 $R^e$, $C_{3-6}$ cycloalkyl substituted with 0-3 $R^e$, tetrahydropyranyl or dioxotetrahydrothiophenyl;

$R^b$ is H or $C_{1-6}$ alkyl;

$R^c$ is H, halo, OH, O—$C_{1-4}$alkyl, $SO_2$—$C_{1-4}$alkyl or morpholinyl;

$R^d$ is $C_{1-6}$ alkyl, or azetidinyl, pyrrolidinyl, morpholinyl, piperazinyl or dioxidothiomorpholinyl, any of which are substituted with 0-2 $R^e$;

$R^e$ is H, halo, CN, OH, O—$C_{1-4}$alkyl, $SO_2$—$C_{1-4}$alkyl, NHC(O)—$C_{1-4}$alkyl or morpholinyl.

In another embodiment are compounds of Formula (I), wherein:
R is

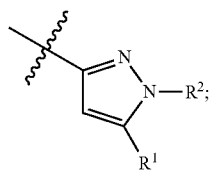

R[1] is H, halo, $C_{1-6}$ alkyl substituted with 0-3 $R^c$, $CF_3$, $CONR^aR^a$, $COOR^b$, $C(O)R^d$, cycloalkyl substituted with 0-3 $R^e$ or furanyl;

R[2] is H, $C_{1-6}$ alkyl substituted with 0-3 $R^c$, $SO_2$—$C_{1-4}$alkyl, cycloalkyl substituted with 0-3 $R^e$, or tetrahydropyranyl;

$R^a$ is H, or $C_{1-6}$ alkyl substituted with 0-3 $R^e$;

$R^b$ is H or $C_{1-6}$ alkyl;

$R^c$ is H, halo, CN, OH, O—$C_{1-4}$alkyl, O—$C_{1-4}$alkyl-O—$C_{1-4}$alkyl, $NH_2$, $N(C_{1-4}$ alkyl$)_2$, $C(O)N(C_{1-4}$alkyl$)_2$, $SO_2$—$C_{1-4}$alkyl, or morpholinyl or piperazinyl, either of which are optionally substituted with 0-1 $C_{1-4}$alkyl;

$R^d$ is $C_{1-6}$ alkyl, or morpholinyl, piperazinyl or dioxidothiomorpholinyl, any of which are substituted with 0-2 $R^e$; and $R^e$ is H, $C_{1-4}$ alkyl, CN, OH, NHC(O)—$C_{1-4}$alkyl or morpholinyl.

In another embodiment are compounds of Formula (I), wherein:
R is

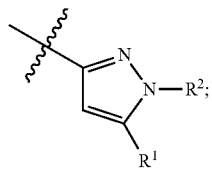

R[1] is $C_{1-6}$ alkyl substituted with 0-3 $R^c$; and
R[2] is $C_{1-6}$ alkyl.

In another embodiment are compounds of Formula (I), wherein the compound of formula (I) is selected from the exemplified compounds.

In another embodiment the present invention provides a pharmaceutical composition comprising a pharmaceutically acceptable carrier and one or more of the compounds of the present invention or a stereoisomer, tautomer, pharmaceutically acceptable salt, solvate, or prodrug thereof.

In another embodiment, the present invention provides a pharmaceutical composition comprising a compound of formula I or pharmaceutically acceptable salt thereof and a pharmaceutically acceptable carrier.

In another embodiment, the present invention provides a pharmaceutical composition, comprising a pharmaceutically acceptable carrier and a therapeutically effective amount of one or more of the compounds of the present invention or a stereoisomer, tautomer, pharmaceutically acceptable salt, solvate or prodrug thereof.

In another embodiment, the present invention provides a method for treating proliferative disorders and/or cancer comprising administering to a patient in need of such treatment a therapeutically effective amount of one or more of the compounds of the present invention or a stereoisomer, tautomer, pharmaceutically acceptable salt, solvate or prodrug thereof, in combination with one or more other anti-cancer agent, or a stereoisomer, tautomer, pharmaceutically acceptable salt, solvate or prodrug thereof.

In another embodiment, the present invention provides a method for treating proliferative disorders and/or cancer comprising administering to a patient in need of such treatment a therapeutically effective amount of one or more of the compounds of the present invention or a stereoisomer, tautomer, pharmaceutically acceptable salt, solvate or prodrug thereof.

In another embodiment, the present invention provides a method of treating a patient in need of proliferative disorder and/or cancer treatment, comprising administering a compound of the present invention or a stereoisomer, tautomer, pharmaceutically acceptable salt, solvate, or prodrug form thereof in an amount effective to treat the proliferative disorder and/or cancer.

In another embodiment, the present invention provides a method of treating myeloproliferative diseases, such as polycythemia vera, essential thrombocytopenia and primary myelofibrosis, solid tumors of the pancreas, prostate, lung, head and neck, breast, colon, ovary, gastric cancer as well as other tumor types including multiple myeloma, melanoma, neuroblastoma, glioblastoma, systemic mastocytosis, and hematological malignancies such as acute myelogenous leukemia (including refractory acute myeloid leukemia) and acute lymphoid leukemia.

In another embodiment, the present invention provides a novel method, comprising administering a compound of the present invention or a stereoisomer, tautomer, pharmaceutically acceptable salt, solvate, or prodrug form thereof in an amount effective to treat a proliferative disorder and/or cancer.

In another embodiment, the present invention provides a method for treating proliferative disorders and/or cancer comprising administering to a patient in need of such treatment a therapeutically effective amount of a compound of formula (I) or a stereoisomer, tautomer, pharmaceutically acceptable salt, solvate or prodrug thereof, in combination with one or more other anti-cancer agent or antiproliferative agent and/or another agent, or a stereoisomer, tautomer, pharmaceutically acceptable salt, solvate or prodrug thereof.

In another embodiment, the present invention provides a method for treating proliferative disorders and/or cancer comprising administering to a patient in need of such treatment a therapeutically effective amount of one or more of the compounds of the present invention or a stereoisomer, tautomer, pharmaceutically acceptable salt, solvate or prodrug thereof, in combination with one or more other anti-cancer agent, or a stereoisomer, tautomer, pharmaceutically acceptable salt, solvate or prodrug thereof.

In another embodiment, the present invention provides a compound of the present invention for use in therapy.

In another embodiment, the present invention provides a compound of the present invention for use in therapy for treating a proliferative disorder and/or cancer.

In another embodiment, the present invention also provides the use of a compound of formula I of the present invention for the manufacture of a medicament for the treatment of a proliferative disorder and/or cancer.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo.

The term "cycloalkyl" refers to cyclized alkyl groups, including mono-, bi- or poly-cyclic ring systems. $C_{3-10}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl Also included are smaller heterocycles, such as, epoxides and aziridines.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocycle" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocycle" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form (with no ionization) or may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include 13C and 14C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and Methods in Enzymology, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews,* 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that the presently recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

The present invention is based on the discovery that certain compounds are inhibitors of protein kinases. More specifically, compounds such as those described in this invention inhibit the protein tyrosine kinase activity of members of the JAK family of receptors, These inhibitors will be useful in the treatment of proliferative diseases that are dependent on signaling by one or more of these receptors. Such diseases include myeloproliferative diseases, solid tumors of the pancreatic, prostate, lung, head and neck, breast, colon, ovary, as well as other tumor types including multiple myeloma, melanoma, neuroblastoma, glioblastoma and hematological malignancies such as acute myelogenous leukemia.

The invention also relates to a pharmaceutical composition of compound of formula I, or pharmaceutically acceptable salt thereof, and a pharmaceutically acceptable carrier in the treatment of hyperproliferative disorder in mammal In particular, said pharmaceutical composition is expected to inhibit the growth and/or metastasis of those primary and recurrent solid tumors which are associated with Flt-3 (Fms-like kinase-3), JAK2, JAK3, and JAK1, especially those tumors which are significantly dependent on JAK2, for their growth and spread, including for example, cancers of the blood, thyroid, breast, colon, pancreas, or a variety of tumor types including multiple myeloma, melanoma, neuroblastoma and glioblastoma. In addition to JAK2 activity, inhibitory activity against JAK3/JAK1 or TYK2 may be useful in the treatment of certain cancers having an inflammatory component.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit Flt-3, JAK2, and JAK3, kinases, compounds of the present invention can be used for the treatment of proliferative diseases, including cancer.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

The present invention provides methods for the treatment of leukemia, myeloproliferative diseases such as polycythemia vera, essential thrombocytopenia and myelofibrosis, multiple myeloma, colon cancer, breast cancer, and gastric cancer.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; kinase inhibitors, e.g. Gleevec® and dasatinib (Sprycel®); Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyl-transferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia).

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Biological Assays
JAK2 Tyrosine Kinase Assay

The assays were performed in V-bottom 384-well plates. The final assay volume was 30 µL prepared from 15 µL additions of enzyme and substrates (fluoresceinated peptide and ATP) and test compounds in assay buffer (100 mM HEPES pH 7.4, 10 mM $MgCl_2$, 25 mM Beta-Glycerolphosphate, 0.015% Brij35 and 4 mM DTT). The reaction was initiated by the combination of JAK2 with substrates and test compounds. The reaction was incubated at room temperature for 60 min. and terminated by adding 45 µL of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 30 µM; JAK2 fluorescent peptide, 1.5 µM; JAK2, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis JAK3 Tyrosine Kinase Assay The assays were performed in V-bottom 384-well plates. The final assay volume was 30 µL prepared from 15 µL additions of enzyme and substrates (fluoresceinated peptide and ATP) and test compounds in assay buffer (100 mM HEPES pH 7.4, 10 mM $MgCl_2$, 25 mM Beta-Glycerolphosphate, 0.015% Brij35 and 4 mM DTT). The reaction was initiated by the combination of JAK3 with substrates and test compounds. The reaction was incubated at room temperature for 60 min. and terminated by adding 45 µL of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 8 µM; JAK3 fluorescent peptide, 1.5 µM; JAK3, 2.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Cell Proliferation Inhibition Assay

Compounds were evaluated for their ability to inhibit cell proliferation, using an assay that measures thymidine incorporation in the DNA of the dividing cell, which is directly correlated with cell numbers. SET-2 cells were plated at 10000 cells/well in 96-well plates and were cultured for 24 h in RPMI-1640 supplemented with 20% fetal bovine serum, before test compounds were added. Compounds were diluted in culture medium such that the final concentration of dimethyl sulfoxide never exceeded 0.1%. Following the addition of compounds, the cells were cultured for an additional 72 h before cell proliferation was determined by measuring DNA synthesis with 3H-thymidine incorporation.

Compounds described herein were tested in the JAK2 and Cell Proliferation Inhibition assay described above. The following results were obtained.

TABLE 1

| Example# | JAK2 (IC50, uM) | SET-2 (IC50, uM) |
|---|---|---|
| 3 | 1.50E−03 | 0.01 |
| 4 | 0.03 | 2.53 |
| 15 | 1.52E−03 | 0.49 |
| 29 | 0.01 | 10.00 |
| 33 | 6.37E−04 | 0.01 |
| 34 | 1.50E−03 | 0.24 |
| 35 | 5.36E−04 | 2.85 |
| 38 | 0.04 | 0.06 |
| 49 | 0.05 | 3.93 |
| 53 | 1.47E−03 | 0.10 |
| 55 | 7.48E−04 | 4.30E−03 |
| 61 | 7.51E−04 | |
| 70 | 7.33E−04 | 0.33 |
| 73 | 1.00E−03 | 0.06 |
| 81 | 0.01523 | 0.339 |
| 98 | 0.000695 | 0.007365 |
| 101 | 7.43E−04 | 10.00 |
| 109 | 1.52E−03 | 4.15 |
| 116 | 1.49E−03 | 0.17 |
| 125 | 0.05 | 1.27 |

Compounds described herein have been tested in one or more of the above identified assays and have been found to be active.

C. In Vivo Assay

Compound formulated in appropriate vehicle was administered to mice either as an oral bolus or injected intraperitoneally or subcutaneously to Balb/C mice. Blood samples were collected through orbital bleeding or cardiac puncture at various time points post compound administration. Aliquots (90 µL) of the blood were placed in a 96 well plate. Diluted solution (5 ul) of murine thrombopoietin (mTPO; Peprotech) (diluted 1:1000 in dPBS/BSA, 2 µL in 2 ml dPBS/BSA was delivered to each well for pathway stimulation. The plates were incubated at 37° C. in a water bath for 10 minutes. 1.5 ml of fix/lyse solution (from BD Biosciences) was added to each well. The samples were then incubated at 37° C. for 15 minutes to ensure lysis of red blood cells (RBCs). The plates were centrifuged at 2000 rpm for 5 minutes and aspirated using the V&P 96 well aspirator. The cells were washed with dPBS, re-centrifuged, re-suspended and transferred to a regular 96 well plate. The cells were washed twice with dPBS followed by addition of CD61 FITC (from eBiosciences) for surface receptor staining for 45 min in the dark at room temperature. The cells were then washed in dPBS and permeabilized for pSTATS staining as follows: 200 µL of permeabilization buffer III (from BD Bioscience) was added and the samples were incubated on ice for 30 minutes and then samples were washed twice with dPBS/1% BSA and re-suspended in 100 μL of dPBS/BSA containing Stat5 (pY695) Alexa 647 antibodies. The samples were incubated at room temperature in the dark for 45 minutes, washed twice and re-suspended in 10 μL of the Stat5 (pY695) Alexa 647 antibodies used were added to the sample. The samples were re-suspended in 200 μL of dPBS/BSA and run on the FACSCanto on sample images were processed using Diva 6 and FlowJo 8.5.3 analysis software.

Abbreviations

The following abbreviations may be employed in the methods of preparation and Examples:
h=hours
DCM=dichloromethane
THF=tetrahydrofuran
HPLC=high performance liquid chromatography
DIEA=diisopropylethyl amine
i-PrOH=isopropyl alcohol
TFA=trifluoroacetic acid
min=minutes
DMF=dimethylformamide
EDC=N-(3-Dimethylaminopropyl)N'-ethylcarbodiimide
HOBt=hydroxybenzotriazole
NMP=N-methylpyrrolidinone
EtOAc=ethyl acetate
AcOH=acetic acid
BOP reagent=benzotriazole-1-yl-oxy-tris-(dimethylamino)-phasphoniumhexafluorophosphate
brine=saturated aqueous sodium chloride solution
Et$_3$N=triethylamine
t$_R$=retention time
rt—room temperature
NCS=N-chlorosuccinamide
NBS=N-bromosuccinamide
NIS=N-iodosuccinamide Methods of Preparation Compounds of general formula I in which the R group is thiazole (as in Ia1) and $R^1$ and $R^2$ groups are CF$_3$ or alkyl or cycloalkyl or combine to form a saturated carbocyclic or heterocyclic ring or where R2 group is COOR$^b$ could be prepared using the general method depicted in Scheme 1. Dichloro intermediate II (prepared using procedure reported in WO200612237) could be combined with a 2,4-dimethoxybenzyl and the resulting secondary amine is capped with suitable protective group (Boc) (III). The second chlorine atom could be converted into the corresponding amine (IV) through the benzophenone imine intermediate. The amino compound could be halogenated to intermediate V. V could be subjected to transition metal mediated indole ring formation and the resulting indole nitrogen is capped with ethyl iodide to afford VI. Ester hydrolysis followed by amide bond formation and cleavage of protective groups with acid treatment would yield amine VII Amine VII could be converted into thiourea VIII by first coupling with benzoyl isothiocyanate followed treatment with aqueous base. Formation of thiazole could be achieved by condensation with an α-bromoketone derivative (R$^1$CHBrCOR$^2$).

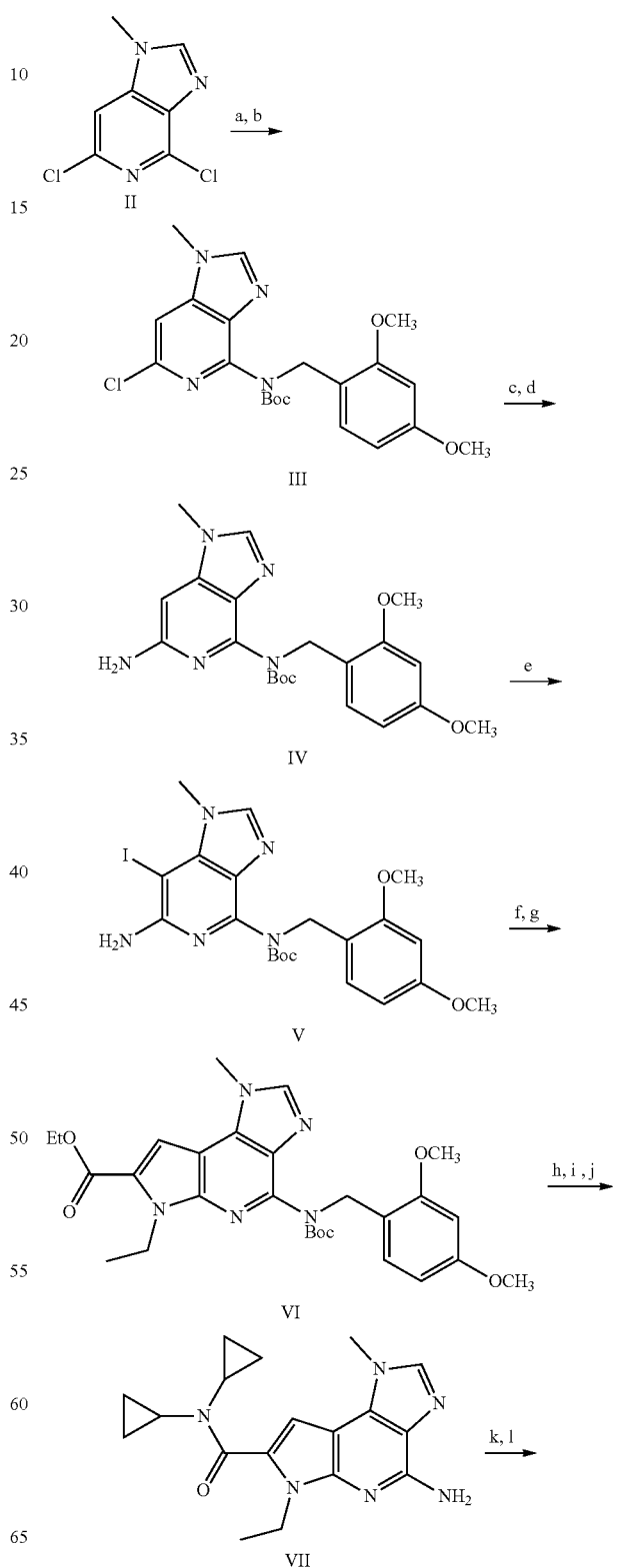

Scheme 1

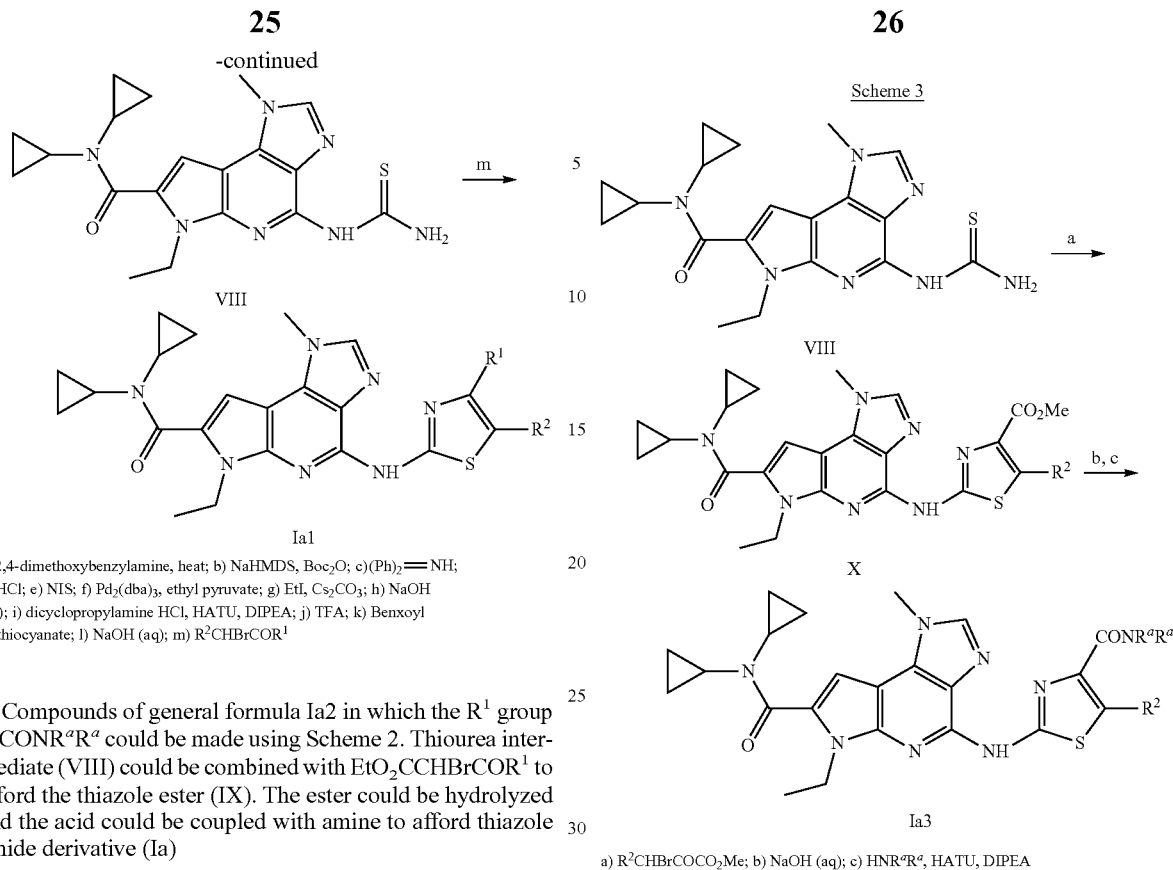

a) 2,4-dimethoxybenzylamine, heat; b) NaHMDS, Boc₂O; c)(Ph)₂=NH; d) HCl; e) NIS; f) Pd₂(dba)₃, ethyl pyruvate; g) EtI, Cs₂CO₃; h) NaOH (aq); i) dicyclopropylamine HCl, HATU, DIPEA; j) TFA; k) Benzoyl isothiocyanate; l) NaOH (aq); m) R²CHBrCOR¹

Compounds of general formula Ia2 in which the R¹ group is CONRᵃRᵃ could be made using Scheme 2. Thiourea intermediate (VIII) could be combined with EtO₂CCHBrCOR¹ to afford the thiazole ester (IX). The ester could be hydrolyzed and the acid could be coupled with amine to afford thiazole amide derivative (Ia)

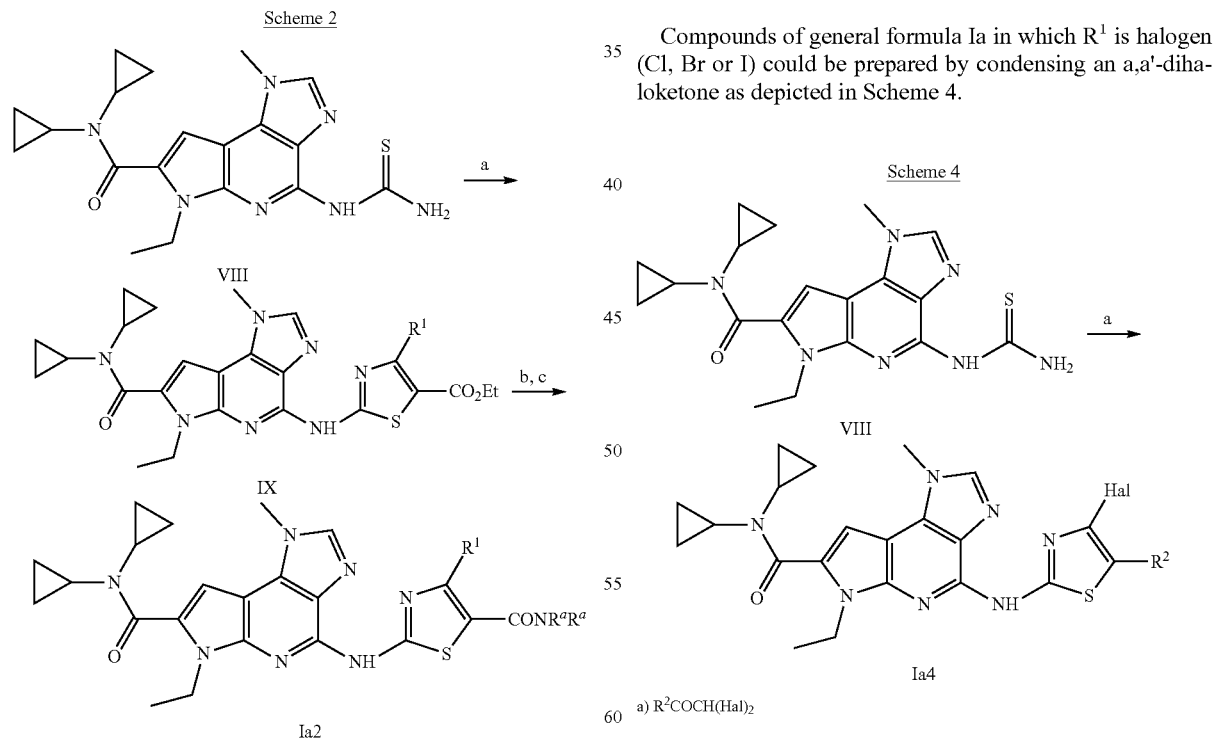

a) EtO₂CCHBrCOR¹; b) NaOH (aq); c) HNRᵃRᵃ, HATU, DIPEA

Similarly, compounds of general formula Ia3 in which the R¹ group is CONRᵃRᵃ could be prepared using the general protocol depicted in Scheme 3.

a) R²CHBrCOCO₂Me; b) NaOH (aq); c) HNRᵃRᵃ, HATU, DIPEA

Compounds of general formula Ia in which R¹ is halogen (Cl, Br or I) could be prepared by condensing an a,a'-dihaloketone as depicted in Scheme 4.

a) R²COCH(Hal)₂

Alternatively, thiourea derivative VIII could be converted to room temperature into C-5 un-substituted thiazole XI and then directly halogenated using electrophilic halogen source or through metallation followed by quenching with an electrophilic halogenating agent (Scheme 5).

Scheme 5

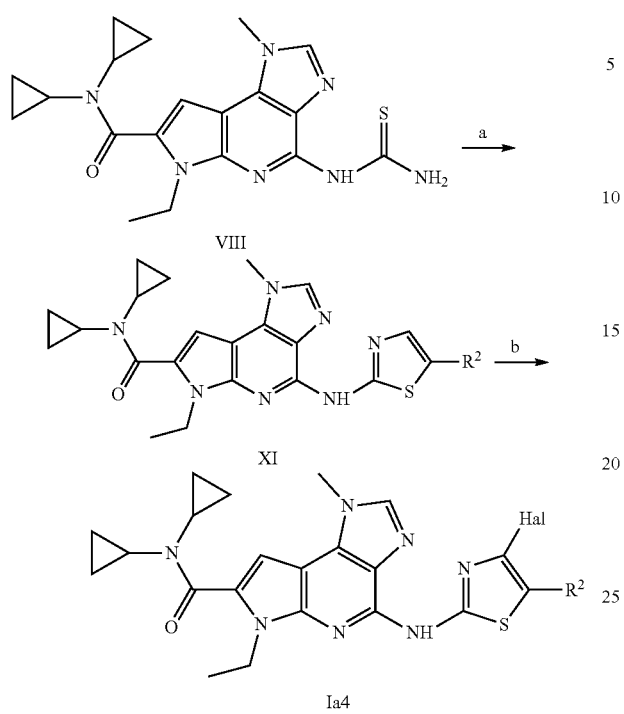

a) BrCH$_2$COR$^2$; b) Selectfluor or NCS or NBS or NIS or tBuLi followed Selectfluor or NBS or NCS Compounds of general formula Ia5 in which R$^1$ is SO$_2$R$^b$ could be synthesized using the general synthetic approach shown in Scheme 6

Scheme 6

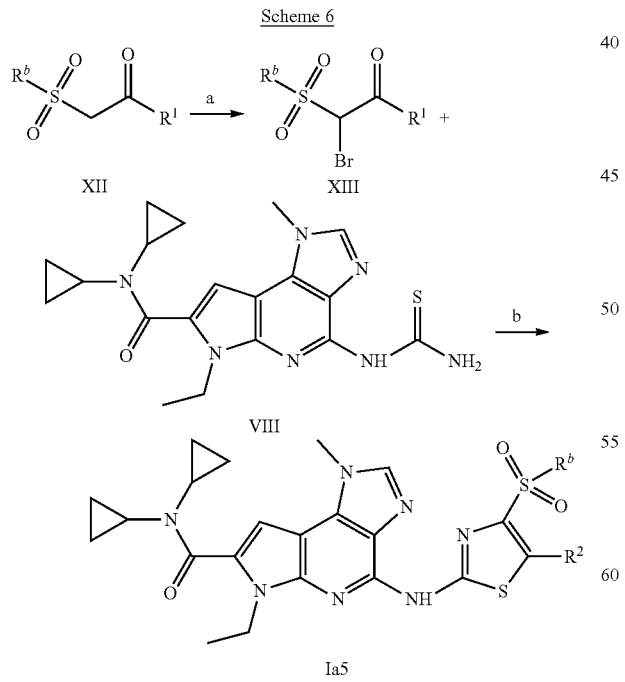

a) Br$_2$-acetic acid; b) EtOH, heat

Compounds with general formula Ia in which R$^1$ and R$^2$ combine to form an aromatic or heteroaromatic ring could be prepared using Scheme 7.

Scheme 7

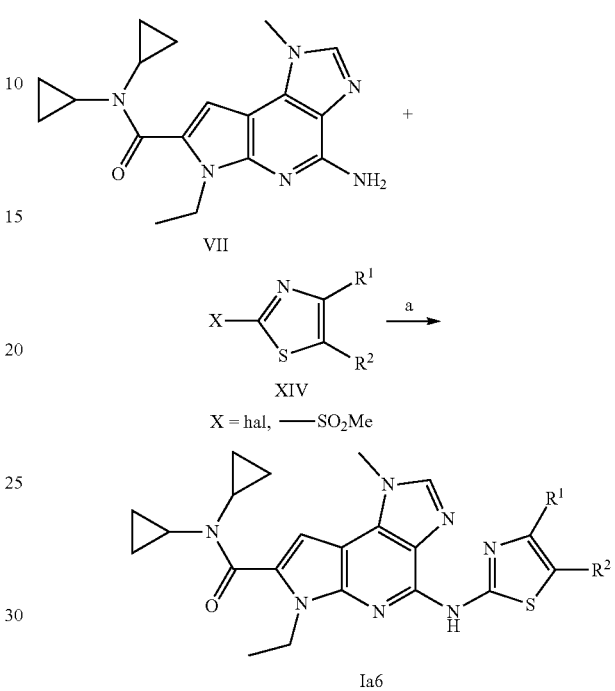

X = hal, —SO$_2$Me a) Pd(0) catalyst, NaOtBu, phosphine ligand, heat

Alternatively, these compounds could be made by first coupling aniline or heteroaniline (XVI) with the isothiocyanate (XV) followed by oxidative cyclization (Scheme 8).

Scheme 8

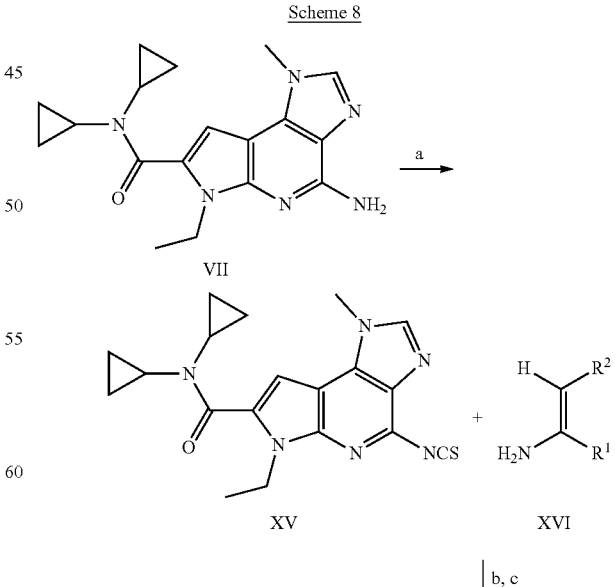

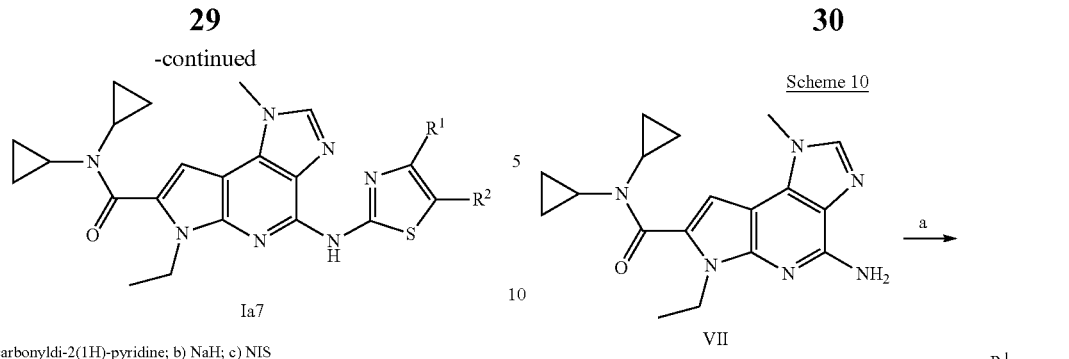

a) 1,1'-Thiocarbonyldi-2(1H)-pyridine; b) NaH; c) NIS

Compounds of general formula Ib1 could be prepared using the general synthetic approach depicted in Scheme 9. Aniline VII could be combined with γ-dithiomethylketone compound XVII, (prepared using the procedure reported at room temperature in *Synlett*, p 2331 (2008)) under basic condition to afford XVIII. Stepwise condensation of the Boc-protected hydrazine derivative would give the required pyrazole Ib1.

Scheme 9

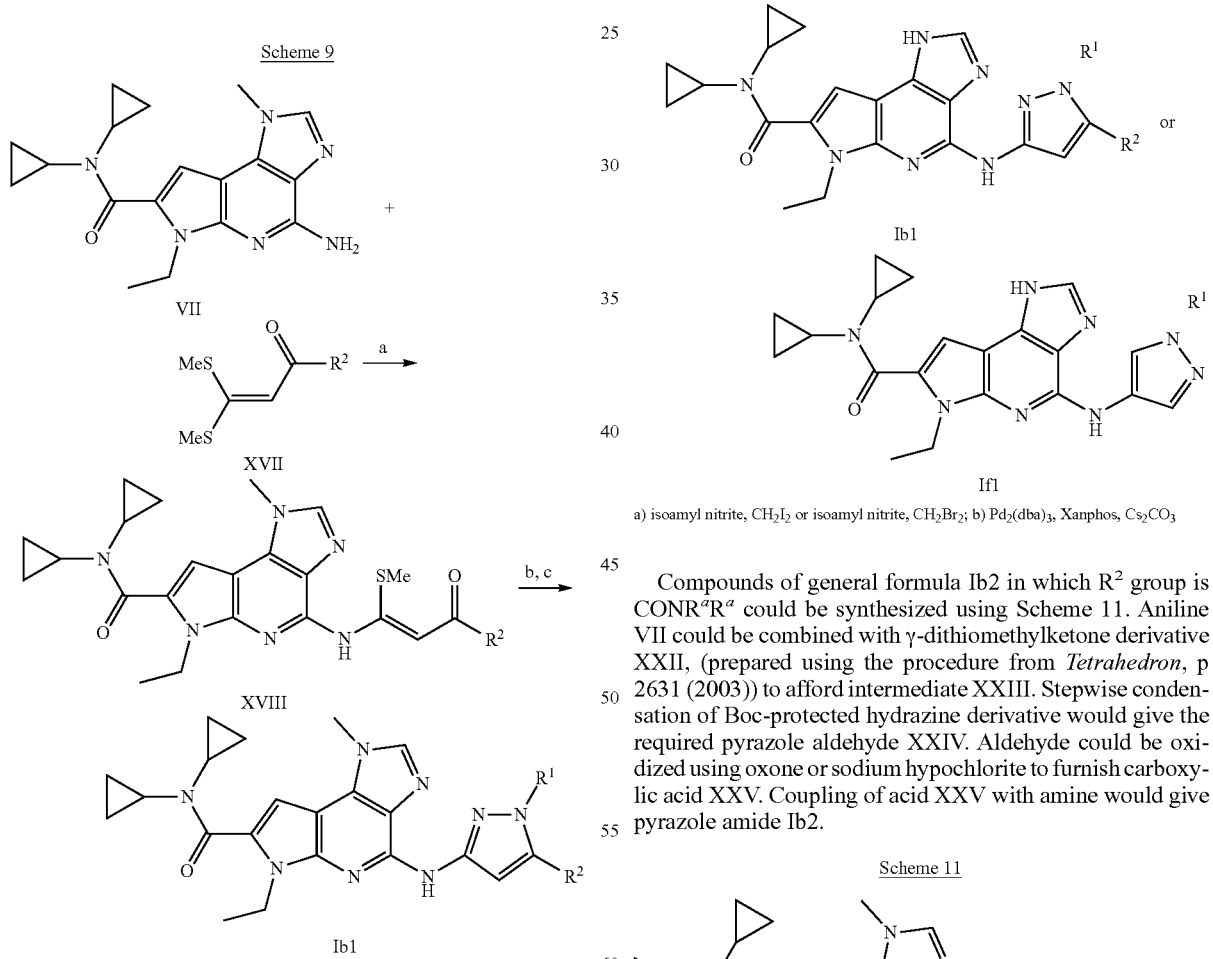

a) NaH, THF; b) R¹N(Boc)NH₂, AcOH, 35-40° C.; c) HCO₂H or TFA, 60° C.

Compounds of general formula Ib1 or If1 and if could also be prepared by coupling C-4 halo derivative (XIX) with an appropriately substituted 2-aminopyrazole derivative (XX) using a transition metal catalyzed reaction (Scheme 10).

Scheme 10 a) isoamyl nitrite, CH₂I₂ or isoamyl nitrite, CH₂Br₂; b) Pd₂(dba)₃, Xanphos, Cs₂CO₃

Compounds of general formula Ib2 in which R² group is CONR$^a$R$^a$ could be synthesized using Scheme 11. Aniline VII could be combined with γ-dithiomethylketone derivative XXII, (prepared using the procedure from *Tetrahedron*, p 2631 (2003)) to afford intermediate XXIII. Stepwise condensation of Boc-protected hydrazine derivative would give the required pyrazole aldehyde XXIV. Aldehyde could be oxidized using oxone or sodium hypochlorite to furnish carboxylic acid XXV. Coupling of acid XXV with amine would give pyrazole amide Ib2.

Scheme 11

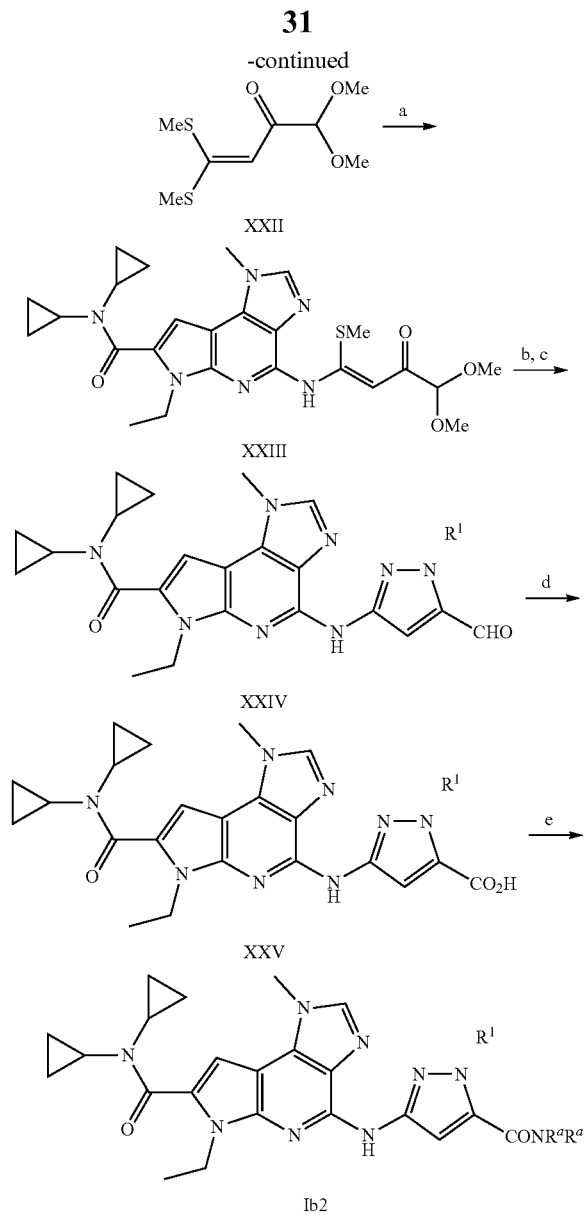

a) NaH, THF, heat; b) R¹N(Boc)NH2, AcOH; c) TFA; d) oxone or sodium hypochlorite; e) HNR^aR^a, HATU, DIPEA Compounds of general formula Ic1 could be prepared using the general protocol as shown in Scheme 12. Aniline VII could be coupled with chloroacetyl chloride and the resulting amide could be treated with thioamide (R²CSNH₂) to furnish thiazole Ic1.

Scheme 12

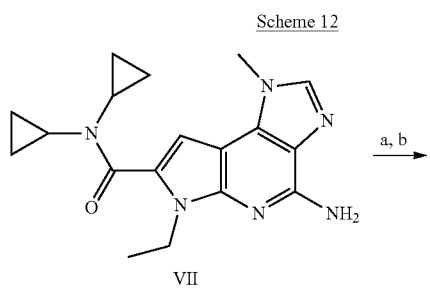

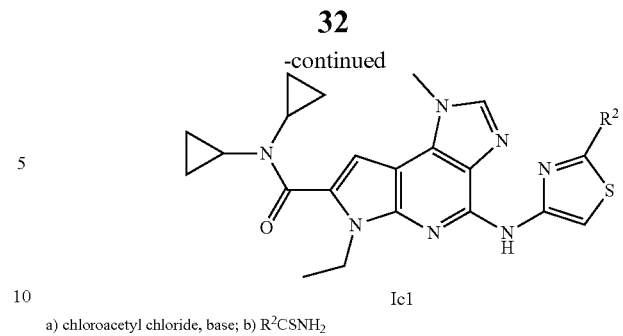

a) chloroacetyl chloride, base; b) R²CSNH₂

Compounds of general formula 1d1 could be made as per Scheme 13. Previously described isothiocyanate derivative XV could be combined with amidine XXV under dehydrating reaction conditions to give 1,2,4-thiadiazole (Id1).

Scheme 13

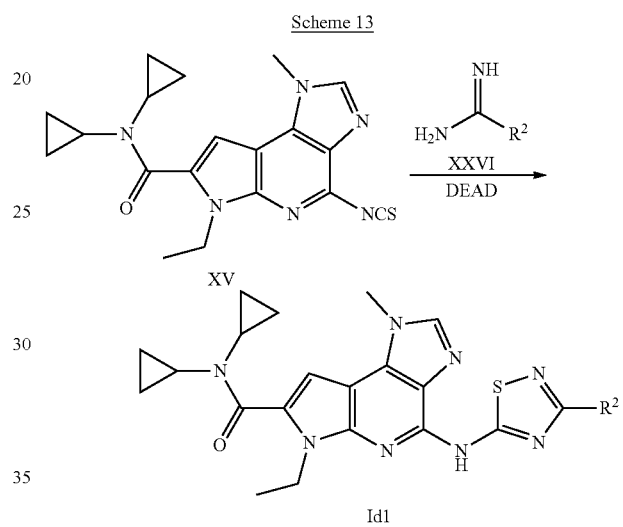

Compounds of general formula 1e1 could be prepared using a synthetic approach as shown in Scheme 14. Isothiocyanate XV could be combined with azide XXVI in the presence of phosphine to yield 1,3-oxazole Te1.

Scheme 14

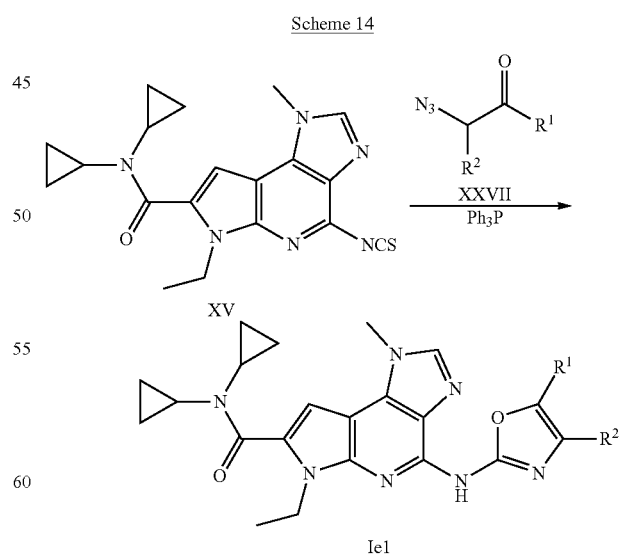

Compounds of general formula 1g1 could be prepared using a synthetic approach as shown in Scheme 15. Amine VII could be combined with acyl isothiocyanate XXVII. The acylthioureaido could be condensed with hydrazine derivative to yield the 1,2,4-triazol derivative 1g1.

Scheme 15

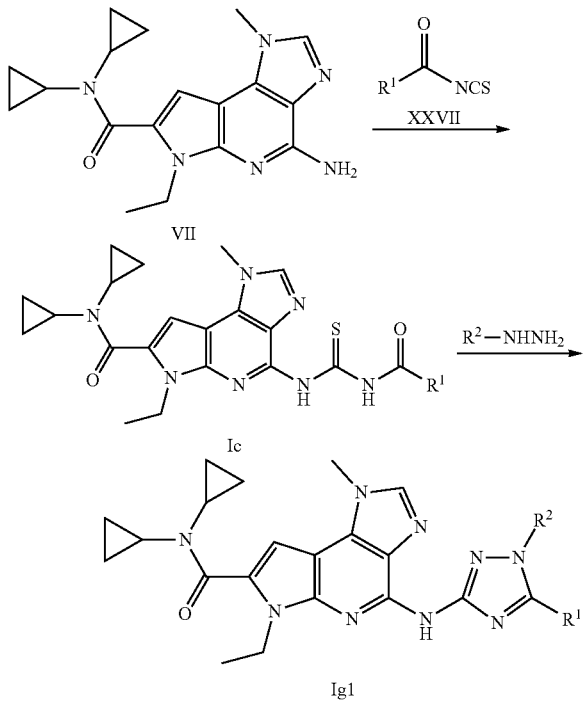

EXAMPLES

Example 1

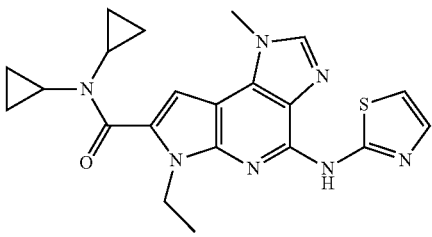 [SMILES: CCn1c(C(=O)N(C2CC2)C2CC2)cc2c3c(ncn3C)c(Nc3nccs3)nc21]

N,N-dicyclopropyl-6-ethyl-1-methyl-4-(thiazol-2-ylamino)-1,6-dihydroimidazo[4,5-d]pyrrolo[2,3-b]pyridine-7-carboxamide 1A Preparation of 6-chloro-N-(2,4-dimethoxybenzyl)-1-methyl-1H-imidazo[4,5-c]pyridin-4-amine

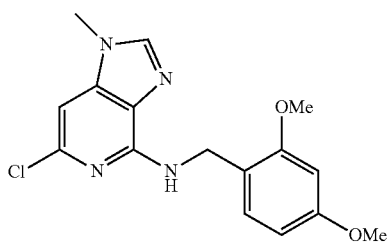 [SMILES: COc1ccc(CNc2nc(Cl)cc3c2ncn3C)c(OC)c1]

In a 200 mL round bottom flask, 4,6-dichloro-1-methyl-1H-imidazo[4,5-c]pyridine (15 g, 74.2 mmol) (prepared as per WO2006122137 example A1.5) was dissolved in 2,4-dimethoxybenzylamine (25 mL, 166 mmol). The reaction mixture was heated to 110° C. for 3 h and cooled to room temperature. Water was added and a tan colored solid precipitated out. Vacuum filtration yielded a tan solid. The solid was washed with ethyl acetate and hexane to yield 6-chloro-N-(2,4-dimethoxybenzyl)-1-methyl-1H-imidazo[4,5-c]pyridin-4-amine (23.459 g, 95% yield) as a cream colored solid.

MS (ESI) m/z 333.0 (M+H)

1H NMR (500 MHz, DMSO-$d_6$) δ ppm 8.05 (s, 1 H), 7.17 (t, 1 H, J=6.19 Hz), 7.06 (d, 1 H, J=8.25 Hz), 6.87 (s, 1 H), 6.55 (d, 1 H, J=2.47 Hz), 6.42 (dd, 1 H, J=8.52, 2.47 Hz), 4.54 (d, 2 H, J=5.77 Hz), 3.82 (s, 3 H), 3.74 (s, 3 H), 3.72 (s, 3 H)

1B Preparation of tert-butyl 6-chloro-1-methyl-1H-imidazo[4,5-c]pyridin-4-yl(2,4-dimethoxybenzyl)carbamate

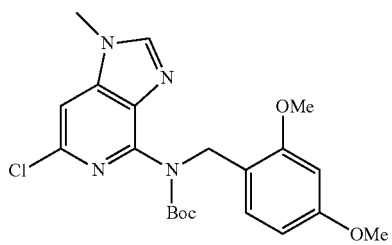 [SMILES: COc1ccc(CN(C(=O)OC(C)(C)C)c2nc(Cl)cc3c2ncn3C)c(OC)c1]

To a solution of 6-chloro-N-(2,4-dimethoxybenzyl)-1-methyl-1H-imidazo[4,5-c]pyridin-4-amine (example 1A, 0.63 g, 1.893 mmol) in tetrahydrofuran (38 mL) cooled to −78° C., was added NaHMDS (1.0 M THF, 2.366 mL, 2.366 mmol) slowly. After stirring at −78° C. for 30 min, BOC$_2$O (0.483 mL, 2.082 mmol) was added. The cold bath was removed and the reaction was allowed to warm to rt ON. By HPLC, ~50% conversion was observed. The solution was re-cooled to −78° C. NaHMDS (1.0 M THF, 2.366 mL, 2.366 mmol) was added and the mixture was stirred 30 min before the addition of BOC$_2$O (0.483 mL, 2.082 mmol). The cold bath was removed and the reaction warmed to room temperature 5 h. The solvent was removed under reduced pressure and the residue partitioned between ethyl acetate and water. The organic layer was washed twice with water, dried over anhydrous magnesium sulfate, filtered and concentrated in vacuo. The crude residue was purified by flash chromatography using an Isco 40 g column eluting with 50-100% ethyl acetate/hexane to yield tert-butyl 6-chloro-1-methyl-1H-imidazo[4,5-c]pyridin-4-yl(2,4-dimethoxybenzyl) carbamate (0.638 g, 78% yield) as a foamy white solid.

MS (ESI) m/z 433.0 (M+H)

1H NMR (400 MHz, CHLOROFORM-d) δ ppm 7.91 (s, 1 H), 7.47 (d, 1H, J=8.31 Hz), 7.19 (s, 1 H), 6.38 (dd, 1 H, J=8.31, 2.52 Hz), 6.32 (d, 1 H, J=2.52 Hz), 5.13 (s, 2 H), 3.80 (s, 3 H), 3.74 (s, 3 H), 3.59 (s, 3 H), 1.40 (s, 9 H)

1C Preparation of tert-butyl 2,4-dimethoxybenzyl(6-(diphenylmethyleneamino)-1-methyl-1H-imidazo[4,5-c]pyridin-4-yl)carbamate

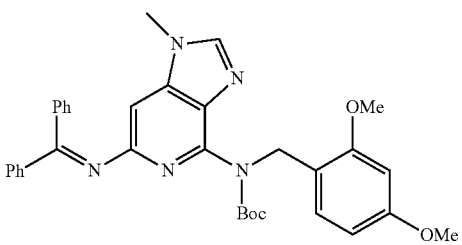 [SMILES: COc1ccc(CN(C(=O)OC(C)(C)C)c2nc(N=C(c3ccccc3)c3ccccc3)cc3c2ncn3C)c(OC)c1]

Anhydrous dioxane (4 mL) was added to a mixture of tert-butyl 6-chloro-1-methyl-1H-imidazo[4,5-c]pyridin-4-yl (2,4-dimethoxybenzyl)carbamate (example 1B, 0.638 g, 1.474 mmol), benzophenone imine (0.297 mL, 1.769 mmol), Pd$_2$(dba)$_3$ (0.270 g, 0.295 mmol), 9,9-dimethyl-4,5-bis (diphenylphosphino)xanthene (0.256 g, 0.442 mmol), and cesium carbonate (0.672 g, 2.063 mmol). The reaction mixture was heated to 90° C. overnight. After cooling to rt, solvent was removed in vacuo. The residue was partitioned between ethyl acetate and water. The organic layer was washed twice with water, dried over anhydrous magnesium sulfate, filtered and concentrated in vacuo. The crude residue was purified by flash chromatography using an Isco 40 g column eluting with 50-100% ethyl acetate/hexane to provide tert-butyl 2,4-dimethoxybenzyl(6-(diphenylmethyleneamino)-1-methyl-1H-imidazo[4,5-c]pyridin-4-yl)carbamate (0.757 g, 89% yield) as a light yellow solid.

MS (ESI) m/z 414.0 (M-CPh$_2$+2H)

1H NMR (400 MHz, DMSO-d$_6$) δ ppm 8.16 (s, 1 H), 7.67 (dd, 2 H, J=8.56, 1.51 Hz), 7.44-7.60 (m, 3 H), 7.25 (d, 1 H, J=8.31 Hz), 6.96-7.11 (m, 4 H), 6.87 (s, 1 H), 6.46 (d, 1 H, J=2.52 Hz), 6.33 (dd, 1 H, J=8.56, 2.27 Hz), 4.52 (s, 2 H), 3.70 (s, 3 H), 3.69 (s, 3 H), 3.67 (s, 3 H), 1.25 (s, 9 H)

1D Preparation of tert-butyl 6-amino-1-methyl-1H-imidazo[4,5-c]pyridin-4-yl(2,4-dimethoxybenzyl)carbamate

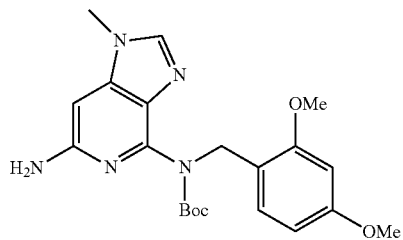 [SMILES: COc1ccc(CN(C(=O)OC(C)(C)C)c2nc(N)cc3c2ncn3C)c(OC)c1]

In a 1000 mL round bottom flask, tert-butyl 2,4-dimethoxybenzyl(6-(diphenylmethyleneamino)-1-methyl-1H-imidazo[4,5-c]pyridin-4-yl)carbamate (example 1C, 9.2 g, 15.93 mmol) was stirred in THF (50 mL). 1 N HCl (33 mL) was added. After 2 min, the reaction was quenched with 1 N NaOH (65 mL) and ethyl acetate (100 mL). The organic layer was separated, dried over anhydrous sodium sulfate, filtered and concentrated in vacuo. The residue was dried under vacuum for 1 h and triturated with ether (4×). Isolated tert-butyl 6-amino-1-methyl-1H-imidazo[4,5-c]pyridin-4-yl(2,4-dimethoxybenzyl) carbamate (6.587 g, 15.93 mmol, 100% yield) as a cream solid. Material carried forward with no further purification.

MS (ESI) m/z 413.0 (M+H)

1H NMR (400 MHz, DMSO-d$_6$) δ ppm 7.93 (s,1 H), 7.44 (d, 1 H, J=8.31 Hz), 6.44 (d, 1 H, J=2.27 Hz), 6.35 (dd, 1 H, J=8.56, 2.27 Hz), 6.25 (s, 1 H), 5.58 (s, 2 H), 4.87 (s, 2 H), 3.67 (s, 6 H), 3.63 (s, 3 H), 1.30 (s, 9 H)

1E Preparation of tert-butyl 6-amino-7-iodo-1-methyl-1H-imidazo[4,5-c]pyridin-4-yl(2,4-dimethoxybenzyl)carbamate

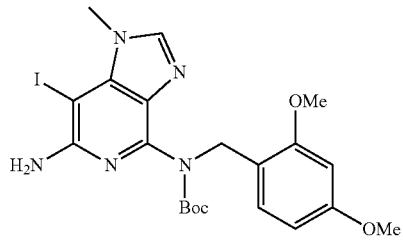 [SMILES: COc1ccc(CN(C(=O)OC(C)(C)C)c2nc(N)c(I)c3c2ncn3C)c(OC)c1]

In a round bottom flask, tert-butyl 6-amino-1-methyl-1H-imidazo[4,5-c]pyridin-4-yl(2,4-dimethoxybenzyl)carbamate (example 1D, 7.887 g, 19.08 mmol) was dissolved in MeCN (200 mL) and cooled to 0° C. N-Iodosuccinimide (4.51 g, 20.03 mmol) was dissolved in the remaining MeCN (50 mL) and added dropwise to the reaction mixture over 40 min. The reaction mixture was stirred at 0° C. for an additional 10 min and was quenched with 2 M sodium hydrogensulfite (125 mL). Stirring and temperature were maintained for 50 min. The mixture was transferred to a separatory funnel The aqueous layer was extracted with CH$_2$Cl$_2$ (3×100 mL). The combined organic layers were washed with water and brine, dried over Na$_2$SO$_4$, filtered and concentrated in vacuo. The crude residue was purified by flash chromatography using an Isco 120 g column eluting with 20-100% ethyl acetate/CH$_2$Cl$_2$ to provide tert-butyl 6-amino-7-iodo-1-methyl-1H-imidazo[4,5-c]pyridin-4-yl(2,4-dimethoxybenzyl)carbamate (8.436 g, 82% yield) as a pale yellow solid.

MS (ESI) m/z 539.0 (M)

1H NMR (400 MHz, DMSO-d$_6$) δ ppm 8.00 (s, 1 H), 7.40 (d, 1 H, J=8.06 Hz), 6.43 (d, 1 H, J=2.52 Hz), 6.31-6.39 (m, 1 H), 5.73 (s, 2 H), 4.86 (s, 2 H), 3.95 (s, 3 H), 3.67 (s, 3 H), 3.64 (s, 3 H), 1.30 (s, 9 H)

1F Preparation of ethyl 4-(tert-butoxycarbonyl(2,4-dimethoxybenzyl)amino)-1-methyl-1,6-dihydroimidazo[4,5-d]pyrrolo[2,3-b]pyridine-7-carboxylate

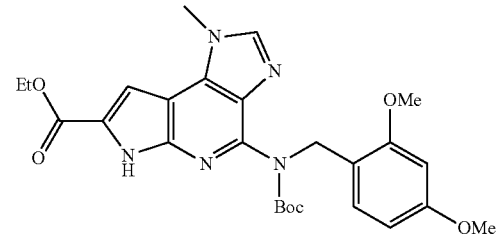 [SMILES: CCOC(=O)c1cc2c(nc(N(Cc3ccc(OC)cc3OC)C(=O)OC(C)(C)C)c3ncn(C)c32)[nH]1]

To a flask charged with tert-butyl 6-amino-7-iodo-1-methyl-1H-imidazo[4,5-c]pyridin-4-yl(2,4-dimethoxybenzyl)carbamate (example 1E, 3.49 g, 6.47 mmol) in DMA (43.1 mL) was added Pd$_2$(dba)$_3$ (0.474 g, 0.518 mmol), ethyl pyruvate (7.22 mL, 64.7 mmol), and N-methyldicyclohexylamine (2.77 mL, 12.94 mmol). The reaction mixture was sparged with argon for 10 min and heated at 60° C. 6 h. The reaction was complete by LCMS. After cooling to room temperature, the reaction mixture was diluted with ethyl acetate and saturated aqueous NaHCO$_3$. The resultant emulsion was vacuum filtered through a pad of Celite and transferred to a separatory funnel The aqueous layer was extracted with ethyl acetate. The combined organic layers were washed with 10% aqueous LiCl solution (2×). The organic phase was dried over MgSO$_4$, filtered and concentrated in vacuo. The brown residue was purified by flash chromatography using an Isco 120 g column eluting with 40-80% ethyl acetate/hexane to yield ethyl 4-(tert-butoxycarbonyl(2,4-dimethoxybenzyl)amino)-1-methyl-1,6-dihydroimidazo[4,5-d]pyrrolo[2,3-b]pyridine-7-carboxylate (2.830 g, 86% yield)

MS (ESI) m/z 510.0 (M+H)

1H NMR (400 MHz, CHLOROFORM-d) δ ppm 7.83 (s, 1 H), 7.57 (d, 1H, J=8.31 Hz), 7.39 (d, 1 H, J=2.27 Hz), 6.40 (dd, 1 H, J=8.44, 2.39 Hz), 6.32 (d, 1 H, J=2.52 Hz), 5.16 (s, 2 H), 4.43 (q, 2 H, J=7.05 Hz), 4.09 (s, 3 H), 3.74 (s, 3 H), 3.56 (s, 3 H), 1.43 (t, 3 H, J=7.18 Hz), 1.40 (s, 9 H)

1G Preparation of ethyl 4-(tert-butoxycarbonyl(2,4-dimethoxybenzyl)amino)-6-ethyl-1-methyl-1,6-dihydroimidazo[4,5-d]pyrrolo[2,3-b]pyridine-7-carboxylate

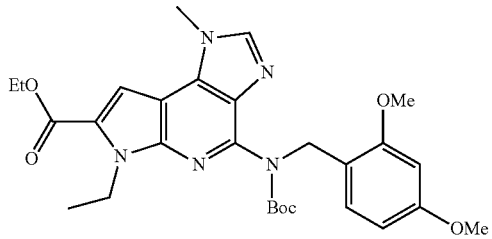 [SMILES: CCn1c(C(=O)O)cc2c3c(ncn3C)c(N(Cc3ccc(OC)cc3OC)C(=O)OC(C)(C)C)nc21]

To a solution of ethyl 4-(tert-butoxycarbonyl(2,4-dimethoxybenzyl)amino)-1-methyl-1,6-dihydroimidazo[4,5-d]pyrrolo[2,3-b]pyridine-7-carboxylate (example 1F, 5.046 g, 9.90 mmol) in DMF (49.5 mL) was added ethyl iodide (1.601 mL, 19.81 mmol) and cesium carbonate (6.45 g, 19.81 mmol). The reaction mixture was heated at 60° C. 60 min and cooled to room temperature. The reaction mixture was diluted with ethyl acetate and vacuum filtered to remove cesium carbonate. Saturated aqueous sodium bicarbonate was added and the aqueous layer was extracted with ethyl acetate (2×). The combined organic layers were washed with 10% lithium chloride (3×), dried over anhydrous magnesium sulfate, filtered and concentrated in vacuo. Crude product was carried forward.

MS (ESI) m/z 538.1 (M+H)

1H NMR (400 MHz, CHLOROFORM-d) δ ppm 7.79 (s, 1 H), 7.62 (d, 1H J=8.28 Hz), 7.43 (s, 1 H), 6.39 (dd, 1 H, J=8.41, 2.38 Hz), 6.32 (d, 1 H, J=2.26 Hz), 5.20 (s, 2 H), 4.79 (q, 2 H, J=7.03 Hz), 4.41 (q, 2 H, J=7.28 Hz), 4.07 (s, 3 H), 3.74 (s, 3 H), 3.61 (s, 3 H), 1.44 (t, 3 H, J=7.15 Hz), 1.41 (s, 9 H), 1.37 (t, 3 H, J=7.03 Hz)

1H Preparation of 4-(tert-butoxycarbonyl(2,4-dimethoxybenzyl)amino)-6-ethyl-1-methyl-1,6-dihydroimidazo[4,5-d]pyrrolo[2,3-b]pyridine-7-carboxylic acid

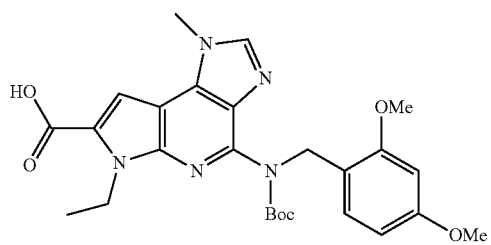

To a solution of ethyl 4-(tert-butoxycarbonyl(2,4-dimethoxybenzyl)amino)-6-ethyl-1-methyl-1,6-dihydroimidazo[4,5-d]pyrrolo[2,3-b]pyridine-7-carboxylate (example 1G, 5.32 g, 9.9 mmol) in ethanol (49.5 mL) was added 1 N NaOH aqueous solution (49.5 mL). The reaction mixture was heated at 60° C. 3 h and cooled to rt. Ethanol was removed by concentration in vacuo. The residue was acidified with 1 N HCl and the product was collected by vacuum filtration. 4-(tert-Butoxycarbonyl(2,4-dimethoxybenzyl)amino)-6-ethyl-1-methyl-1,6-dihydroimidazo[4,5-d]pyrrolo[2,3-b]pyridine-7-carboxylic acid (4.3 g, 8.44 mmol, 85% yield over two steps) was isolated as a white solid after drying on the vacuum.

MS (ESI) m/z 510.0 (M+H)

1I Preparation of tert-butyl 7-(dicyclopropylcarbamoyl)-6-ethyl-1-methyl-1,6-dihydroimidazo[4,5-d]pyrrolo[2,3-b]pyridin-4-yl(2,4-dimethoxybenzyl)carbamate

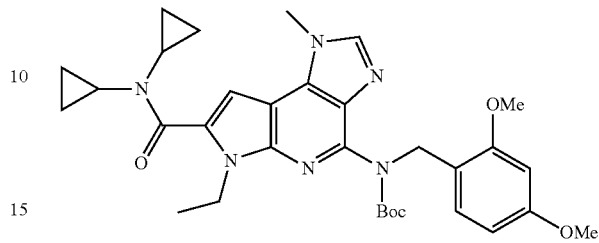

To a mixture of 4-(tert-butoxycarbonyl(2,4-dimethoxybenzyl)amino)-6-ethyl-1-methyl-1,6-dihydroimidazo[4,5-d]pyrrolo[2,3-b]pyridine-7-carboxylic acid (example 1H, 0.89 g, 1.747 mmol) in acetonitrile (17.47 mL) was added dicyclopropylamine hydrochloride (0.303 g, 2.271 mmol), N-methylmorpholine (0.499 mL, 4.54 mmol), DMAP (0.021 g, 0.175 mmol), and HATU (0.797 g, 2.096 mmol). The reaction mixture was stirred at rt 5 h and heated to 50° C. for 45 min. The reaction was cooled to room temperature. Acetonitrile was removed in vacuo and the residue was partitioned between saturated aqueous sodium bicarbonate and dichloromethane. The aqueous layer was extracted with dichloromethane. The combined organic layers were dried over anhydrous sodium sulfate, filtered and concentrated in vacuo. The crude solid was purified by flash chromatography using an Isco 80 g column eluting with 1-4% MeOH/CH$_2$Cl$_2$ to yield tert-butyl 7-(dicyclopropylcarbamoyl)-6-ethyl-1-methyl-1,6-dihydroimidazo[4,5-d]pyrrolo[2,3-b]pyridin-4-yl (2,4-dimethoxybenzyl)carbamate (0.8 g, 78% yield) as an off-white solid.

MS (ESI) m/z 589.0 (M+H)

1H NMR (400 MHz, CHLOROFORM-d) δ ppm 7.78 (s, 1 H), 7.67 (d, 1H, J=8.28 Hz), 6.85 (s, 1 H), 6.40 (dd, 1 H, J=8.41, 2.38 Hz), 6.33 (d, 1 H, J=2.51 Hz), 5.20 (s, 2 H), 4.58 (q, 2 H, J=7.03 Hz), 4.02 (s, 3 H), 3.74 (s, 3 H), 3.62 (s, 3 H), 2.77-2.85 (m, 2 H), 1.42 (s, 9 H), 1.39 (t, 3 H, J=7.40 Hz), 0.80-0.89 (m, 4 H), 0.72-0.78 (m, 4 H)

1J Preparation of 4-amino-N,N-dicyclopropyl-6-ethyl-1-methyl-1,6-dihydroimidazo[4,5-d]pyrrolo[2,3-b]pyridine-7-carboxamide

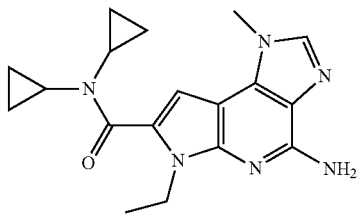 [SMILES: CCn1c(C(=O)N(C2CC2)C2CC2)cc2c3c(ncn3C)c(N)nc21]

To a solution of tert-butyl 7-(dicyclopropylcarbamoyl)-6-ethyl-1-methyl-1,6-dihydroimidazo[4,5-d]pyrrolo[2,3-b]pyridin-4-yl(2,4-dimethoxybenzyl)carbamate (example 1I, 2.66 g, 4.51 mmol) in dichloromethane (33.8 mL) was added TFA (11.28 mL). The reaction mixture was stirred at rt 45 min and was concentrated in vacuo. The crude residue was partitioned between ethyl acetate and saturated aqueous sodium bicarbonate. The aqueous layer was extracted with ethyl acetate (2 x) and the combined organics were dried over anhydrous sodium sulfate, filtered and concentrated in vacuo.

The crude solid was purified by flash chromatography using an Isco 40 g column eluting with 4-10% MeOH/CH$_2$Cl$_2$ to yield 4-amino-N,N-dicyclopropyl-6-ethyl-1-methyl-1,6-dihydroimidazo[4,5-d]pyrrolo[2,3-b]pyridine-7-carboxamide (1.2 g, 3.55 mmol, 79% yield) as a pale yellow solid.

MS (ESI) m/z 339.2 (M+H)

1H NMR (400 MHz, MeOD) δ ppm 7.95 (s, 1 H), 7.15 (s, 1 H), 4.51 (q, 2H J=7.13 Hz), 4.04 (s, 3 H), 2.89-2.98 (m, 2 H), 1.35 (t, 3 H), 0.82-0.91 (m, 4 H), 0.70-0.81 (m, 4 H)

1 Preparation of N,N-dicyclopropyl-6-ethyl-1-methyl-4-(thiazol-2-ylamino)-1,6-dihydroimidazo[4,5-d]pyrrolo[2,3-b]pyridine-7-carboxamide To a mixture of 4-amino-N,N-dicyclopropyl-6-ethyl-1-methyl-1,6-dihydroimidazo[4,5-d]pyrrolo[2,3-b]pyridine-7-carboxamide (example 1J, 30 mg, 0.089 mmol), 2-bromothiazole (11.98 μL, 0.133 mmol), Pd$_2$(dba)$_3$ (12.18 mg, 0.013 mmol), BINAP (24.84 mg, 0.040 mmol) and sodium tert-butoxide (13.63 mg, 0.142 mmol) was added PhMe (887 μL). The mixture was sparged with argon gas for 5 min and heated to 85° C. for 5.5 h. The reaction mixture was filtered through a plug of Celite and concentrated. The crude residue was purified by preparative HPLC to provide N,N-dicyclopropyl-6-ethyl-1-methyl-4-(thiazol-2-ylamino)-1,6-dihydroimidazo[4,5-d]pyrrolo[2,3-b]pyridine-7-carboxamide (4 mg, 10.49% yield) along with some recovered starting material.

MS (ESI) m/z 423.0 (M+H)

1H NMR (500 MHz, DMSO-d$_6$) δ ppm 8.14 (s, 1H), 7.47 (d, 1H, J=3.57 Hz), 7.24 (s, 1H), 7.14 (d, 1H, J=3.57 Hz), 4.63 (q, 2H, J=6.87 Hz), 4.05 (s, 3H), 2.88-2.99 (m, 2H), 1.39 (t, 3H, J=7.01 Hz), 0.73-0.81 (m, 4H), 0.64-0.70 (m, 4H)

Example 2

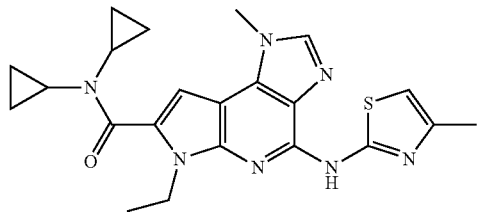 [SMILES: CCn1c(C(=O)N(C2CC2)C2CC2)cc2c3c(ncn3C)c(Nc3nc(C)cs3)nc21]

N,N-dicyclopropyl-6-ethyl-1-methyl-4-(4-methylthiazol-2-ylamino)-1,6-dihydroimidazo[4,5-d]pyrrolo[2,3-b]pyridine-7-carboxamide 2A Preparation of 4-(3-benzoylthioureido)-N,N-dicyclopropyl-6-ethyl-1-methyl-1,6-dihydroimidazo[4,5-d]pyrrolo[2,3-b]pyridine-7-carboxamide

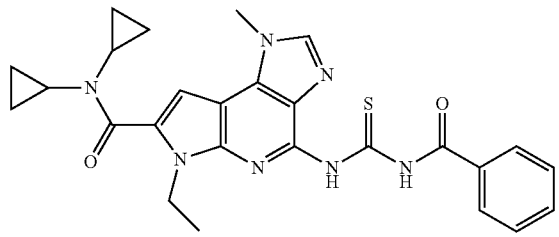 [SMILES: CCn1c(C(=O)N(C2CC2)C2CC2)cc2c3c(ncn3C)c(NC(=S)NC(=O)c3ccccc3)nc21]

A solution of 4-amino-N,N-dicyclopropyl-6-ethyl-1-methyl-1,6-dihydroimidazo[4,5-d]pyrrolo[2,3-b]pyridine-7-carboxamide (example 1J, 234 mg, 0.69 mmol) and benzoyl isothiocyanate (0.1 ml, 0.83 mmol) in acetone (3 ml) was stirred at room temperature for 3 h. The reaction mixture was cooled to 0° C. and water was added. The resulting brown solid was collected by filtration and air-dried to give 4-(3-benzoylthioureido)-N,N-dicyclopropyl-6-ethyl-1-methyl-1,6-dihydroimidazo[4,5-d]pyrrolo[2,3-b]pyridine-7-carboxamide (306 mg, 88% yield)

MS (ESI) rt=1.86 min, m/z 502 (M+H).

1H NMR (400 MHz, DMSO-d6) δ ppm 8.44 (br. s., 1 H) 7.99-8.07 (m, 2 H) 7.64-7.74 (m, 1 H) 7.58 (t, J=7.65 Hz, 2 H) 7.34 (s, 1 H) 4.47 (br. s., 2 H) 4.11 (s, 3 H) 2.90-2.99 (m, 2 H) 2.08 (s, 1 H) 1.28 (br. s., 3 H) 0.64-0.81 (m, 8 H).

2B Preparation of N,N-dicyclopropyl-6-ethyl-1-methyl-4-thioureido-1,6-dihydroimidazo[4,5-d]pyrrolo[2,3-b]pyridine-7-carboxamide

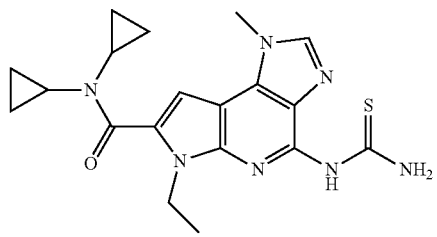 [SMILES: CCn1c(C(=O)N(C2CC2)C2CC2)cc2c3c(ncn3C)c(NC(N)=S)nc21]

4-(3-Benzoylthioureido)-N,N-dicyclopropyl-6-ethyl-1-methyl-1,6-dihydroimidazo[4,5-d]pyrrolo[2,3-b]pyridine-7-carboxamide (example 2A, 306 mg, 0.61 mmol) and 1N NaOH (10 ml, 10.00 mmol) in 10 ml EtOH were heated at 60° C. for 1 h. The reaction was cooled to room temperature and concentrated. The remaining aqueous solution was extracted (3×) with ethyl acetate. The organic phase was dried over Na$_2$SO$_4$, filtered, and concentrated. Purification by silica gel chromatography (dichloromethane/methanol 0-4%) gave N,N-dicyclopropyl-6-ethyl-1-methyl-4-thioureido-1,6-dihydroimidazo[4,5-d]pyrrolo[2,3-b]pyridine-7-carboxamide as a yellow solid (199 mg, 82% yield).

MS (ESI) m/z 398 (M+H).

1H NMR (400 MHz, CHLOROFORM-d) δ ppm 11.02 (br. s., 1 H) 9.27 (s, 2 H) 7.75 (s, 1 H) 6.89 (s, 1 H) 4.52 (q, J=7.12 Hz, 2 H) 4.06 (s, 3 H) 2.77-2.90 (m, 2 H) 1.45 (t, J=7.15 Hz, 3 H) 0.73-0.97 (m, 8 H).

2 Preparation of N,N-dicyclopropyl-6-ethyl-1-methyl-4-(4-methylthiazol-2-ylamino)-1,6-dihydroimidazo[4,5-d]pyrrolo[2,3-b]pyridine-7-carboxamide N,N-dicyclopropyl-6-ethyl-1-methyl-4-thioureido-1,6-dihydroimidazo[4,5-d]pyrrolo[2,3-b]pyridine-7-carboxamide (example 2B, 40 mg, 0.10 mmol) and chloroacetone (62.4 mg, 0.40 mmol) in EtOH (2 ml) were heated at 80° C. for 20 min. The reaction was cooled to room temperature and the solvent removed in vacuo. Saturated NaHCO$_3$ solution was added and the aqueous layer extracted (3×) with dichloromethane. The organic layers were combined, dried over Na$_2$SO$_4$, filtered, and concentrated. The crude material was purified by silica gel chromatography (dichloromethane/methanol 0-7%) to provide N,N-dicyclopropyl-6-ethyl-1-methyl-4-(4-methylthiazol-2-ylamino)-1,6-dihydroimidazo[4,5-d]pyrrolo[2,3-b]pyridine-7-carboxamide (9 mg, 12% yield) as a white solid.

MS (CI) m/z 436.1 (M+H)

1H NMR (400 MHz, DMSO-d$_6$) δ ppm 10.70 (br s, 1H), 8.12 (s, 1H), 7.23 (s, 1H), 6.69 (s, 1H), 4.61 (q, 2H, J=7.19 Hz), 4.04 (s, 3H), 2.88-2.98 (m, 2H), 2.29 (s, 3H), 1.38 (t, 3H, J=7.15 Hz), 0.72-0.81 (m, 4H), 0.62-0.70 (m, 4H)

Example 3

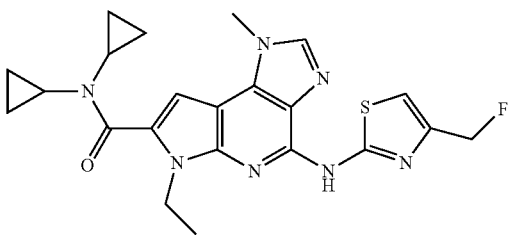 [SMILES: CCn1c(C(=O)N(C2CC2)C2CC2)cc2c3c(ncn3C)c(Nc3nc(CF)cs3)nc21]

N,N-dicyclopropyl-6-ethyl-4-(4-(fluoromethyl)thiazol-2-ylamino)-1-methyl-1,6-dihydroimidazo[4,5-d]pyrrolo[2,3-b]pyridine-7-carboxamide

3A Preparation of 1-bromo-3-fluoropropan-2-one

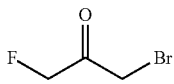

Bromine (0.36 ml, 7.02 mmol) was added dropwise to a solution of 1-fluoropropan-2-one (0.51 ml, 7.02 mmol) in carbon tetrachloride (25 ml). The solution was heated at 45° C. for 3 h. The reaction was cooled to room temperature and quenched with water. Upon extraction with dichloromethane (3×), the combined organic layers were dried over $Na_2SO_4$, filtered, and concentrated. Purification by silica gel chromatography (0-20% EtOAc/Hexanes) gave 1-bromo-3-fluoropropan-2-one as a yellow oil (118 mg, 65%).

1H NMR (400 MHz, CHLOROFORM-d) δ ppm 5.14 (s, 1 H) 5.02 (s, 1 H) 4.10 (d, J=2.86 Hz, 2 H).

3 Preparation of N,N-dicyclopropyl-6-ethyl-4-(4-(fluoromethyl)thiazol-2-ylamino)-1-methyl-1,6-dihydroimidazo[4,5-d]pyrrolo[2,3-b]pyridine-7-carboxamide Prepared from N,N-dicyclopropyl-6-ethyl-1-methyl-4-thioureido-1,6-dihydroimidazo[4,5-d]pyrrolo[2,3-b]pyridine-7-carboxamide (example 2B) and 1-bromo-3-fluoropropan-2-one (example 3A) using the same procedure for 2.

MS (ESI) rt=1.94 min, m/z 454 (M+H).

1H NMR (400 MHz, CHLOROFORM-d) δ ppm 9.34 (br. s., 1 H) 7.75 (s, 1 H) 6.96 (d, J=3.52 Hz, 1 H) 6.90 (s, 1 H) 5.27-5.53 (m, 2 H) 4.75 (q, J=7.12 Hz, 2 H) 3.98-4.11 (m, 3 H) 2.76-2.91 (m, 2 H) 1.54 (t, J=7.04 Hz, 3 H) 0.70-0.94 (m, 8 H).

Example 4

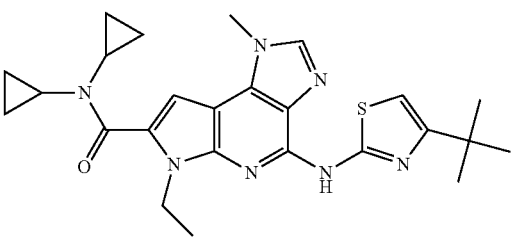 [SMILES: CCn1c(C(=O)N(C2CC2)C2CC2)cc2c3c(ncn3C)c(Nc3nc(C(C)(C)C)cs3)nc21]

4-(4-tert-butylthiazol-2-ylamino)-N,N-dicyclopropyl-6-ethyl-1-methyl-1,6-dihydroimidazo[4,5-d]pyrrolo[2,3-b]pyridine-7-carboxamide Prepared from N,N-dicyclopropyl-6-ethyl-1-methyl-4-thioureido-1,6-dihydroimidazo[4,5-d]pyrrolo[2,3-b]pyridine-7-carboxamide (example 2B) and 1-chloro-3,3-dimethylbutan-2-one using the same procedure as reported for 2.

MS (ESI) rt=1.99 min, m/z 478 (M+H).

1H NMR (400 MHz, CHLOROFORM-d) δ ppm 7.74 (s, 1 H) 6.90 (s, 1 H) 6.48 (s, 1 H) 4.74 (q, J=7.03 Hz, 1 H) 4.04 (s, 3 H) 2.77-2.90 (m, 2 H) 1.53 (t, J=7.03 Hz, 3 H) 1.37 (s, 9 H) 0.70-0.96 (m, 8 H).

Example 5

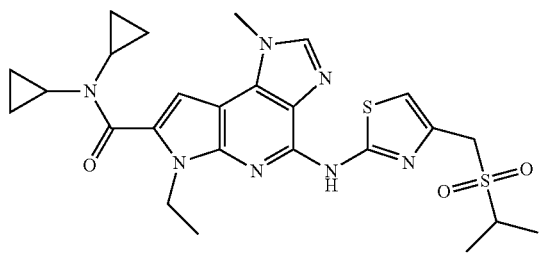 [SMILES: CCn1c(C(=O)N(C2CC2)C2CC2)cc2c3c(ncn3C)c(Nc3nc(CS(=O)(=O)C(C)C)cs3)nc21]

N,N-dicyclopropyl-6-ethyl-4-(4-(isopropylsulfonylmethyl)thiazol-2-ylamino)-1-methyl-1,6-dihydroimidazo[4,5-d]pyrrolo[2,3-b]pyridine-7-carboxamide

5A Preparation of 1-chloro-1-(isopropylsulfonyl)propan-2-one

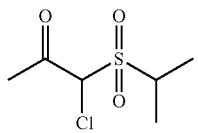

Sulfuryl chloride (0.248 mL, 3.05 mmol) was added dropwise to a solution of 1-(isopropylsulfonyl)propan-2-one (418 mg, 2.55 mmol) in 1:1 AcOH/DCM (16 ml) at 0° C. The reaction was stirred at rt for 4 h. The solvent was removed in vacuo, then diluted with dichloromethane. The organic layer was washed (2×) with saturated $NaHCO_3$ solution, dried over $Na_2SO_4$, filtered, and concentrated to leave 800 mg of a colorless oil. The material was used without further purification.

1H NMR (500 MHz, CHLOROFORM-d) δ ppm 5.19 (s, 1 H) 3.65 (dt, J=13.66, 6.90 Hz, 1 H) 2.56 (s, 3 H) 1.45 (dd, J=6.94, 3.05 Hz, 6 H).

5 Preparation of N,N-dicyclopropyl-6-ethyl-4-(4-(isopropylsulfonylmethyl)thiazol-2-ylamino)-1-methyl-1,6-dihydroimidazo[4,5-d]pyrrolo[2,3-b]pyridine-7-carboxamide Prepared from N,N-dicyclopropyl-6-ethyl-1-methyl-4-thioureido-1,6-dihydroimidazo[4,5-d]pyrrolo[2,3-b]pyridine-7-carboxamide (example 2B) and 1-chloro-1-(isopropylsulfonyl)propan-2-one (example 5ᵃ) using same procedure as reported for 2.

MS (ESI) rt=1.84 min, m/z 542 (M+H).

1H NMR (400 MHz, CHLOROFORM-d) δ ppm 7.82 (s, 1 H) 7.01 (s, 1 H) 6.90 (s, 1 H) 4.73 (q, J=7.04 Hz, 2 H) 4.35 (s, 2 H) 4.06 (s, 3 H) 3.36 (quin, J=6.88 Hz, 1 H) 2.79-2.91 (m, 2 H) 1.53 (t, J=7.04 Hz, 3 H) 1.43 (d, J=6.82 Hz, 6 H) 0.74-0.92 (m, 8 H).

Example 6

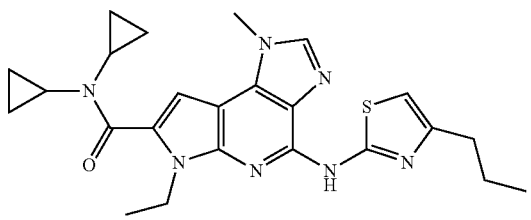 [SMILES: CCCc1csc(Nc2nc3c(cc(C(=O)N(C4CC4)C4CC4)n3CC)c3c2ncn3C)n1]

N,N-dicyclopropyl-6-ethyl-1-methyl-4-(4-propylthiazol-2-ylamino)-1,6-dihydroimidazo[4,5-d]pyrrolo[2,3-b]pyridine-7-carboxamide Prepared from N,N-dicyclopropyl-6-ethyl-1-methyl-4-thioureido-1,6-dihydroimidazo[4,5-d]pyrrolo[2,3-b]pyridine-7-carboxamide (example 2B) and 1-bromopentan-2-one using the same procedure as reported for 2.

MS (ESI) rt=1.94 min, m/z 464 (M+H).

1H NMR (400 MHz, CHLOROFORM-d) δ ppm 8.43-9.78 (m, 1 H) 7.71 (s, 1 H) 6.89 (s, 1 H) 6.48 (s, 1 H) 4.75 (q, J=7.04 Hz, 2 H) 4.04 (s, 3 H) 2.76-2.92 (m, 2 H) 2.68 (t, J=7.37 Hz, 2 H) 1.76 (dq, J=14.94, 7.42 Hz, 2 H) 1.53 (t, J=7.04 Hz, 3 H) 1.01 (t, J=7.26 Hz, 3 H) 0.69-0.94 (m, 8 H).

Example 7

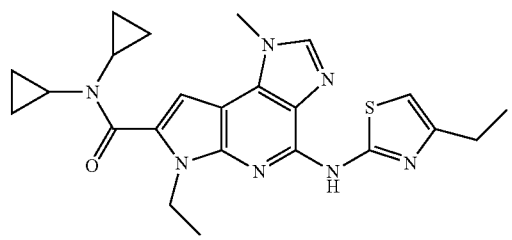 [SMILES: CCc1csc(Nc2nc3c(cc(C(=O)N(C4CC4)C4CC4)n3CC)c3c2ncn3C)n1]

N,N-dicyclopropyl-6-ethyl-4-(4-ethylthiazol-2-ylamino)-1-methyl-1,6-dihydroimidazo[4,5-d]pyrrolo[2,3-b]pyridine-7-carboxamide Prepared from N,N-dicyclopropyl-6-ethyl-1-methyl-4-thioureido-1,6-dihydroimidazo[4,5-d]pyrrolo[2,3-b]pyridine-7-carboxamide (example 2B) and 1-bromobutan-2-one using the same procedure as reported for 2.

MS (ESI) m/z 450 (M+H).

1H NMR (400 MHz, CHLOROFORM-d) δ ppm 7.71 (s, 1 H) 6.89 (s, 1 H) 6.49 (s, 1 H) 4.75 (q, J=7.03 Hz, 2 H) 4.04 (s, 3 H) 2.80-2.88 (m, 2 H) 2.75 (q, J=7.45 Hz, 1 H) 1.54 (t, J=7.15 Hz, 2 H) 1.33 (t, J=7.40 Hz, 2 H) 0.82 (br. s., 8 H).

Example 8

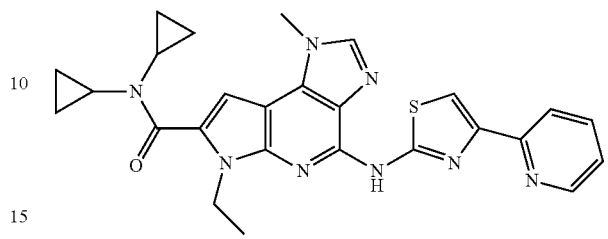

N,N-dicyclopropyl-6-ethyl-1-methyl-4-(4-(pyridin-2-yl)thiazol-2-ylamino)-1,6-dihydroimidazo[4,5-d]pyrrolo[2,3-b]pyridine-7-carboxamide A solution of 4-amino-N,N-dicyclopropyl-6-ethyl-1-methyl-1,6-dihydroimidazo[4,5-d]pyrrolo[2,3-b]pyridine-7-carboxamide (example 1J, 70 mg, 0.21 mmol) and benzoyl isothiocyanate (36 μl, 0.27 mmol) in acetone (1 ml) was stirred at room temperature for 1.5 h. The solvent was removed in vacuo, the residue was taken up in EtOH (1.5 ml), and $K_2CO_3$ (40 mg, 0.290 mmol) was added. The reaction was heated at 60° C. for 3 h. Upon cooling to room temperature, 2-bromo-1-(pyridin-2-yl)ethanone, hydrobromide (139.4 mg, 0.50 mmol) was added and the reaction heated at 80° C. for 24 h. The reaction mixture was cooled to room temperature and concentrated. The residue was purified by silica gel chromatography (0-7% MeOH/dichloromethane). Re-purification by preparative HPLC provided 10.2 mg (10% yield) of N,N-dicyclopropyl-6-ethyl-1-methyl-4-(4-(pyridin-2-yl)thiazol-2-ylamino)-1,6-dihydroimidazo[4,5-d]pyrrolo[2,3-b]pyridine-7-carboxamide as a brown solid.

MS (ESI) rt=1.78 min, m/z 499 (M+H).

1H NMR (DMSO-d6) δ ppm 10.9 (s, 1 H), 8.2 (bs, 1 H), 7.81 (d, 1 H), 7.75 (s, 1H), 3.92 (m, 4H), 3.77 (q, 2H, J=7.8 Hz), 2.52-2.81 (m, 7H).

Example 9

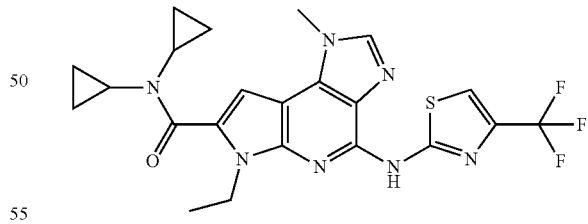

Preparation of N,N-dicyclopropyl-6-ethyl-1-methyl-4-(4-(trifluoromethyl)thiazol-2-ylamino)-1,6-dihydroimidazo[4,5-d]pyrrolo[2,3-b]pyridine-7-carboxamide This compound was prepared according to example 2 using 3-bromo-1,1,1-trifluoroacetone to provide N,N-dicyclopropyl-6-ethyl-1-methyl-4-(4-(trifluoromethyl) thiazol-2-ylamino)-1,6-dihydroimidazo[4,5-d]pyrrolo[2,3-b]pyridine-7-carboxamide.

MS (ESI) m/z 490.0 (M+H)

1H NMR (500 MHz, DMSO-$d_6$) δ ppm 11.71 (s, 1H), 8.16 (s, 1H), 7.86 (s, 1H), 7.27 (s, 1H), 4.63 (q, 2H), 4.05 (s, 3H), 2.89-2.98 (m, 2H), 1.40 (t, 3H, J=6.87 Hz), 0.74-0.80 (m, 4H), 0.64-0.71 (m, 4H)

Example 10

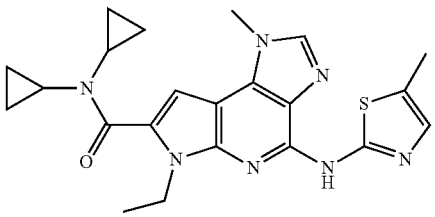 [SMILES: CCn1c(C(=O)N(C2CC2)C2CC2)cc2c3c(ncn3C)c(Nc3ncc(C)s3)nc21]

Preparation of N,N-dicyclopropyl-6-ethyl-1-methyl-4-(5-methylthiazol-2-ylamino)-1,6-dihydroimidazo[4,5-d]pyrrolo[2,3-b]pyridine-7-carboxamide 4-Amino-N,N-dicyclopropyl-6-ethyl-1-methyl-1,6-dihydroimidazo[4,5-d]pyrrolo[2,3-b]pyridine-7-carboxamide (example 1J, 86.3 mg, 0.255 mmol) was dissolved in acetone and benzoyl isothiocyanate (37.8 µL, 0.281 mmol) was added. The reaction was stirred at room temperature for 2 h. The solvent was removed in vacuo. The residue was taken up in ethanol (1500 µL) and $K_2CO_3$ (49.3 mg, 0.357 mmol) was added. The reaction mixture was warmed to 60° C. for 3 h. 2-Bromopropanal (45.4 mg, 0.332 mmol) was added. After 3 h, additional 2-bromopropanal (~100 mg) was added. Stirred at 60° C. for 16 h. Additional 2-bromopropanal was added and the reaction mixture was stirred at 60° C. 3 h. The ethanol was removed by concentration in vacuo. The crude residue was purified by flash chromatography using an Isco 12 g column eluting with 2-10% MeOH/$CH_2Cl_2$). Additional purification was accomplished via preparative HPLC. N,N-dicyclopropyl-6-ethyl-1-methyl-4-(5-methylthiazol-2-ylamino)-1,6-dihydroimidazo[4,5-d]pyrrolo[2,3-b]pyridine-7-carboxamide (20 mg, 17.47% yield) was isolated as a white solid.

MS (ESI) m/z 436.0 (M+H)

1H NMR (500 MHz, DMSO-$d_6$) δ ppm 10.56 (br s, 1H), 8.12 (s, 1H), 7.23 (s, 1H), 7.12 (s, 1H), 4.62 (q, 2H, J=6.78 Hz), 4.04 (s, 3H), 2.87-2.99 (m, 2H), 2.39 (s, 3H), 1.35-1.46 (m, 3H), 0.72-0.81 (m, 4H), 0.59-0.71 (m, 4H)

Example 11

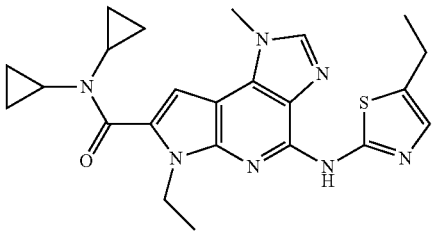 [SMILES: CCc1cnc(Nc2nc3c(cc(C(=O)N(C4CC4)C4CC4)n3CC)c3c2ncn3C)s1]

N,N-dicyclopropyl-6-ethyl-4-(5-ethylthiazol-2-ylamino)-1-methyl-1,6-dihydroimidazo[4,5-d]pyrrolo[2,3-b]pyridine-7-carboxamide Prepared from 2-bromobutanal and 4-Amino-N,N-dicyclopropyl-6-ethyl-1-methyl-1,6-dihydroimidazo[4,5-d]pyrrolo[2,3-b]pyridine-7-carboxamide (example 1J) using the same procedure as that of example 8.

MS (ESI) rt=1.86 min, m/z 450 (M+H).

1H NMR (500 MHz, CHLOROFORM-d) δ ppm 8.91-9.22 (m, 1 H) 7.71 (s, 1 H) 7.14 (s, 1 H) 6.89 (s, 1 H) 4.75 (q, J=6.94 Hz, 2 H) 4.05 (s, 3 H) 2.80-2.89 (m, 4 H) 1.55 (t, J=5.00 Hz, 3 H) 1.37 (t, J=7.49 Hz, 3 H) 0.73-0.92 (m, 8 H).

Example 12

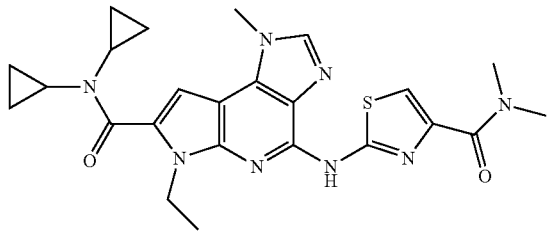 [SMILES: CCn1c(C(=O)N(C2CC2)C2CC2)cc2c3c(ncn3C)c(Nc3nc(C(=O)N(C)C)cs3)nc21]

2-(7-(dicyclopropylcarbamoyl)-6-ethyl-1-methyl-1,6-dihydroimidazo[4,5-d]pyrrolo[2,3-b]pyridin-4-ylamino)-N,N-dimethylthiazole-4-carboxamide 12A Preparation of 2-(7-(dicyclopropylcarbamoyl)-6-ethyl-1-methyl-1,6-dihydroimidazo[4,5-d]pyrrolo[2,3-b]pyridin-4-ylamino)thiazole-4-carboxylic acid

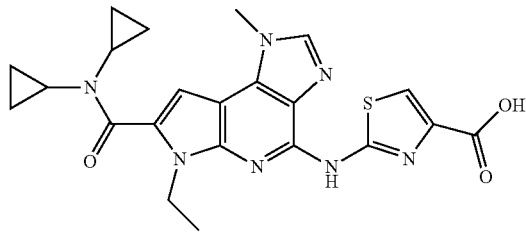 [SMILES: CCn1c(C(=O)N(C2CC2)C2CC2)cc2c3c(ncn3C)c(Nc3nc(C(=O)O)cs3)nc21]

4-Amino-N,N-dicyclopropyl-6-ethyl-1-methyl-1,6-dihydroimidazo[4,5-d]pyrrolo[2,3-b]pyridine-7-carboxamide (1J, 300 mg, 0.89 mmol) and benzoyl isothiocyanate (0.16 ml, 1.15 mmol) in acetone (4 ml) were stirred at rt for 1.5 h. The solvent was removed in vacuo and the residue taken up in EtOH (6 ml). $K_2CO_3$ (172 mg, 1.241 mmol) was added and the reaction heated at 60° C. for 3 h. The reaction was cooled to rt and ethyl 3-bromo-2-oxopropanoate (692 mg, 3.55 mmol) was added. The reaction was heated at 70° C. overnight. Upon completion of the cyclization step, 1N NaOH (6.3 ml, 6.30 mmol) was added to the reaction mixture and heated at 60° C. for 4 h. The reaction was cooled to room temperature and the solvent removed in vacuo. The remaining aqueous solution was acidified to pH 1 and the precipitate removed by vacuum filtration, washing with water, EtOAc, and then dichloromethane to afford 2-(7-(dicyclopropylcarbamoyl)-6-ethyl-1-methyl-1,6-dihydroimidazo[4,5-d]pyrrolo[2,3-b]pyridine-4-ylamino)thiazole-4-carboxylic acid (325 mg, 79% yield) as brown solid.

MS (ESI) rt=1.85 min, m/z 466 (M+H).

1H NMR (400 MHz, DMSO-d$_6$) δ ppm 8.16 (s, 1 H) 7.94 (s, 1 H) 7.26 (s, 1 H) 4.63 (q, J=6.94 Hz, 2 H) 4.05 (s, 3 H) 3.36 (br. S., 1 H) 2.89-2.99 (m, 2 H) 1.40 (t, J=7.03 Hz, 3 H) 0.61-0.83 (m, 8 H).

12 Preparation of 2-(7-(dicyclopropylcarbamoyl)-6-ethyl-1-methyl-1,6-dihydroimidazo[4,5-d]pyrrolo[2,3-b]pyridin-4-ylamino)-N,N-dimethylthiazole-4-carboxamide

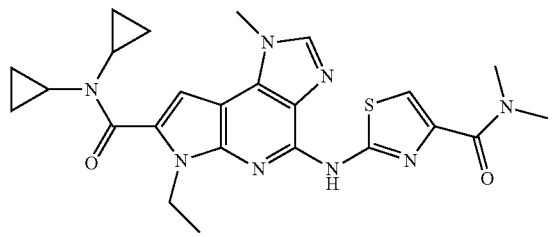 [SMILES: CCn1c(C(=O)N(C2CC2)C2CC2)cc2c3c(ncn3C)c(Nc3nc(C(=O)N(C)C)cs3)nc21]

To 2-(7-(dicyclopropylcarbamoyl)-6-ethyl-1-methyl-1,6-dihydroimidazo[4,5-d]pyrrolo[2,3-b]pyridin-4-ylamino)thiazole-4-carboxylic acid (example 12A, 44 mg, 0.095 mmol) in DMF (2 ml) was added HATU (108 mg, 0.284 mmol), DIPEA (0.066 mL, 0.378 mmol), and dimethylamine (0.013 mL, 0.189 mmol). The reaction was stirred at rt for 3 h, then the solvent was removed in vacuo. The residue was purified by preparative HPLC to give 2-(7-(dicyclopropylcarbamoyl)-6-ethyl-1-methyl-1,6-dihydroimidazo[4,5-d]pyrrolo[2,3-b]pyridine-4-ylamino)-N,N-dimethylthiazole-4-carboxamide (10 mg, 21% yield) as a brown solid.

MS (ESI) m/z 493 (M+H)

1H NMR (400 MHz, CHLOROFORM-d) δ ppm 9.45 (br. S., 1 H) 7.81 (s, 1 H) 7.43 (s, 1 H) 6.90 (s, 1 H) 4.74 (q, J=7.03 Hz, 2 H) 4.05 (s, 3 H) 3.31 (br. S., 3 H) 3.13 (br. S., 3 H) 2.75-2.90 (m, 2 H) 1.54 (t, J=7.15 Hz, 3 H) 0.65-0.96 (m, 8 H).

Examples 13-17 were prepared using the procedure as described for example 12

Example 13

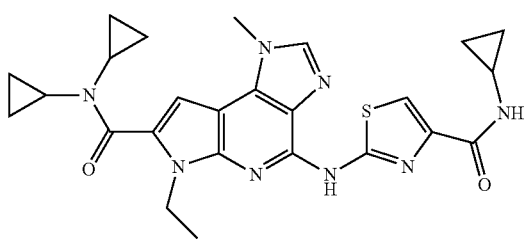 [SMILES: CCn1c(C(=O)N(C2CC2)C2CC2)cc2c3c(ncn3C)c(Nc3nc(C(=O)NC4CC4)cs3)nc21]

N-cyclopropyl-2-(7-(dicyclopropylcarbamoyl)-6-ethyl-1-methyl-1,6-dihydroimidazo[4,5-d]pyrrolo[2,3-b]pyridin-4-ylamino)thiazole-4-carboxamide MS (ESI) rt=1.99 min, m/z 505 (M+H).

1H NMR (400 MHz, MeOD) δ ppm 8.07 (s, 1 H) 7.74 (s, 1 H) 7.26 (s, 1 H) 4.73 (q, J=7.03 Hz, 1 H) 4.13 (s, 3 H) 2.94-3.04 (m, 2 H) 2.85-2.93 (m, 1 H) 1.51 (t, J=7.03 Hz, 2 H) 0.67-0.95 (m, 12 H).

Example 14

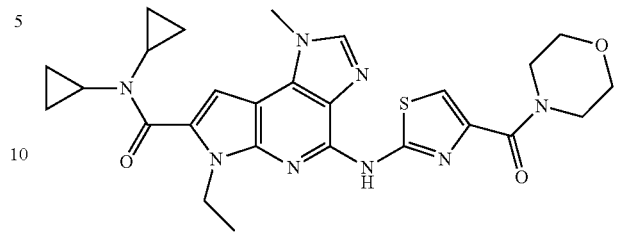

N,N-dicyclopropyl-6-ethyl-1-methyl-4-(4-(morpholine-4-carbonyl)thiazol-2-ylamino)-1,6-dihydroimidazo[4,5-d]pyrrolo[2,3-b]pyridine-7-carboxamide MS (ESI) rt=1.87 min, m/z 535 (M+H).

1H NMR (400 MHz, CHLOROFORM-d) δ ppm 9.21 (br. s., 1 H) 7.76 (s, 1 H) 7.56 (s, 1 H) 6.81-6.94 (m, 1 H) 4.74 (q, J=7.11 Hz, 2 H) 4.07 (s, 3 H) 3.79 (br. s., 4 H) 3.50 (d, J=4.52 Hz, 2 H) 2.74-2.90 (m, 2 H) 1.60 (s, 2 H) 1.54 (t, J=7.03 Hz, 3 H) 0.70-0.94 (m, 8 H).

Example 15

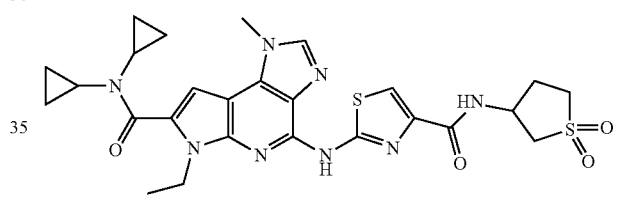

N,N-dicyclopropyl-4-((4-((1,1-dioxidotetrahydro-3-thiophenyl)carbamoyl)-1,3-thiazol-2-yl)amino)-6-ethyl-1-methyl-1,6-dihydroimidazo[4,5-d]pyrrolo[2,3-b]pyridine-7-carboxamide MS (ESI) rt=1.88 min, m/z 583 (M+H).

1H NMR (400 MHz, CHLOROFORM-d) δ ppm 9.31 (br. s., 1 H) 7.77 (s, 1 H) 7.69-7.75 (m, 1 H) 6.91 (s, 1 H) 4.85-4.99 (m, 1 H) 4.64-4.81 (m, 2 H) 4.07 (s, 3 H) 3.45-3.61 (m, 2 H) 3.35 (br. s., 1 H) 3.19 (dt, J=13.36, 8.12 Hz, 2 H) 2.75-2.91 (m, 2 H) 2.57-2.72 (m, 1 H) 2.42 (ddd, J=14.49, 7.53, 7.34 Hz, 1 H) 1.54 (t, J=6.90 Hz, 3 H) 0.69-0.94 (m, 8 H)

Example 16

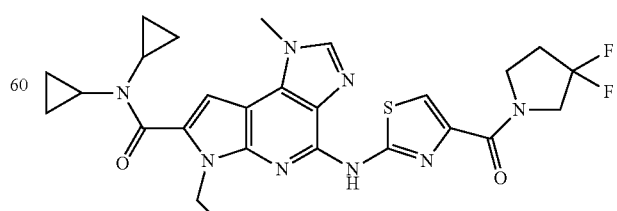

N,N-dicyclopropyl-4-(4-(3,3-difluoropyrrolidine-1-carbonyl)thiazol-2-ylamino)-6-ethyl-1-methyl-1,6-dihydroimidazo[4,5-d]pyrrolo[2,3-b]pyridine-7-carboxamide MS (ESI) rt=2.05 min, m/z 555 (M+H).
1H NMR (400 MHz, MeOD) δ ppm 8.00 (s, 1 H) 7.73 (s, 1 H) 7.70 (s, 1 H) 7.19 (s, 1 H) 4.68 (q, J=7.03 Hz, 2 H) 4.51 (t, J=12.80 Hz, 1 H) 4.34 (t, J=7.40 Hz, 1 H) 4.06 (s, 3 H) 3.96 (t, J=13.18 Hz, 1 H) 3.86 (t, J=7.65 Hz, 1 H) 2.87-3.02 (m, 2 H) 2.34-2.59 (m, 2 H) 1.45 (t, J=6.90 Hz, 3 H) 0.72-0.95 (m, 8 H).

Example 17

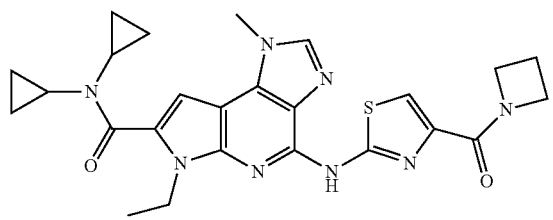 [SMILES: CCn1c(C(=O)N(C2CC2)C2CC2)cc2c3c(ncn3C)c(Nc3nc(C(=O)N4CCC4)cs3)nc21]

(4-(azetidine-1-carbonyl)thiazol-2-ylamino)-N,N-dicyclopropyl-6-ethyl-1-methyl-1,6-dihydroimidazo[4,5-d]pyrrolo[2,3-b]pyridine-7-carboxamide MS (ESI) rt=1.95 min, m/z 505 (M+H).
1H NMR (400 MHz, MeOD) δ ppm 8.03 (s, 1 H) 7.70 (s, 1 H) 7.21 (s, 1 H) 4.78 (t, J=7.53 Hz, 2 H) 4.69 (q, J=7.03 Hz, 2 H) 4.19 (t, J=7.78 Hz, 2 H) 4.08 (s, 3 H) 2.95 (ddd, J=7.22, 3.45, 3.14 Hz, 2 H) 2.27-2.48 (m, 2 H) 1.47 (t, J=7.03 Hz, 3 H) 0.69-0.93 (m, 8 H).

Example 18

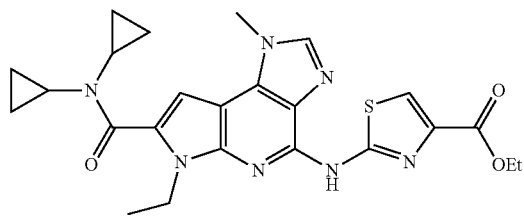 [SMILES: CCOC(=O)c1csc(Nc2nc3c(cc(C(=O)N(C4CC4)C4CC4)n3CC)c3c2ncn3C)n1]

Ethyl 2-(7-(dicyclopropylcarbamoyl)-6-ethyl-1-methyl-1,6-dihydroimidazo[4,5-d]pyrrolo[2,3-b]pyridin-4-ylamino)thiazole-4-carboxylate This compound was prepared according to example 2 using ethyl bromopyruvate and N,N-dicyclopropyl-6-ethyl-1-methyl-4-thioureido-1,6-dihydroimidazo[4,5-d]pyrrolo[2,3-b]pyridine-7-carboxamide (example 2B) to yield ethyl 2-(7-(dicyclopropylcarbamoyl)-6-ethyl-1-methyl-1,6-dihydroimidazo[4,5-d]pyrrolo[2,3-b]pyridin-4-ylamino)thiazole-4-carboxylate as yellow solid.
MS (ESI) m/z 494.1 (M+H)
1H NMR (500 MHz, DMSO-$d_6$) δ ppm 11.42 (br s, 1H), 8.14 (s, 1H), 8.00 (s, 1H), 7.25 (s, 1H), 4.62 (q, 2H), 4.30 (q, 2H, J=7.15 Hz), 4.05 (s, 3H), 2.89-2.97 (m, 2H), 1.39 (t, 3H, J=7.01 Hz), 1.32 (t, 3H, J=7.15 Hz), 0.74-0.80 (m, 4H), 0.64-0.70 (m, 4H)

Example 19

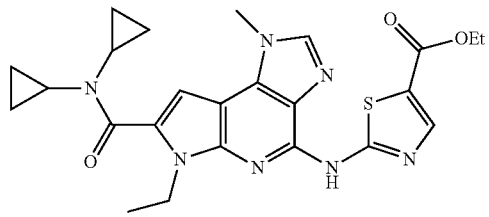 [SMILES: CCOC(=O)c1cnc(Nc2nc3c(cc(C(=O)N(C4CC4)C4CC4)n3CC)c3c2ncn3C)s1]

Ethyl 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylate This compound was prepared according to example 2 using ethyl 2-chloro-2-formylacetate and N,N-dicyclopropyl-6-ethyl-1-methyl-4-thioureido-1,6-dihydroimidazo[4,5-d]pyrrolo[2,3-b]pyridine-7-carboxamide (example 2B) to provide ethyl 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylate (18.5 mg, 17% yield) as a pale yellow solid.
MS (ESI) m/z 494.0 (M+H)
1H NMR (400 MHz, DMSO-$d_6$) δ ppm 11.95 (s, 1H), 8.20 (s, 1H), 8.14 (s, 1H), 7.28 (s, 1H), 4.63 (q, 2H, J=7.19 Hz), 4.28 (q, 2H, J=7.19 Hz), 4.06 (s, 3H), 2.88-3.00 (m, 2H), 1.44 (t, 3H, J=7.03 Hz), 1.32 (t, 3H, J=7.15 Hz), 0.73-0.81 (m, 4H), 0.63-0.70 (m, 4H)

Example 20

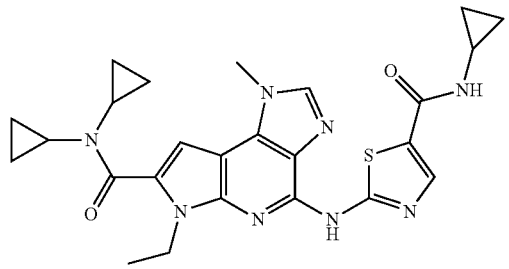 [SMILES: CCn1c(C(=O)N(C2CC2)C2CC2)cc2c3c(ncn3C)c(Nc3ncc(C(=O)NC4CC4)s3)nc21]

N-cyclopropyl-2-(7-(dicyclopropylcarbamoyl)-6-ethyl-1-methyl-1,6-dihydroimidazo[4,5-d]pyrrolo[2,3-b]pyridin-4-ylamino)thiazole-5-carboxamide 20A Preparation of 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid

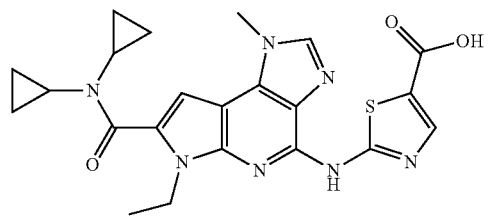 [SMILES: CCn1c(C(=O)N(C2CC2)C2CC2)cc2c3c(ncn3C)c(Nc3ncc(C(=O)O)s3)nc21]

To a solution of ethyl 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylate (example 19, 14.6 mg, 0.030 mmol) in EtOH (296 μL) was added 1 N NaOH aqueous solution (296 μL). The reaction mixture was stirred at rt 3 h and stirred at 50° C. 18 h. After cooling to room temperature, ethanol was removed by concentration in vacuo. The residue was acidified with 1 N HCl and the solid product was collected by filtration. 2-(7-(Dicyclopropylcarbamoyl)-6-ethyl-1-methyl-1,6-dihydroimidazo[4,5-d]pyrrolo[2,3-b]pyridin-4-ylamino)thiazole-5-carboxylic acid was isolated as a pale yellow solid which was used crude in the next reaction.

MS (ESI) m/z 465.9 (M+H)

20 Preparation of N-cyclopropyl-2-(7-(dicyclopropylcarbamoyl)-6-ethyl-1-methyl-1,6-dihydroimidazo[4,5-d]pyrrolo[2,3-b]pyridin-4-ylamino)thiazole-5-carboxamide To a mixture of 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid (example 20A, 13.97 mg, 0.030 mmol) in DMF (300 μL) was added cyclopropylamine (4.16 μL, 0.060 mmol), HATU (14.83 mg, 0.039 mmol), and Hünig's Base (15.72 μL, 0.090 mmol). The reaction mixture was stirred at rt 1 h and concentrated in vacuo. The residue was taken up in MeOH and purified by preparative HPLC. N-Cyclopropyl-2-(7-(dicyclopropylcarbamoyl)-6-ethyl-1-methyl-1,6-dihydroimidazo[4,5-d]pyrrolo[2,3-b]pyridin-4-ylamino)thiazole-5-carboxamide (3 mg, 19.82% yield) was isolated as a white solid.

MS (ESI) m/z 505.0 (M+H)

1H NMR (400 MHz, DMSO-$d_6$) δ ppm 8.36 (br s, 1H), 8.15 (s, 1H), 8.02 (s, 1H), 7.25 (s, 1H), 4.63 (q, 2H, J=7.11 Hz), 4.05 (s, 3H), 2.89-3.00 (m, 2H), 2.76 (tq, 1H, J=7.25, 3.70 Hz), 1.41 (t, 3H, J=7.03 Hz), 0.74-0.81 (m, 4H), 0.64-0.72 (m, 6H), 0.51-0.59 (m, 2H)

Example 21

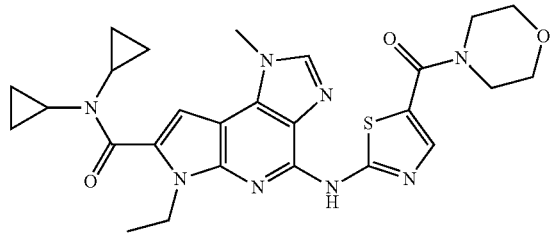 [SMILES: CCn1c(C(=O)N(C2CC2)C2CC2)cc2c3c(ncn3C)c(Nc3ncc(C(=O)N4CCOCC4)s3)nc21]

N,N-dicyclopropyl-6-ethyl-1-methyl-4-(5-(morpholine-4-carbonyl)thiazol-2-ylamino)-1,6-dihydroimidazo[4,5-d]pyrrolo[2,3-b]pyridine-7-carboxamide This compound was prepared according to Example 20 using morpholine and 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid (example 20A) to provide N,N-dicyclopropyl-6-ethyl-1-methyl-4-(5-(morpholine-4-carbonyl)thiazol-2-ylamino)-1,6-dihydroimidazo[4,5-d]pyrrolo[2,3-b]pyridine-7-carboxamide as a white solid.

MS (ESI) m/z 535.1 (M+H)

1H NMR (400 MHz, MeOD) δ ppm 8.08 (s, 1H), 7.79-7.93 (m, 1H), 7.26 (s, 1H), 4.74 (q, 2H, J=7.28 Hz), 4.12 (s, 3H), 3.81-3.88 (m, 2H), 3.72-3.80 (m, 2H), 2.91-3.02 (m, 2H), 1.52 (t, 3H, J=7.15 Hz), 0.83-0.93 (m, 4H), 0.72-0.84 (m, 4H)

Example 22

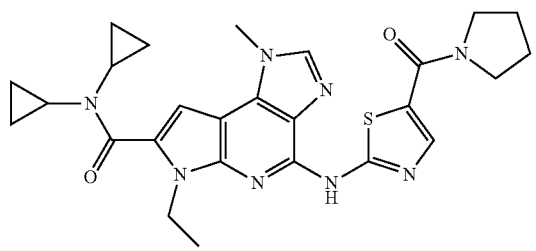 [SMILES: CCn1c(C(=O)N(C2CC2)C2CC2)cc2c3c(ncn3C)c(Nc3ncc(C(=O)N4CCCC4)s3)nc21]

N,N-dicyclopropyl-6-ethyl-1-methyl-4-(5-(pyrrolidine-1-carbonyl)thiazol-2-ylamino)-1,6-dihydroimidazo[4,5-d]pyrrolo[2,3-b]pyridine-7-carboxamide This compound was prepared according to Example 20 using pyrrolidine and 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid (example 20A) to provide N,N-dicyclopropyl-6-ethyl-1-methyl-4-(5-(pyrrolidine-1-carbonyl)thiazol-2-ylamino)-1,6-dihydroimidazo[4,5-d]pyrrolo[2,3-b]pyridine-7-carboxamide MS (ESI) m/z 519.1 (M+H).

1H NMR (400 MHz, METHANOL-$d_4$) δ 8.58 (s, 1H), 7.97 (s, 1H), 7.28 (s, 1H), 4.71 (q, J=6.7 Hz, 2H), 4.20 (s, 3H), 3.87 (t, J=6.5 Hz, 2H), 3.67 (t, J=6.7 Hz, 2H), 2.97-3.05 (m, 2H), 2.10-2.19 (m, 2H), 1.98-2.07 (m, 2H), 1.51 (t, J=7.2 Hz, 3H), 0.88-0.95 (m, 4H), 0.80-0.86 (m, 4H)

Example 23

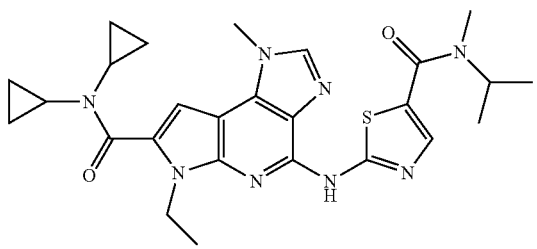 [SMILES: CCn1c(C(=O)N(C2CC2)C2CC2)cc2c3c(ncn3C)c(Nc3ncc(C(=O)N(C)C(C)C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N-isopropyl-N-methylthiazole-5-carboxamide This compound was prepared according to Example 20 using N-methylpropan-2-amine and 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid (example 20A) to provide 2-(7-(dicyclopropylcarbamoyl)-6-ethyl-1-methyl-1,6-dihydroimidazo[4,5-d]pyrrolo[2,3-b]pyridin-4-ylamino)-N-isopropyl-N-methylthiazole-5-carboxamide MS (ESI) m/z 521.1 (M+H).

1H NMR (400 MHz, METHANOL-$d_4$) δ: 8.68 (s, 1H), 7.87 (s, 1H), 7.32 (s, 1H), 4.74 (q, J=7.0 Hz, 2H), 4.24 (s, 3H), 3.18 (br. s., 3H), 2.99-3.06 (m, 2H), 1.53 (t, J=7.0 Hz, 3H), 1.35 (d, J=6.8 Hz, 6H), 0.89-0.96 (m, 4H), 0.81-0.88 (m, 4H)

Example 24

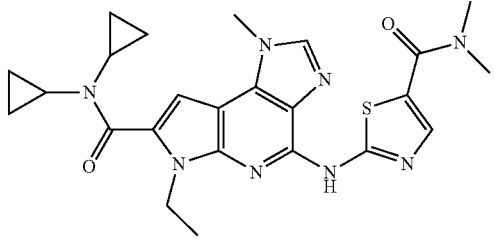 [SMILES: CCn1c(C(=O)N(C2CC2)C2CC2)cc2c3c(ncn3C)c(Nc3ncc(C(=O)N(C)C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N,N-dimethylthiazole-5-carboxamide This compound was prepared according to Example 20 using N,N-dimethylamine and 2-(7-(dicyclopropylcarbamoyl)-6-ethyl-1-methyl-1,6-dihydroimidazo[4,5-d]pyrrolo[2,3-b]pyridin-4-ylamino)thiazole-5-carboxylic acid (example 20A) to give 2-(7-(dicyclopropylcarbamoyl)-6-ethyl-1-methyl-1,6-dihydroimidazo[4,5-d]pyrrolo[2,3-b]pyridin-4-ylamino)-N,N-dimethylthiazole-5-carboxamide.

MS (ESI) m/z 493.1 (M+H).

$^1$H NMR (400 MHz, METHANOL-$d_4$) δ: 8.56 (s, 1H), 7.91 (s, 1H), 7.31 (s, 1H), 4.72 (q, J=7.0 Hz, 1H), 4.22 (s, 3H), 3.15-3.45 (br. S, 6H), 2.97-3.05 (m, 2H), 2.91 (s, 1H), 1.54 (t, J=7.0 Hz, 3H), 0.88-0.95 (m, 4H), 0.80-0.86 (m, 4H)

Example 25

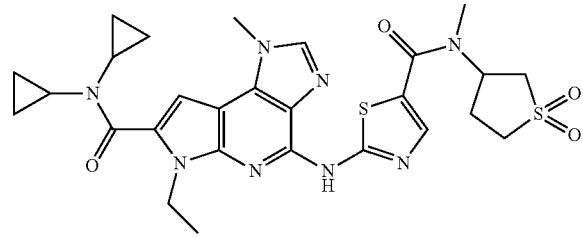 [SMILES: CCn1c(C(=O)N(C2CC2)C2CC2)cc2c3c(ncn3C)c(Nc3ncc(C(=O)N(C)C4CCS(=O)(=O)C4)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N-(1,1-Dioxo-tetrahydrothiophen-3-yl)-N-methylthiazole-5-carboxamide This compound was prepared according to example 20
MS (ESI) m/z 597.0 (M+H).

$^1$H NMR (400 MHz, METHANOL-$d_4$) δ: 8.74 (s, 1H), 7.99 (s, 1H), 7.37 (s, 1H), 5.34-5.45 (m, 1H), 4.78 (q, J=6.9 Hz, 2H), 4.28 (s, 3H), 4.05 (s, 3H), 3.49-3.59 (m, 1H), 3.22-3.33 (m, 1H), 3.00-3.10 (m, 2H), 2.94 (s, 1H), 2.47-2.66 (m, 2H), 1.57 (t, J=6.9 Hz, 3H), 1.34-1.45 (M, 1H), 0.91-0.99 (m, J=6.5 Hz, 4H), 0.83-0.90 (m, 4H)

Example 26

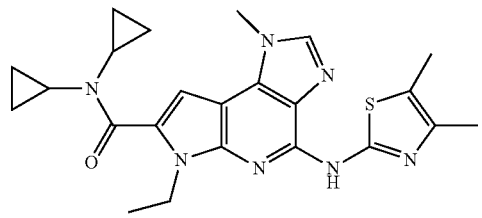 [SMILES: CCn1c(C(=O)N(C2CC2)C2CC2)cc2c3c(ncn3C)c(Nc3nc(C)c(C)s3)nc21]

N,N-dicyclopropyl-4-(4,5-dimethylthiazol-2-ylamino)-6-ethyl-1-methyl-1,6-dihydroimidazo[4,5-d]pyrrolo[2,3-b]pyridine-7-carboxamide This compound was prepared according to example 2 using 3-bromo-2-butanone (0.034 mL, 0.323 mmol) to provide N,N-dicyclopropyl-4-(4,5-dimethylthiazol-2-ylamino)-6-ethyl-1-methyl-1,6-dihydroimidazo[4,5-d]pyrrolo[2,3-b]pyridine-7-carboxamide (59.17 mg, 44.3% yield) as a pale yellow solid.

MS (ESI) m/z 450.1 (M+H)

1H NMR (400 MHz, DMSO-$d_6$) δ ppm 8.15 (s, 1H), 7.23 (s, 1H), 4.61 (q, 2H, J=7.03 Hz), 4.04 (s, 3H), 2.88-2.98 (m, 2H), 2.29 (s, 3H), 2.19 (s, 3H), 1.38 (t, 3H, J=7.03 Hz), 0.73-0.80 (m, 4H), 0.62-0.71 (m, 4H)

Example 27

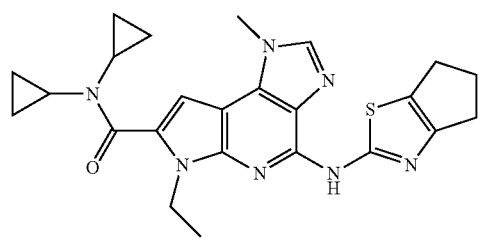 [SMILES: CCn1c(C(=O)N(C2CC2)C2CC2)cc2c3c(ncn3C)c(Nc3nc4c(s3)CCC4)nc21]

N,N-dicyclopropyl-4-(5,6-dihydro-4H-cyclopenta[d]thiazol-2-ylamino)-6-ethyl-1-methyl-1,6-dihydroimidazo[4,5-d]pyrrolo[2,3-b]pyridine-7-carboxamide Prepared using similar procedure as that of example 2
MS (ESI) rt=1.95 min, m/z 462 (M+H).

1H NMR (500 MHz, MeOD) δ ppm 8.12 (s, 1 H) 7.22 (s, 1 H) 4.68 (q, J=7.12 Hz, 2 H) 4.10 (s, 3 H) 2.86-3.02 (m, 4 H) 2.80 (t, J=7.07 Hz, 2 H) 2.43-2.61 (m, 2 H) 1.46 (t, J=7.07 Hz, 3 H) 0.70-0.90 (m, 8 H).

Example 28

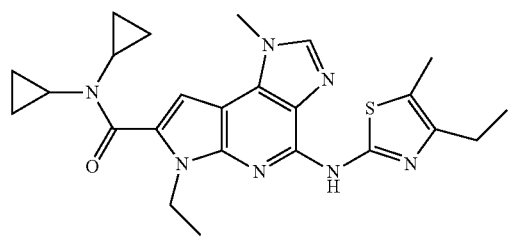 [SMILES: CCc1nc(Nc2nc3c(cc(C(=O)N(C4CC4)C4CC4)n3CC)c3c2ncn3C)sc1C]

N,N-dicyclopropyl-6-ethyl-4-(4-ethyl-5-methylthiazol-2-ylamino)-1-methyl-1,6-dihydroimidazo[4,5-d]pyrrolo[2,3-b]pyridine-7-carboxamide 28A Preparation of 2-bromopentan-3-one

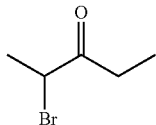

Prepared according to the procedure described in *Chem. Comm.* 2004, 470-471.

28 Preparation of N,N-dicyclopropyl-6-ethyl-4-(4-ethyl-5-methylthiazol-2-ylamino)-1-methyl-1,6-dihydroimidazo[4,5-d]pyrrolo[2,3-b]pyridine-7-carboxamide Prepared from example 26A using similar procedure as that of example 2

MS (ESI) m/z 464 (M+H).

1H NMR (400 MHz, CHLOROFORM-d) δ ppm 8.81-9.19 (m, 1 H) 7.69 (s, 1 H) 6.89 (s, 1 H) 4.75 (q, J=7.12 Hz, 2 H) 4.03 (s, 3 H) 2.78-2.93 (m, 2 H) 2.63 (q, J=7.48 Hz, 2 H) 2.37 (s, 3 H) 1.53 (t, J=7.04 Hz, 3 H) 1.26 (t, J=7.48 Hz, 3 H) 0.73-0.95 (m, 8 H).

Example 29

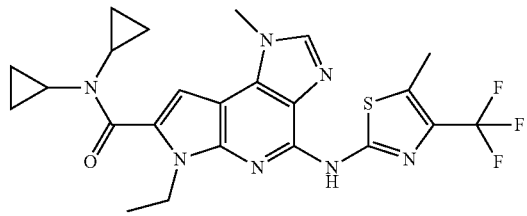 [SMILES: CCn1c(C(=O)N(C2CC2)C2CC2)cc2c3c(ncn3C)c(Nc3nc(C(F)(F)F)c(C)s3)nc21]

Preparation of N,N-dicyclopropyl-6-ethyl-1-methyl-4-(5-methyl-4-(trifluoromethyl)thiazol-2-ylamino)-1,6-dihydroimidazo[4,5-d]pyrrolo[2,3-b]pyridine-7-carboxamide This compound was prepared according to example 2 using 3-bromo-1,1,1-trifluorobutan-2-one to provide N,N-dicyclopropyl-6-ethyl-1-methyl-4-(5-methyl-4-(trifluoromethyl)thiazol-2-ylamino)-1,6-dihydroimidazo[4,5-d]pyrrolo[2,3-b]pyridine-7-carboxamide as a white solid.

MS (ESI) m/z 504.0 (M+H)

1H NMR (500 MHz, DMSO-d$_6$) δ ppm 8.14 (s, 1H), 7.25 (s, 1H), 4.62 (q, 2H, J=6.97 Hz), 4.04 (s, 3H), 2.89-2.98 (m, 2H), 1.40 (t, 3H, J=6.87 Hz), 0.73-0.80 (m, 4H), 0.65-0.71 (m, 4H)

Example 30

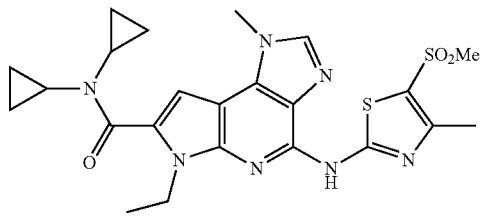 [SMILES: CCn1c(C(=O)N(C2CC2)C2CC2)cc2c3c(ncn3C)c(Nc3nc(C)c(S(C)(=O)=O)s3)nc21]

Preparation of N,N-dicyclopropyl-6-ethyl-1-methyl-4-(4-methyl-5-(methylsulfonyl)thiazol-2-ylamino)-1,6-dihydroimidazo[4,5-d]pyrrolo[2,3-b]pyridine-7-carboxamide 30A Preparation of 1-bromo-1-(methylsulfonyl)propan-2-one

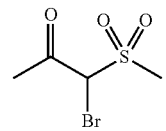

To a solution of methanesulphonylacetone (0.5 g, 3.67 mmol) in AcOH (7.34 mL) and dichloromethane (11.02 mL) in a round bottom flask was added bromine (0.189 mL, 3.67 mmol) dropwise. The reaction mixture was stirred at rt 90 min. Solvent was removed in vacuo. The residue was taken up in ether and washed with saturated aqueous sodium bicarbonate (2×). The organics were concentrated in vacuo. 1-Bromo-1-(methylsulfonyl)propan-2-one (0.332 g, 42% yield) was isolated as an oil.

MS (CI) m/z 215.0 (M+H)

30 Preparation of N,N-dicyclopropyl-6-ethyl-1-methyl-4-(4-methyl-5-(methylsulfonyl)thiazol-2-ylamino)-1,6-dihydroimidazo[4,5-d]pyrrolo[2,3-b]pyridine-7-carboxamide This compound was prepared according to example 1 using 1-bromo-1-(methylsulfonyl)propan-2-one (28A, 32.5 mg, 0.151 mmol) to provide N,N-dicyclopropyl-6-ethyl-1-methyl-4-(4-methyl-5-(methylsulfonyl)thiazol-2-ylamino)-1,6-dihydroimidazo[4,5-d]pyrrolo[2,3-b]pyridine-7-carboxamide (12.5 mg, 0.023 mmol, 30.6% yield) as an off-white solid.

MS (ESI) m/z 514.1 (M+H)

1H NMR (400 MHz, DMSO-d$_6$) δ ppm 12.00 (br s, 1H), 8.18 (s, 1H), 7.27 (s, 1H), 4.59 (q, 2H, J=6.78 Hz), 4.06 (s, 3H), 3.29 (s, 3H), 2.88-2.98 (m, 2H), 2.53 (s, 3H), 1.41 (t, 3H, J=6.90 Hz), 0.72-0.81 (m, 4H), 0.62-0.71 (m, 4H)

Example 31

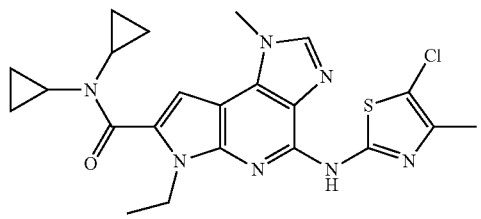 [SMILES: CCn1c(C(=O)N(C2CC2)C2CC2)cc2c3c(ncn3C)c(Nc3nc(C)c(Cl)s3)nc21]

Preparation of 4-(5-chloro-4-methylthiazol-2-ylamino)-N,N-dicyclopropyl-6-ethyl-1-methyl-1,6-dihydroimidazo[4,5-d]pyrrolo[2,3-b]pyridine-7-carboxamide This compound was prepared according to example 2 using 1,1-dichloropropan-2-one (14.26 μL, 0.147 mmol) to provide 4-(5-chloro-4-methylthiazol-2-ylamino)-N,N-dicyclopropyl-6-ethyl-1-methyl-1,6-dihydroimidazo[4,5-d]pyrrolo[2,3-b]pyridine-7-carboxamide (4.35 mg, 18.9% yield) as a pale green solid.

MS (ESI) m/z 470.1 (M+H)

1H NMR (400 MHz, DMSO-$d_6$) δ ppm 11.34 (s, 1H), 8.14 (s, 1H), 7.25 (s, 1H), 4.58 (q, 2H, J=7.28 Hz), 4.04 (s, 3H), 2.88-2.98 (m, 2H), 2.25 (s, 3H), 1.40 (t, 3H, J=6.90 Hz), 0.73-0.81 (m, 4H), 0.63-0.70 (m, 4H)

Example 32

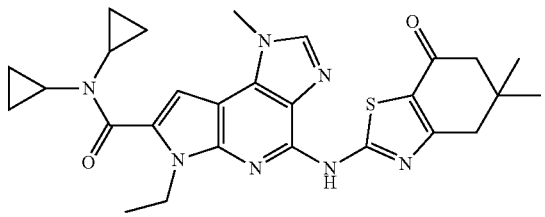 [SMILES: CCn1c(C(=O)N(C2CC2)C2CC2)cc2c3c(ncn3C)c(Nc3nc4c(s3)C(=O)CC(C)(C)C4)nc21]

Preparation of N,N-dicyclopropyl-4-(5,5-dimethyl-7-oxo-4,5,6,7-tetrahydrobenzo[d]thiazol-2-ylamino)-6-ethyl-1-methyl-1,6-dihydroimidazo[4,5-d]pyrrolo[2,3-b]pyridine-7-carboxamide This compound was prepared according to example 2 using 2-chloro-5,5-dimethylcyclohexane-1,3-dione (34.9 mg, 0.200 mmol) to provide N,N-dicyclopropyl-4-(5,5-dimethyl-7-oxo-4,5,6,7-tetrahydrobenzo[d]thiazol-2-ylamino)-6-ethyl-1-methyl-1,6-dihydroimidazo[4,5-d]pyrrolo[2,3-b]pyridine-7-carboxamide (11.24 mg, 21.7% yield) as a pale yellow solid.

MS (ESI) m/z 518.2 (M+H)

1H NMR (400 MHz, DMSO-$d_6$) δ ppm 11.93 (s, 1H), 8.19 (s, 1H), 7.28 (s, 1H), 4.62 (q, 2H), 4.06 (s, 3H), 2.89-2.98 (m, 2H), 2.80 (s, 2H), 2.40 (s, 2H), 1.41 (t, 3H, J=7.03 Hz), 1.09 (s, 6H), 0.73-0.80 (m, 4H), 0.63-0.71 (m, 4H)

Example 33

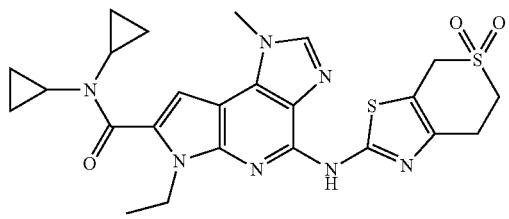 [SMILES: CCn1c(C(=O)N(C2CC2)C2CC2)cc2c3c(ncn3C)c(Nc3nc4c(s3)CS(=O)(=O)CC4)nc21]

Preparation of 4-(5,5-dioxo-4,5,6,7-tetrahydro-5$\lambda^6$-thiopyrano[4,3-d]thiazol-2-ylamino)-6-ethyl-1-methyl-1,6-dihydro-1,3,5,6-tetraaza-as-indacene-7-carboxylic acid dicyclopropylamide

33A Preparation of 3-bromodihydro-2H-thiopyran-4(3H)-one

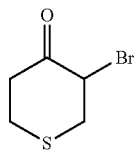

To a mixture of tetrahydrothiopyran-4-one (0.5 g, 4.30 mmol) in dichloromethane (51.2 mL) and methanol (20.49 mL) was added tetra-n-butylammonium tribromide (2.283 g, 4.73 mmol). The reaction mixture was stirred at rt 2.5 h. Solvent was removed in vacuo. The crude solid was triturated with ether (3 x). The combined ether layers were dried over anhydrous magnesium sulfate, filtered and concentrated in vacuo. The product was isolated as a pale orange oil. Material was used immediately in the next reaction.

33B Preparation of 3-bromo-1,1-dioxo-tetrahydro-1$\lambda^6$-thiopyran-4-one

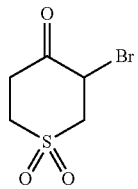

To a cooled (0° C.) of 3-bromodihydro-2H-thiopyran-4(3H)-one (example 33A, 0.791 g, 4.05 mmol) in dichloromethane (20.27 mL) was added mCPBA (1.749 g, 10.14 mmol) slowly. The reaction mixture was allowed to warm to room temperature. The reaction mixture was quenched with saturated aqueous sodium bicarbonate. The aqueous layer was extracted with dichloromethane (2x). The combined organics were dried over anhydrous magenesium sulfate, filtered and concentrated in vacuo to afford 3-bromo-1,1-dioxo-tetrahydro-1$\lambda^6$-thiopyran-4-one as a white solid which was used immediately in the next reaction.

33 Preparation of 4-(5,5-dioxo-4,5,6,7-tetrahydro-5λ⁶-thiopyrano[4,3-d]thiazol-2-ylamino)-6-ethyl-1-methyl-1,6-dihydro-1,3,5,6-tetraaza-as-indacene-7-carboxylic acid dicyclopropylamide This compound was prepared according to example 1 using 3-bromo-1,1-dioxo-tetrahydro-1λ⁶-thiopyran-4-one (example 33B, 32.5 mg, 0.151 mmol) to provide 4-(5,5-dioxo-4,5,6,7-tetrahydro-5λ⁶-thiopyrano[4,3-d]thiazol-2-ylamino)-6-ethyl-1-methyl-1,6-dihydro-1,3,5,6-tetraaza-as-indacene-7-carboxylic acid dicyclopropylamide (9 mg, 17.56% yield) as a pale tan solid.

MS (ESI) m/z 526.2 (M+H)

1H NMR (400 MHz, DMSO-$d_6$) δ ppm 8.16 (s, 1H), 7.25 (s, 1H), 4.61 (q, 2H, J=6.78 Hz), 4.54 (s, 2H), 4.04 (s, 3H), 3.49, (7, 2H, J=6.02 Hz), 3.16 (t, 2H, J=8.16 Hz), 2.89-2.97 (m, 2H), 1.38 (t, 3H, J=7.03 Hz), 0.73-0.79 (m, 4H), 0.61-0.70 (m, 4H)

Example 34

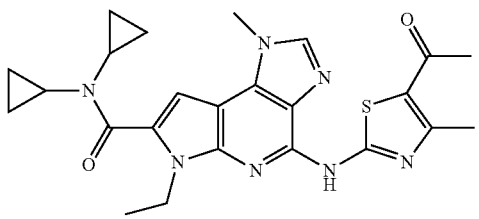 [SMILES: CCn1c(C(=O)N(C2CC2)C2CC2)cc2c3c(ncn3C)c(Nc3nc(C)c(C(C)=O)s3)nc21]

Preparation of 4-(5-acetyl-4-methylthiazol-2-ylamino)-N,N-dicyclopropyl-6-ethyl-1-methyl-1,6-dihydroimidazo[4,5-d]pyrrolo[2,3-b]pyridine-7-carboxamide This compound was prepared according to example 2 using 3-chloro-2,4-pentanedione (36.0 μL, 0.302 mmol) to provide 4-(5-acetyl-4-methylthiazol-2-ylamino)-N,N-dicyclopropyl-6-ethyl-1-methyl-1,6-dihydroimidazo[4,5-d]pyrrolo[2,3-b]pyridine-7-carboxamide (76 mg, 100% yield) as a pale yellow solid.

MS (ESI) m/z 478.2 (M+H)

1H NMR (400 MHz, DMSO-$d_6$) δ ppm 8.31 (s, 1H), 7.28 (s, 1H), 4.62 (q, 2H, J=6.94 Hz), 4.08 (s, 3H), 2.89-2.99 (m, 2H), 2.61 (s, 3H), 1.44 (t, 3H, J=7.03 Hz), 0.72-0.81 (m, 4H), 0.64-0.72 (m, 4H)

Example 35

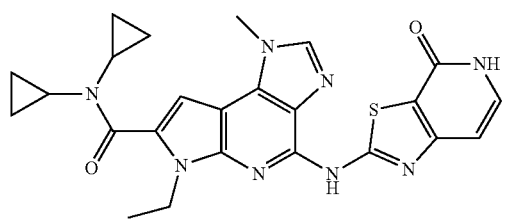 [SMILES: CCn1c(C(=O)N(C2CC2)C2CC2)cc2c3c(ncn3C)c(Nc3nc4cc[nH]c(=O)c4s3)nc21]

Preparation of N,N-dicyclopropyl-6-ethyl-1-methyl-4-(4-oxo-4,5-dihydrothiazolo[5,4-c]pyridin-2-ylamino)-1,6-dihydroimidazo[4,5-d]pyrrolo[2,3-b]pyridine-7-carboxamide 35A Preparation of 3-bromopiperidine-2,4-dione

To a mixture of piperidine-2,4-dione (0.072 g, 0.637 mmol) in acetic acid (1.591 mL) was added bromine (0.033 mL, 0.637 mmol) dropwise. The reaction mixture was stirred at rt 70 min. Dichloromethane was added and the cloudy mixture was concentrated in vacuo. The residual solution was treated with ethyl ether. A white solid crashed out and the AcOH/ether was decanted. The white solid, presumed to be product was carried forward. The white solid started liquifying and turning red rapidly upon exposure to light and standing.

35 Preparation of N,N-dicyclopropyl-6-ethyl-1-methyl-4-(4-oxo-4,5-dihydrothiazolo[5,4-c]pyridin-2-ylamino)-1,6-dihydroimidazo[4,5-d]pyrrolo[2,3-b]pyridine-7-carboxamide This compound was prepared according to example 2 using 3-bromopiperidine-2,4-dione (example 35A) to provide N,N-dicyclopropyl-6-ethyl-1-methyl-4-(4-oxo-4,5-dihydrothiazolo[5,4-c]pyridin-2-ylamino)-1,6-dihydroimidazo[4,5-d]pyrrolo[2,3-b]pyridine-7-carboxamide (4.51 mg, 12.3% yield) as a white solid containing 10% N,N-dicyclopropyl-6-ethyl-1-methyl-4-(4-oxo-4,5,6,7-tetrahydrothiazolo[5,4-c]pyridin-2-ylamino)-1,6-dihydroimidazo[4,5-d]pyrrolo[2,3-b]pyridine-7-carboxamide.

MS (ESI) m/z 489.1 (M+H)

1H NMR (400 MHz, DMSO-$d_6$) δ ppm 8.20 (s, 1H), 7.32-7.47 (m, 1H), 7.29 (s, 1H), 6.62 (d, 1H, J=7.03 Hz), 4.66 (q, 2H, J=7.19 Hz), 4.07 (s, 3H), 2.88-3.06 (m, 2H), 1.44 (t, 3H, J=7.03 Hz), 0.72-0.85 (m, 4H), 0.60-0.72 (m, 4H)

Example 36

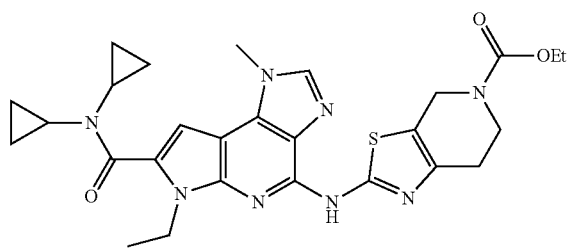 [SMILES: CCOC(=O)N1CCc2nc(Nc3nc4c(cc(C(=O)N(C5CC5)C5CC5)n4CC)c4c3ncn4C)sc2C1]

Preparation of ethyl 2-(7-(dicyclopropylcarbamoyl)-6-ethyl-1-methyl-1,6-dihydroimidazo[4,5-d]pyrrolo[2,3-b]pyridin-4-ylamino)-6,7-dihydrothiazolo[5,4-c]pyridine-5(4H)-carboxylate This compound was prepared according to example 2 using 3-bromo-4-oxo-piperidine-1-carboxylic acid ethyl ester to provide ethyl 2-(7-(dicyclopropylcarbamoyl)-6-ethyl-1-methyl-1,6-dihydroimidazo[4,5-d]pyrrolo[2,3-b]pyridin-4-ylamino)-6,7-dihydrothiazolo[5,4-c]pyridine-5(4H)-carboxylate (5 mg, 15.36% yield) as a white solid.

MS (ESI) m/z 549.2 (M+H)

1H NMR (400 MHz, DMSO-d$_6$) δ ppm 10.83 (br s, 1H), 8.12 (s, 1H), 7.23 (s, 1H), 4.56-4.67 (m, 4H), 4.10 (q, 2H, J=7.19 Hz), 4.04 (s, 3H), 3.72 (t, 2H, J=5.52 Hz), 2.87-2.98 (m, 2H), 2.64-2.73 (m, 2H), 1.38 (t, 3H, J=7.03 Hz), 1.22 (t, 3H, J=7.15 Hz), 0.71-0.81 (m, 4H), 0.60-0.71 (m, 4H)

Example 37

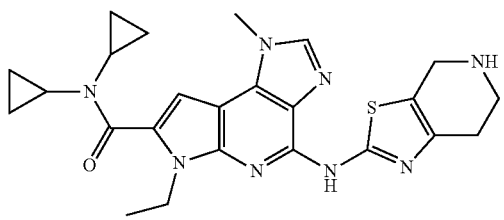 [SMILES: CCn1c(C(=O)N(C2CC2)C2CC2)cc2c3c(ncn3C)c(Nc3nc4c(s3)CNCC4)nc21]

Preparation of N,N-dicyclopropyl-6-ethyl-1-methyl-4-(4,5,6,7-tetrahydrothiazolo[5,4-c]pyridin-2-ylamino)-1,6-dihydroimidazo[4,5-d]pyrrolo[2,3-b]pyridine-7-carboxamide This compound was prepared according to example 2 using 3-bromopiperidin-4-one, hydrobromide (33.8 mg, 0.130 mmol) to provide N,N-dicyclopropyl-6-ethyl-1-methyl-4-(4,5,6,7-tetrahydrothiazolo[5,4-c]pyridin-2-ylamino)-1,6-dihydroimidazo[4,5-d]pyrrolo[2,3-b]pyridine-7-carboxamide (30 mg, 60% yield) as a pale yellow solid.

MS (ESI) m/z 477.3 (M+H)

1H NMR (400 MHz, DMSO-d$_6$) δ ppm 9.08 (br s, 2H), 8.25 (s, 1H), 7.27 (s, 1H), 4.63 (q, 2H, J=6.78 Hz), 4.38 (br s, 2H), 4.06 (s, 3H), 2.85-2.98 (m, 4H), 1.38 (t, 3H, J=7.03 Hz), 0.73-0.81 (m, 4H), 0.62-0.71 (m, 4H)

Example 38

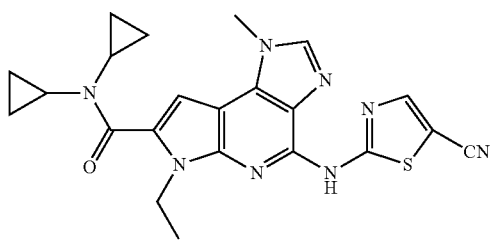 [SMILES: CCn1c(C(=O)N(C2CC2)C2CC2)cc2c3c(ncn3C)c(Nc3ncc(C#N)s3)nc21]

4-(5-cyanothiazol-2-ylamino)-N,N-dicyclopropyl-6-ethyl-1-methyl-1,6-dihydroimidazo[4,5-d]pyrrolo[2,3-b]pyridine-7-carboxamide To a mixture of 4-amino-N,N-dicyclopropyl-6-ethyl-1-methyl-1,6-dihydroimidazo[4,5-d]pyrrolo[2,3-b]pyridine-7-carboxamide (example 1J, 60 mg, 0.177 mmol), 2-chlorothiazole-5-carbonitrile (38.5 mg, 0.266 mmol), Pd2(dba)$_3$ (24.4 mg, 0.027 mmol), BINAP (49.7 mg, 0.080 mmol) and sodium tert-butoxide (27.3 mg, 0.284 mmol) was added DME (1 ml). The mixture was purged with argon gas for 5 min and heated to 85° C. for 3 h. The reaction mixture showed ~60% conversion by HPLC and was filtered through a plug of Celite and concentrated. The crude product was purified by preparative HPLC to afford 4-(5-cyanothiazol-2-ylamino)-N,N-dicyclopropyl-6-ethyl-1-methyl-1,6-dihydroimidazo[4,5-d]pyrrolo[2,3-b]pyridine-7-carboxamide as a off-white solid.

MS (ESI) m/z 447.2 (M+H).

$^1$H NMR (500 MHz, CD$_3$OD-CDCl$_3$) δ: 8.60 (s, 1H), 8.04 (s, 1H), 7.56 (s, 4H), 7.13 (s, 1H), 4.71 (q, J=7.1 Hz, 2H), 4.20 (s, 3H), 2.84-2.91 (m, 2H), 1.52 (t, J=7.1 Hz, 3H), 0.83-0.90 (m, 5H), 0.74-0.80 (m, 4H).

Example 39

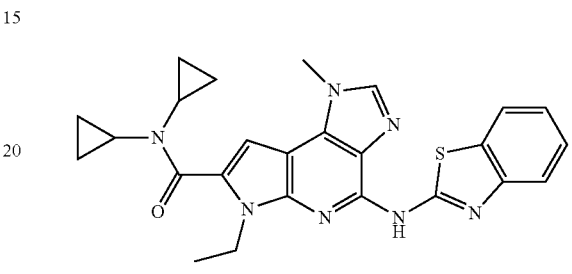

4-(benzo[d]thiazol-2-ylamino)-N,N-dicyclopropyl-6-ethyl-1-methyl-1,6-dihydroimidazo[4,5-d]pyrrolo[2,3-b]pyridine-7-carboxamide To a solution of 4-amino-N,N-dicyclopropyl-6-ethyl-1-methyl-1,6-dihydroimidazo[4,5-d]pyrrolo[2,3-b]pyridine-7-carboxamide (example 1J, 21.2 mg, 0.063 mmol) in DMF (626 μL) was added sodium hydride (10.02 mg, 0.251 mmol) in one portion. After 20 min, 2-bromo-1,3-benzothiazole (53.6 mg, 0.251 mmol) was added. The reaction mixture was stirred at room temperature for 16 h. The reaction mixture was quenched with water and diluted with ethyl acetate. The aqueous layer was extracted with ethyl acetate. The combined organics were washed with 10% LiCl, dried over anhydrous sodium sulfate, filtered and concentrated in vacuo. The crude residue was purified by flash chromatography using an Isco 4 g column eluting with 0-5% MeOH/CH$_2$Cl$_2$ to yield 4-(benzo[d]thiazol-2-ylamino)-N,N-dicyclopropyl-6-ethyl-1-methyl-1,6-dihydroimidazo[4,5-d]pyrrolo[2,3-b]pyridine-7-carboxamide (6.8 mg, 21.87% yield) as an off-white solid.

MS (ESI) m/z 472.2 (M+H)

1H NMR (500 MHz, DMSO-d$_6$) δ ppm 8.17 (s, 1H), 7.95 (d, 1H, J=7.97 Hz), 7.67 (d, 1H, J=8.25 Hz), 7.39 (t, 1H, J=7.97 Hz), 7.27 (s, 1H), 7.22 (t, 1H, J=8.52 Hz), 4.70 (q, 2H, J=7.06 Hz), 4.06 (s, 3H), 2.88-2.99 (m, 2H), 1.65 (br s, 1H), 1.45 (t, 3H, J=7.01 Hz), 0.74-0.84 (m, 4H), 0.64-0.73 (m, 4H)

Example 40

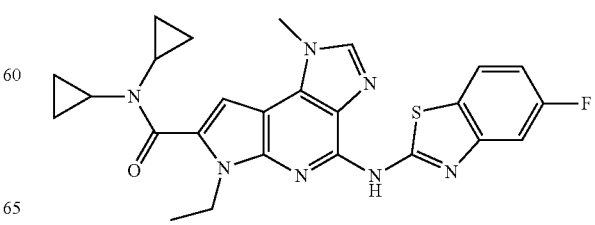

Preparation of N,N-dicyclopropyl-6-ethyl-4-(5-fluorobenzo[d]thiazol-2-ylamino)-1-methyl-1,6-dihydroimidazo[4,5-d]pyrrolo[2,3-b]pyridine-7-carboxamide 40A Preparation of
5-fluoro-2-(methylthio)benzo[d]thiazole

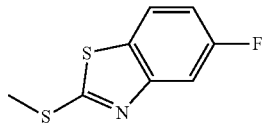

To a solution of 5-fluoro-2-mercaptobenzothiazole (0.15 g, 0.810 mmol) in THF (8.10 mL) cooled to 0° C. was added sodium hydride (0.036 g, 0.891 mmol). After stirring 10 min, iodomethane (0.076 mL, 1.215 mmol) was added and the reaction mixture was slowly warmed to room temperature over 2 h. The reaction was diluted with ethyl acetate and quenched with saturated aqueous sodium bicarbonate. The organic layer was washed with brine, dried over anhydrous sodium sulfate, filtered and concentrated in vacuo. 5-fluoro-2-(methylthio)benzo[d]thiazole (0.178 g, 110% yield) was isolated as a white solid. Material was used without any further purification.

MS (ESI) m/z 200.0 (M+H)
1H NMR (400 MHz, CHLOROFORM-d) δ ppm 7.68 (dd, 1H, J=8.81, 5.04 Hz), 7.56 (dd, 1H, J=9.57, 2.52 Hz), 7.07 (td, 1H, J=8.81, 2.52 Hz), 2.80 (s, 3H)

40B Preparation of
5-fluoro-2-(methylsulfinyl)benzo[d]thiazole

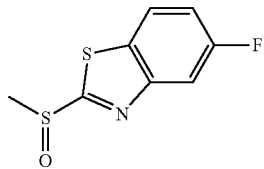

5-Fluoro-2-(methylthio)benzo[d]thiazole (example 40A, 0.178 g, 0.893 mmol) was dissolved in CH$_2$Cl$_2$ (5.96 mL). mCPBA (0.154 g, 0.893 mmol) was added in one portion and the reaction mixture was stirred at room temperature. The reaction was quenched with saturated aqueous sodium bicarbonate and diluted with dichloromethane. The aqueous layer was extracted with dichloromethane (2×). The combined organic were washed with brine, dried over anhydrous magnesium sulfate, filtered, and concentrated in vacuo. 5-Fluoro-2-(methylsulfinyl)benzo[d]thiazole (0.180 g, 94% yield) was isolated as a white solid and used without further purification.

MS (ESI) m/z 216.0 (M+H)
1H NMR (500 MHz, CHLOROFORM-d) δ ppm 7.97 (dd, 1H, J=9.07, 4.95 Hz), 7.76 (dd, 1H, J=9.07, 2.47 Hz), 7.27-7.34 (m, 1H), 3.10 (s, 3H)

40 Preparation of N,N-dicyclopropyl-6-ethyl-4-(5-fluorobenzo[d]thiazol-2-ylamino)-1-methyl-1,6-dihydroimidazo[4,5-d]pyrrolo[2,3-b]pyridine-7-carboxamide To a solution of 4-amino-N,N-dicyclopropyl-6-ethyl-1-methyl-1,6-dihydroimidazo[4,5-d]pyrrolo[2,3-b]pyridine-7-carboxamide (example 1J, 50 mg, 0.148 mmol) in DMF (1.5 mL) was added sodium hydride (17.73 mg, 0.443 mmol). After 20 min, 5-fluoro-2-(methylsulfinyl)benzo[d]thiazole (example 40B, 95 mg, 0.443 mmol) was added in one portion. The reaction mixture was stirred at room temperature. The reaction mixture was diluted with ethyl acetate and quenched with water. The aqueous layer was extracted with ethyl acetate (2×). The combined organic layers were washed with 10% lithium chloride solution (2×), dried over anhydrous sodium sulfate, filtered and concentrated in vacuo. The crude residue was purified by flash chromatography using an Isco 12 g column eluting with 0-5% MeOH/CH$_2$Cl$_2$ to provide N,N-dicyclopropyl-6-ethyl-4-(5-fluorobenzo[d]thiazol-2-ylamino)-1-methyl-1,6-dihydroimidazo[4,5-d]pyrrolo[2,3-b]pyridine-7-carboxamide (13 mg, 17.07% yield).

MS (CI) m/z 490.2 (M+H)
1H NMR (400 MHz, DMSO-d$_6$) δ ppm 11.53 (br s, 1H), 8.19 (s, 1H), 7.95-8.02 (m, 1H), 7.47 (d, 1H, J=9.82 Hz), 7.28 (s, 1H), 7.09 (t, 1H, J=8.18 Hz), 4.69 (q, 2H, J=7.13 Hz), 4.06 (s, 3H), 2.89-3.02 (m, 2H), 1.45 (t, 3H, J=7.05 Hz), 0.74-0.81 (m, 4H), 0.63-0.71 (m, 4H)

Example 41

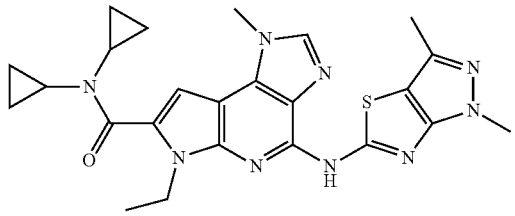 [SMILES: CCn1c(C(=O)N(C2CC2)C2CC2)cc2c3c(ncn3C)c(Nc3nc4c(s3)c(C)nn4C)nc21]

Preparation of N,N-dicyclopropyl-4-(1,3-dimethyl-1H-pyrazolo[3,4-d]thiazol-5-ylamino)-6-ethyl-1-methyl-1,6-dihydroimidazo[4,5-d]pyrrolo[2,3-b]pyridine-7-carboxamide 41A Preparation of N,N-dicyclopropyl-6-ethyl-4-isothiocyanato-1-methyl-1,6-dihydroimidazo[4,5-d]pyrrolo[2,3-b]pyridine-7-carboxamide

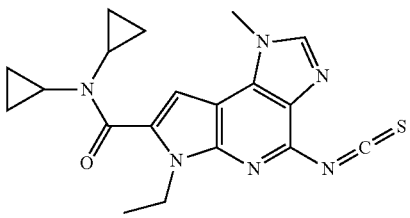 [SMILES: CCn1c(C(=O)N(C2CC2)C2CC2)cc2c3c(ncn3C)c(N=C=S)nc21]

To a mixture of 4-amino-N,N-dicyclopropyl-6-ethyl-1-methyl-1,6-dihydroimidazo[4,5-d]pyrrolo[2,3-b]pyridine-7-carboxamide (194.5 mg, 0.575 mmol) in dichloromethane (2874 µL) in a round bottom flask under nitrogen was added 1,1'-thiocarbonyldi-2(1H)-pyridone (133 mg, 0.575 mmol). The reaction mixture was stirred at room temperature for 16 h. The reaction mixture was concentrated under reduced pressure. N,N-Dicyclopropyl-6-ethyl-4-isothiocyanato-1-methyl-1,6-dihydroimidazo[4,5-d]pyrrolo[2,3-b]pyridine-7- carboxamide was isolated as a yellow sticky solid. Material was used as is in subsequent reactions.

MS (ESI) m/z 381.1 (M+H)

41B Preparation of N,N-dicyclopropyl-4-(3-(1,3-dimethyl-1H-pyrazol-5-yl)thioureido)-6-ethyl-1-methyl-1,6-dihydroimidazo[4,5-d]pyrrolo[2,3-b]pyridine-7-carboxamide

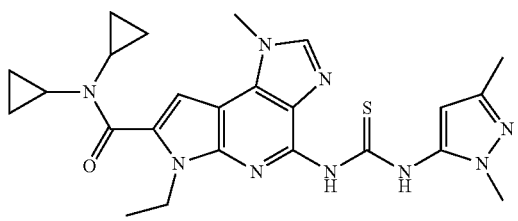 [SMILES: CCn1c(C(=O)N(C2CC2)C2CC2)cc2c3c(ncn3C)c(NC(=S)Nc3cc(C)nn3C)nc21]

To a flask charged with N,N-dicyclopropyl-6-ethyl-4-isothiocyanato-1-methyl-1,6-dihydroimidazo[4,5-d]pyrrolo[2,3-b]pyridine-7-carboxamide (example 41A, 0.0342 g, 0.090 mmol) was added THF (0.449 mL). 5-Amino-1,3-dimethylpyrazole (0.012 g, 0.108 mmol) was added followed by sodium hydride (3.60 mg, 0.090 mmol). The reaction mixture was stirred at room temperature for 16 h. The reaction mixture was diluted with ethyl acetate and quenched with saturated aqueous sodium bicarbonate. The aqueous layer was extracted with ethyl acetate. The combined organics were dried over anhydrous sodium sulfate, filtered and concentrated in vacuo. The crude material was used without further purification.

MS (ESI) m/z 492.2 (M+H)

41 Preparation of N,N-dicyclopropyl-4-(1,3-dimethyl-1H-pyrazolo[3,4-d]thiazol-5-ylamino)-6-ethyl-1-methyl-1,6-dihydroimidazo[4,5-d]pyrrolo[2,3-b]pyridine-7-carboxamide N,N-Dicyclopropyl-4-(3-(1,3-dimethyl-1H-pyrazol-5-yl)thioureido)-6-ethyl-1-methyl-1,6-dihydroimidazo[4,5-d]pyrrolo[2,3-b]pyridine-7-carboxamide (example 41B, 41 mg, 0.083 mmol) was dissolved in chloroform (2780 µL) and cooled to 0° C. NIS (18.76 mg, 0.083 mmol) was slowly added and the reaction was warmed to room temperature. The reaction mixture was concentrated. Methanol and ether were added and the mixture was filtered. After standing for a week, product precipitated out of the solution. The product was triturated with methanol. N,N-Dicyclopropyl-4-(1,3-dimethyl-1H-pyrazolo[3,4-d]thiazol-5-ylamino)-6-ethyl-1-methyl-1,6-dihydroimidazo[4,5-d]pyrrolo[2,3-b]pyridine-7-carboxamide was isolated as a pale yellow solid (8.1 mg, 20% yield).

MS (ESI) m/z 490.3 (M+H)

1H NMR (400 MHz, DMSO-$d_6$) δ ppm 11.39 (s, 1H), 8.17 (s, 1H), 7.26 (s, 1H), 4.66 (q, 2H, J=7.03 Hz), 4.05 (s, 3H), 3.85 (s, 3H) 2.88-3.00 (m, 2H), 2.33 (s, 3H), 1.43 (t, 3H, J=7.03 Hz), 0.72-0.82 (m, 4H), 0.61-0.73 (m, 4H)

Example 42

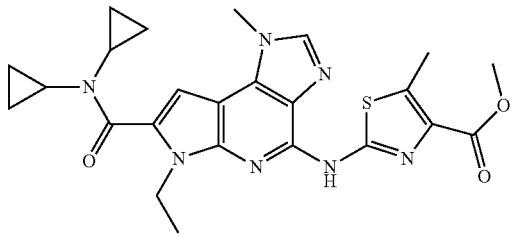 [SMILES: CCn1c(C(=O)N(C2CC2)C2CC2)cc2c3c(ncn3C)c(Nc3nc(C(=O)OC)c(C)s3)nc21]

Methyl 2-(7-(dicyclopropylcarbamoyl)-6-ethyl-1-methyl-1,6-dihydroimidazo[4,5-d]pyrrolo[2,3-b]pyridin-4-ylamino)-5-methylthiazole-4-carboxylate Methyl 3-bromo-2-oxobutanoate (320 mg, 1.642 mmol) was added to a suspension of N,N-dicyclopropyl-6-ethyl-1-methyl-4-thioureido-1,6-dihydroimidazo[4,5-d]pyrrolo[2,3-b]pyridine-7-carboxamide (example 2B, 435 mg, 1.094 mmol) in EtOH (10 ml) and the reaction mixture was heated at 65° C. for 2 h. The solvent was removed in vacuo and the residue purified by silica gel chromatography (2-10% MeOH/dichloromethane) to give methyl 2-(7-(dicyclopropylcarbamoyl)-6-ethyl-1-methyl-1,6-dihydroimidazo[4,5-d]pyrrolo[2,3-b]pyridin-4-ylamino)-5-methylthiazole-4-carboxylate (380 mg, 70% yield) as yellow solid.

MS (ESI) rt=0.87 min, m/z 494 (M+H)

1H NMR(CHLOROFORM-d) δ: 9.41 (br. s., 1H), 7.78 (s, 1H), 6.89 (s, 1H), 4.73 (q, J=7.0 Hz, 2H), 4.03 (s, 3H), 3.95 (s, 3H), 2.80-2.87 (m, 2H), 2.77 (s, 3H), 1.54 (t, J=7.0 Hz, 3H), 0.83-0.90 (m, 4H), 0.73-0.80 (m, 4H).

Example 43

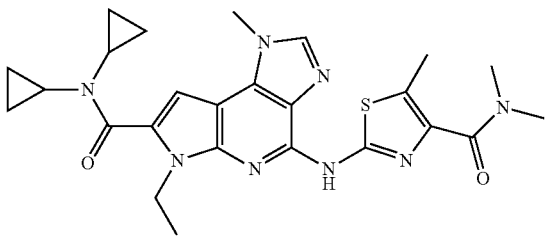 [SMILES: CCn1c(C(=O)N(C2CC2)C2CC2)cc2c3c(ncn3C)c(Nc3nc(C(=O)N(C)C)c(C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N,N,5-trimethylthiazole-4-carboxamide 43A Preparation of 2-(7-(dicyclopropylcarbamoyl)-6-ethyl-1-methyl-1,6-dihydroimidazo[4,5-d]pyrrolo[2,3-b]pyridin-4-ylamino)-5-methylthiazole-4-carboxylic acid

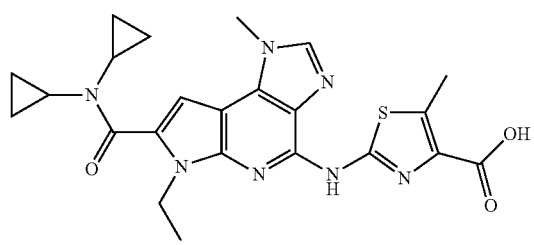 [SMILES: CCn1c(C(=O)N(C2CC2)C2CC2)cc2c3c(ncn3C)c(Nc3nc(C(=O)O)c(C)s3)nc21]

1N Aqueous NaOH (0.962 mL, 0.962 mmol) was added to a suspension of methyl 2-(7-(dicyclopropylcarbamoyl)-6- ethyl-1-methyl-1,6-dihydroimidazo[4,5-d]pyrrolo[2,3-b]pyridin-4-ylamino)-5-methylthiazole-4-carboxylate (example 41, 0.19 g, 0.385 mmol) in ethanol (2 mL) and the mixture was heated at 60° C. for 2 h. The reaction was cooled to room temperature and acidified with 1N HCl to pH 4. The reaction mixture was concentrated and the residue triturated 5× with methanol. The combined methanol washes were concentrated, and the remaining solid washed 3× with 2:1 ether/dichloromethane provided 2-(7-(dicyclopropylcarbamoyl)-6-ethyl-1-methyl-1,6-dihydroimidazo[4,5-d]pyrrolo[2,3-b]pyridin-4-ylamino)-5-methylthiazole-4-carboxylic acid (105 mg, 57% yield).

MS (ESI) rt=0.79 min, m/z 480 (M+H)

43 Preparation of 2-(7-(dicyclopropylcarbamoyl)-6-ethyl-1-methyl-1,6-dihydroimidazo[4,5-d]pyrrolo[2,3-b]pyridin-4-ylamino)-N,N,5-trimethylthiazole-4-carboxamide A mixture of 2-(7-(dicyclopropylcarbamoyl)-6-ethyl-1-methyl-1,6-dihydroimidazo[4,5-d]pyrrolo[2,3-b]pyridin-4-ylamino)-5-methylthiazole-4-carboxylic acid (43A, 30 mg, 0.063 mmol), dimethylamine, 40% aqueous (0.016 mL, 0.125 mmol) and HATU (35.7 mg, 0.094 mmol) in DMF (1 mL) was stirred at room temperature for 3 h. The solvent was evaporated off and the residue purified by silica gel chromatography (2-10% MeOH/dichloromethane). The material was further purified by preparative HPLC to give of 2-(7-(dicyclopropylcarbamoyl)-6-ethyl-1-methyl-1,6-dihydroimidazo[4,5-d]pyrrolo[2,3-b]pyridin-4-ylamino)-N,N,5-trimethylthiazole-4-carboxamide (20 mg, 62.5% yield) as off-white solid.

MS (ESI) m/z 507 (M+H)

1H NMR (400 MHz, CHLOROFORM-d) δ: 7.79 (s, 1H), 6.90 (s, 1H), 4.73 (q, J=7.0 Hz, 2H), 4.05 (s, 3H), 3.12 (s, 3H), 3.11 (s, 3H), 2.80-2.87 (m, 2H), 2.53 (s, 3H), 1.53 (t, J=7.2 Hz, 3H), 0.83-0.91 (m, 4H), 0.74-0.80 (m, 4H)

Examples 44-49 were prepared using the similar protocol as described for example 42

Example 44

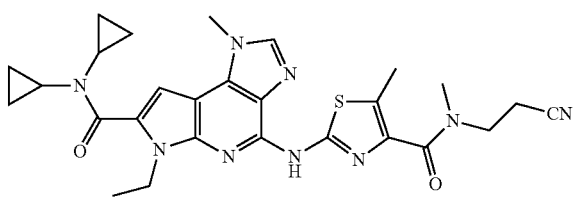 [SMILES: CCn1c(C(=O)N(C2CC2)C2CC2)cc2c3c(ncn3C)c(Nc3nc(C(=O)N(C)CCC#N)c(C)s3)nc21]

N-(2-cyanoethyl)-2-(7-(dicyclopropylcarbamoyl)-6-ethyl-1-methyl-1,6-dihydroimidazo[4,5-d]pyrrolo[2,3-b]pyridin-4-ylamino)-N,5-dimethylthiazole-4-carboxamide MS (ESI) m/z 546 (M+H).

1H NMR (400 MHz, CHLOROFORM-d) δ ppm 9.34 (br. s., 1 H) 7.75 (d, J=5.94 Hz, 1 H) 6.90 (s, 1 H) 4.74 (q, J=7.04 Hz, 2 H) 4.06 (s, 3 H) 3.80 (t, J=6.71 Hz, 2 H) 3.11-3.32 (m, 3 H) 2.95 (t, J=6.71 Hz, 2 H) 2.78-2.91 (m, 2 H) 2.58 (d, J=15.85 Hz, 3 H) 1.54 (t, J=7.04 Hz, 3 H) 0.70-0.94 (m, 8 H).

Example 45

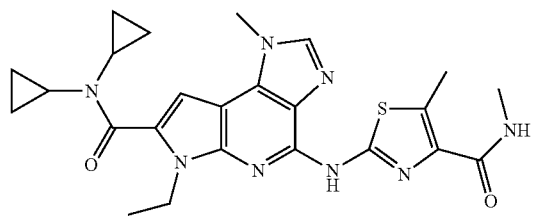 [SMILES: CCn1c(C(=O)N(C2CC2)C2CC2)cc2c3c(ncn3C)c(Nc3nc(C(=O)NC)c(C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N,5-dimethylthiazole-4-carboxamide MS (ESI) m/z 493 (M+H).

1H NMR (500 MHz, CHLOROFORM-d) δ ppm 7.84 (s, 1 H) 7.40 (d, J=4.99 Hz, 1 H) 6.90 (s, 1 H) 4.73 (q, J=6.94 Hz, 2 H) 4.08 (s, 3 H) 2.99 (d, J=4.99 Hz, 3 H) 2.73-2.91 (m, 5 H) 2.14 (s, 1 H) 1.53 (t, J=7.07 Hz, 3 H) 0.66-0.97 (m, 8 H).

Example 46

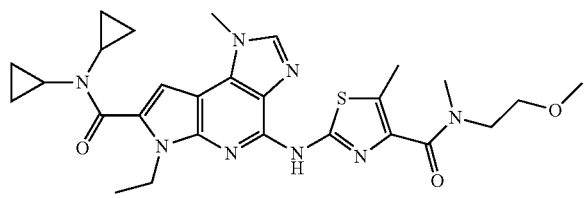 [SMILES: CCn1c(C(=O)N(C2CC2)C2CC2)cc2c3c(ncn3C)c(Nc3nc(C(=O)N(C)CCOC)c(C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N-(2-methoxyethyl)-N,5-dimethylthiazole-4-carboxamide MS (ESI) m/z 551 (M+H).

1H NMR (500 MHz, CHLOROFORM-d) δ ppm 7.73 (d, J=3.05 Hz, 1 H) 6.90 (s, 1 H) 4.74 (q, J=7.21 Hz, 2 H) 4.05 (s, 3 H) 3.72 (dd, J=13.73, 4.58 Hz, 2 H) 3.61-3.68 (m, 1 H) 3.57 (t, J=5.41 Hz, 1 H) 3.27-3.45 (m, 3 H) 3.17 (d, J=8.32 Hz, 3 H) 2.79-2.88 (m, 2 H) 2.54 (d, J=5.83 Hz, 3 H) 1.54 (t, J=7.07 Hz, 3 H) 0.73-0.92 (m, 8 H).

Example 47

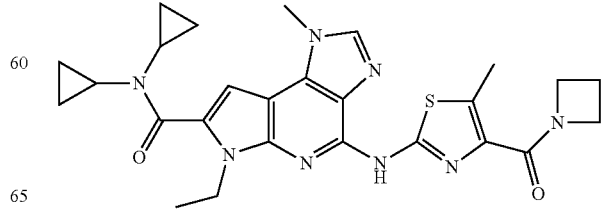

4-(4-(azetidine-1-carbonyl)-5-methylthiazol-2-ylamino)-N,N-dicyclopropyl-6-ethyl-1-methyl-1,6-dihydroimidazo[4,5-d]pyrrolo[2,3-b]pyridine-7-carboxamide MS (ESI) m/z 519 (M+H).

1H NMR (500 MHz, CHLOROFORM-d) δ ppm 8.50-9.65 (m, 1 H) 8.00 (s, 1 H) 6.88 (s, 1 H) 4.68 (q, J=7.21 Hz, 2 H) 4.59 (t, J=7.63 Hz, 2 H) 4.18 (t, J=7.77 Hz, 2 H) 4.09 (s, 3 H) 2.78-2.89 (m, 2 H) 2.72 (s, 3 H) 2.30 (quin, J=7.70 Hz, 2 H) 1.49 (t, J=7.07 Hz, 3 H) 0.72-0.92 (m, 8 H).

Example 48

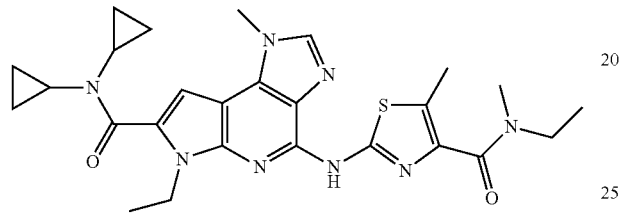

2-(7-(dicyclopropylcarbamoyl)-6-ethyl-1-methyl-1,6-dihydroimidazo[4,5-d]pyrrolo[2,3-b]pyridin-4-ylamino)-N-ethyl-N,5-dimethylthiazole-4-carboxamide MS (ESI) m/z 521 (M+H).

1H NMR (400 MHz, CHLOROFORM-d) δ ppm 7.77 (s, 1 H) 6.89 (s, 1 H) 4.74 (q, J=7.04 Hz, 2 H) 4.04 (s, 3 H) 3.36-3.66 (m, 2 H) 3.07 (d, J=14.09 Hz, 3 H) 2.72-2.90 (m, 2 H) 2.51 (s, 3 H) 2.11 (s, 1 H) 1.54 (t, J=7.04 Hz, 3 H) 1.13-1.35 (m, 3 H) 0.66-0.90 (m, 8 H).

Example 49

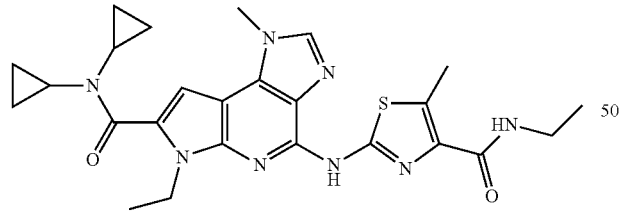

2-(7-(dicyclopropylcarbamoyl)-6-ethyl-1-methyl-1,6-dihydroimidazo[4,5-d]pyrrolo[2,3-b]pyridine-4-ylamino)-N-ethyl-5-methylthiazole-4-carboxamide MS (ESI) m/z 508 (M+H).

1H NMR (400 MHz, CHLOROFORM-d) δ ppm 7.78 (s, 1 H) 6.89 (s, 1 H) 4.73 (q, J=7.04 Hz, 2 H) 4.42 (q, J=7.12 Hz, 2 H) 4.04 (s, 3 H) 2.78-2.91 (m, 2 H) 2.75 (s, 3 H) 2.15 (s, 1 H) 1.54 (t, J=7.04 Hz, 3 H) 1.44 (t, J=7.04 Hz, 3 H) 0.68-0.91 (m, 8 H).

Example 50

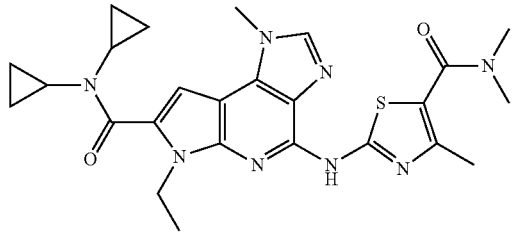 [SMILES: CCn1c(C(=O)N(C2CC2)C2CC2)cc2c3c(ncn3C)c(Nc3nc(C)c(C(=O)N(C)C)s3)nc21]

2-(7-(dicyclopropylcarbamoyl)-6-ethyl-1-methyl-1,6-dihydroimidazo[4,5-d]pyrrolo[2,3-b]pyridin-4-ylamino)-N,N,4-trimethylthiazole-5-carboxamid 50A Preparation of methyl 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylate

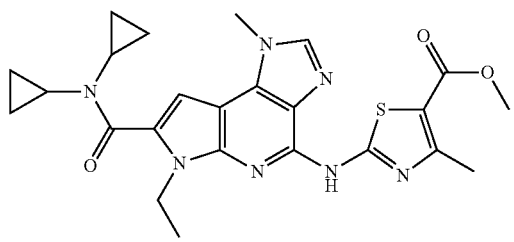 [SMILES: CCn1c(C(=O)N(C2CC2)C2CC2)cc2c3c(ncn3C)c(Nc3nc(C)c(C(=O)OC)s3)nc21]

Methyl 2-bromo-3-oxobutanoate (213 mg, 1.094 mmol, prepared following the procedure described by Abu T. Khan et al. in *Tetrahedron Letters* 2006, 47, 2751-2754) was added to a suspension of N,N-dicyclopropyl-6-ethyl-1-methyl-4-thioureido-1,6-dihydroimidazo[4,5-d]pyrrolo[2,3-b]pyridine-7-carboxamide (example 2B, 290 mg, 0.730 mmol) in ethanol (5 ml) and the reaction mixture was heated at 65° C. for 2 h. LC/MS shows completion of reaction (reaction remained as suspension all the time). The reaction mixture was concentrated to remove ethanol, and taken up in dichloromethane. The solution was washed with saturated sodium bicarbonate and the aqueous layer was back extracted with dichloromethane. The combined organic layers were dried over magnesium sulfate, filtered, and concentrated in vacuo. The crude was purified by flash chromatography using an automated ISCO system (40 g column, eluting with 0-5% methanol/dichloromethane) to afford methyl 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylate (301 mg, 0.610 mmol, 84% yield) as a white solid.

MS (ESI) m/z 494.4 (M+H).

$^1$H NMR (400 MHz, CHLOROFORM-d) δ: 7.75 (s, 1H), 6.92 (s, 1H), 4.76 (q, J=7.0 Hz, 2H), 4.08 (s, 3H), 3.92 (s, 3H), 2.82-2.89 (m, 2H), 2.71 (s, 3H), 1.59 (t, J=7.0 Hz, 3H), 0.85-0.93 (m, 4H), 0.75-0.82 (m, 4H)

50B Preparation of 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylic acid

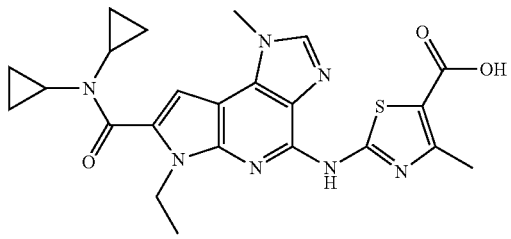 [SMILES: CCn1c(C(=O)N(C2CC2)C2CC2)cc2c3c(ncn3C)c(Nc3nc(C)c(C(=O)O)s3)nc21]

A mixture of methyl 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylate (example 50A, 288 mg, 0.583 mmol) and 1N NaOH (5.83 mL, 5.830 mmol) in methanol (5 mL) was heated at 65° C. for 18 h. Methanol was evaporated and the aqueous solution was acidified to pH 4 with 1N HCl, solids crashed out of solution and were retained after filtration to afford the desired acid in pure form. The aqueous mixture was then extracted with dichloromethane, The organic layer was dried over magnesium sulfate, filtered and concentrated in vacuo. The crude was purified by flash chromatography using an automated ISCO system (40 g column, eluting with 0-8% methanol/dichloromethane). A total of 260 mg of 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylic acid (93% yield) was obtained as a yellow solid.

MS (ESI) m/z 480.2 (M+H).

$^1$H NMR (500 MHz, DMSO-$d_6$) δ: 8.03 (br. s., 1H), 7.06 (s, 1H), 4.40 (q, J=7.0 Hz, 2H), 3.86 (s, 3H), 2.96 (s, 1H), 2.69-2.76 (m, 2H), 2.36 (s, 3H), 1.20 (t, J=6.9 Hz, 3H), 0.56 (d, J=5.5 Hz, 4H), 0.45-0.50 (m, 4H).

50 Preparation of 2-(7-(dicyclopropylcarbamoyl)-6-ethyl-1-methyl-1,6-dihydroimidazo[4,5-d]pyrrolo[2,3-b]pyridin-4-ylamino)-N,N,4-trimethylthiazole-5-carboxamide A mixture of 2-(7-(dicyclopropylcarbamoyl)-6-ethyl-1-methyl-1,6-dihydroimidazo[4,5-d]pyrrolo[2,3-b]pyridin-4-ylamino)-4-methylthiazole-5-carboxylic acid (example 50B, 51 mg, 0.106 mmol), dimethylamine (40% in water, 0.027 mL, 0.213 mmol), HATU (52.6 mg, 0.138 mmol) and 2,6-lutidine (0.025 mL, 0.213 mmol) in DMF (1 mL) was stirred at room temperature for 2 h. Solvent was evaporated and the residue was purified by flash chromatography on silica gel using an automated ISCO system (24 g column, eluting with 2-8% methanol/dichloromethane). The product was further purified by preparative HPLC. 2-(7-(Dicyclopropylcarbamoyl)-6-ethyl-1-methyl-1,6-dihydroimidazo[4,5-d]pyrrolo[2,3-b]pyridin-4-ylamino)-N,N,4-trimethylthiazole-5-carboxamide (17 mg, 0.032 mmol, 30.0% yield) was obtained as a off-white solid.

MS (ESI) m/z 507.1 (M+H).

1H NMR (400 MHz, METHANOL-$d_4$) δ: 8.75 (s, 1H), 7.27 (s, 1H), 4.66 (q, J=7.0 Hz, 2H), 4.21 (s, 3H), 3.19 (s, 6H), 2.95-3.02 (m, 2H), 2.39 (s, 3H), 1.47 (t, J=7.2 Hz, 3H), 0.86-0.93 (m, 4H), 0.78-0.84 (m, 4H)

Examples 51-55 were synthesized using the same method as used for 50.

Example 51

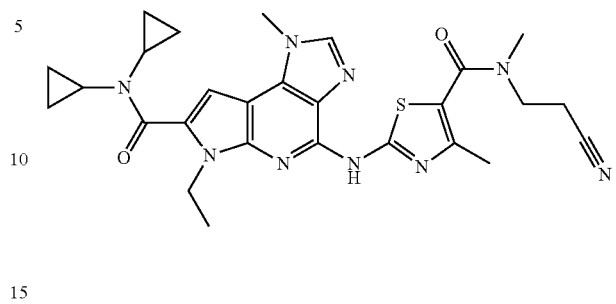

N-(2-cyanoethyl)-2-(7-(dicyclopropylcarbamoyl)-6-ethyl-1-methyl-1,6-dihydroimidazo[4,5-d]pyrrolo[2,3-b]pyridin-4-ylamino)-N,4-dimethylthiazole-5-carboxamide MS (ESI) m/z 546.1 (M+H).

1H NMR (CDCl$_3$) δ: 7.77 (s, 1H), 6.89 (s, 1H), 4.71 (q, J=6.9 Hz, 2H), 4.05 (s, 3H), 3.81 (t, J=6.6 Hz, 2H), 3.31 (s, 3H), 2.78-2.86 (m, 4H), 2.44 (s, 3H), 1.53 (t, J=7.0 Hz, 3H), 0.83-0.90 (m, 4H), 0.73-0.79 (m, 4H).

Example 52

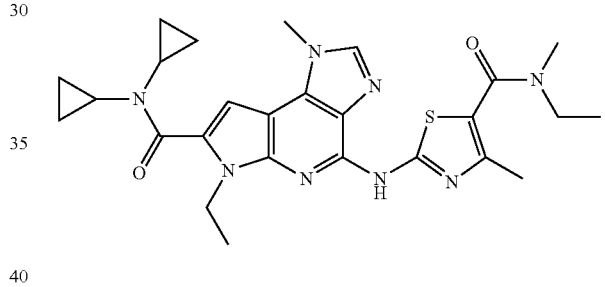

2-(7-(dicyclopropylcarbamoyl)-6-ethyl-1-methyl-1,6-dihydroimidazo[4,5-d]pyrrolo[2,3-b]pyridin-4-ylamino)-N-ethyl-N,4-dimethylthiazole-5-carboxamide MS (ESI) m/z 521.1 (M+H).

$^1$H NMR (400 MHz, CDCl$_3$) δ: 7.74 (s, 1H), 6.88 (s, 1H), 4.72 (q, J=7.0 Hz, 2H), 4.04 (s, 3H), 3.57 (q, J=7.2 Hz, 2H), 3.11 (s, 3H), 2.79-2.86 (m, 2H), 2.40 (s, 3H), 1.51 (t, J=7.0 Hz, 3H), 1.25 (t, J=7.2 Hz, 3H), 0.82-0.90 (m, 4H), 0.73-0.79 (m, 4H).

Example 53

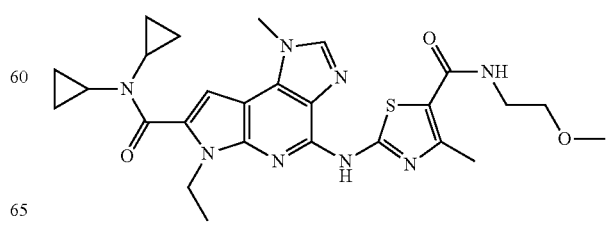

2-(7-(dicyclopropylcarbamoyl)-6-ethyl-1-methyl-1,
6-dihydroimidazo[4,5-d]pyrrolo[2,3-b]pyridin-4-
ylamino)-N-(2-methoxyethyl)-4-methylthiazole-5-
carboxamide MS (ESI) m/z 537.1 (M+H).
$^1$H NMR (400 MHz, CDCl$_3$) δ: 7.74 (s, 1H), 6.89 (s, 1H), 6.13 (t, J=4.7 Hz, 1H), 4.74 (q, J=7.0 Hz, 2H), 4.05 (s, 3H), 3.65 (q, J=5.1 Hz, 2H), 3.58 (t, J=4.8 Hz, 2H), 3.42 (s, 3H), 2.79-2.87 (m, 2H), 2.65 (s, 3H), 1.58 (t, J=7.0 Hz, 3H), 0.83-0.90 (m, 4H), 0.73-0.80 (m, 4H).

Example 54

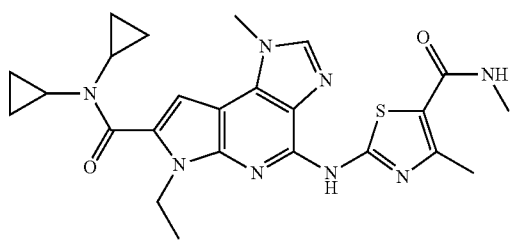 [SMILES: CCn1c(C(=O)N(C2CC2)C2CC2)cc2c3c(ncn3C)c(Nc3nc(C)c(C(=O)NC)s3)nc21]

2-(7-(dicyclopropylcarbamoyl)-6-ethyl-1-methyl-1,
6-dihydroimidazo[4,5-d]pyrrolo[2,3-b]pyridin-4-
ylamino)-N,4-dimethylthiazole-5-carboxamide MS (ESI) m/z 493.1 (M+H).

$^1$H NMR (400 MHz, CDCl$_3$) δ: 7.77 (s, 1H), 6.86 (s, 1H), 5.87-5.94 (m, J=4.6 Hz, 1H), 4.66 (q, J=7.1 Hz, 2H), 4.04 (s, 3H), 3.04 (d, J=4.6 Hz, 3H), 2.79-2.87 (m, 2H), 2.62 (s, 3H), 1.51 (t, J=7.0 Hz, 3H), 0.83-0.90 (m, 4H), 0.73-0.80 (m, 4H).

Example 55

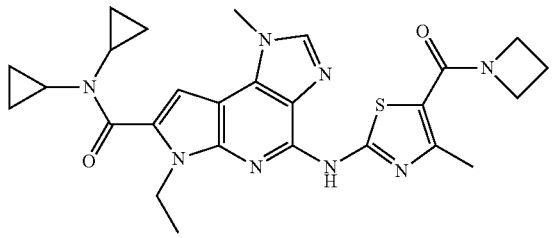 [SMILES: CCn1c(C(=O)N(C2CC2)C2CC2)cc2c3c(ncn3C)c(Nc3nc(C)c(C(=O)N4CCC4)s3)nc21]

4-(5-(azetidine-1-carbonyl)-4-methylthiazol-2-
ylamino)-N,N-dicyclopropyl-6-ethyl-1-methyl-1,6-
dihydroimidazo[4,5-d]pyrrolo[2,3-b]pyridine-7-car-
boxamide MS (ESI) m/z 519.1 (M+H).
$^1$H NMR (400 MHz, CDCl$_3$) δ: 7.73 (s, 1H), 6.90 (s, 1H), 4.73 (q, J=7.0 Hz, 2H), 4.33 (br. s., 4H), 4.05 (s, 3H), 2.80-2.87 (m, 2H), 2.66 (s, 3H), 2.33-2.43 (m, 2H), 1.55 (t, J=7.2 Hz, 3H), 0.83-0.90 (m, 4H), 0.73-0.80 (m, 4H).

Examples 56-70 were synthesized using same procedure as used for 50

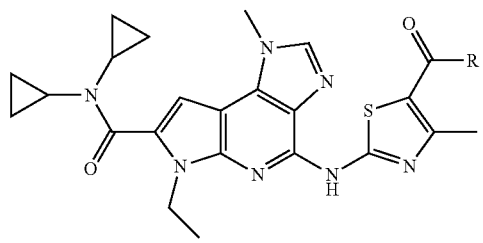

| Ex. No. | R | Name | Retention time ((min) | MS (ESI) m/z |
|---|---|---|---|---|
| 56 | ![piperazinyl] -N(piperazine)N-CH3 | N,N-dicyclopropyl-6-ethyl-1-methyl-4-((4-methyl-5-((4-methyl-1-piperazinyl)carbonyl)-1,3-thiazol-2-yl)amino)-1,6-dihydroimidazo[4,5-d]pyrrolo[2,3-b]pyridine-7-carboxamide | 1.43 | 562.31 |
| 57 | ![morpholinyl] -N(morpholine) | N,N-dicyclopropyl-6-ethyl-1-methyl-4-((4-methyl-5-(4-morpholinyl-carbonyl)-1,3-thiazol-2-yl)amino)-1,6-dihydroimidazo[4,5-d]pyrrolo[2,3-b]pyridine-7-carboxamide | 1.70 | 549.25 |

-continued

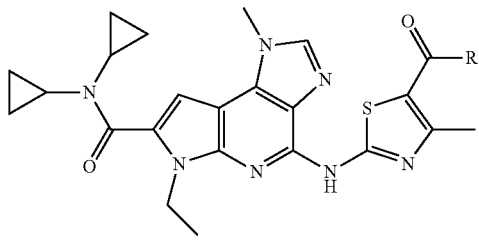

| Ex. No. | R | Name | Retention time ((min) | MS (ESI) m/z |
|---|---|---|---|---|
| 58 | morpholinoethyl-NH- | N,N-dicyclopropyl-6-ethyl-1-methyl-4-((4-methyl-5-((2-(4-morpholinyl)ethyl)carbamoyl)-1,3-thiazol-2-yl)amino)-1,6-dihydroimidazo[4,5-d]pyrrolo[2,3-b]pyridine-7-carboxamide | 1.46 | 592.3 |
| 59 | acetamidoethyl-NH- | 4-((5-((2-acetamidoethyl)carbamoyl)-4-methyl-1,3-thiazol-2-yl)amino)-N,N-dicyclopropyl-6-ethyl-1-methyl-1,6-dihydroimidazo[2,3-b]pyridine-7-carboxamide | 1.51 | 564.27 |
| 60 | cyanomethyl(methyl)N- | 4-((5-((cyanomethyl)(methyl)carbamoyl)-4-methyl-1,3-thiazol-2-yl)amino)-N,N-dicyclopropyl-6-ethyl-1-methyl-1,6-dihydroimidazo[4,5-d]pyrrolo[2,3-b]pyridine-7-carboxamide | 1.78 | 532.25 |
| 61 | cyanomethyl-NH- | 4-((5-((cyanomethyl)carbamoyl)-4-methyl-1,3-thiazol-2-yl)amino)-N,N-dicyclopropyl-6-ethyl-1-methyl-1,6-dihydroimidazo[4,5-d]pyrrolo[2,3-b]pyridine-7-carboxamide | 1.72 | 518.24 |
| 62 | 1,1-dioxidotetrahydrothiophen-3-yl-NH- | N,N-dicyclopropyl-4-((5-((1,1-dioxidotetrahydro-3-thiophenyl)carbamoyl)-4-methyl-1,3-thiazol-2-yl)amino)-6-ethyl-1-methyl-1,6-dihydroimidazo[4,5-d]pyrrolo[2,3-b]pyridine-7-carboxamide | 1.68 | 597.24 |
| 63 | trans-4-hydroxycyclohexyl-NH- | N,N-dicyclopropyl-6-ethyl-4-((5-((trans-4-hydroxycyclohexyl)carbamoyl)-4-methyl-1,3-thiazol-2-yl)amino)-1-methyl-1,6-dihydroimidazo[4,5-d]pyrrolo[2,3-b]pyridine-7-carboxamide | 1.60 | 577.3 |

-continued

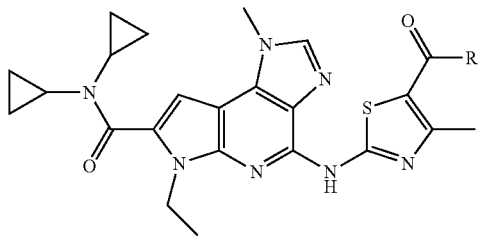

| Ex. No. | R | Name | Retention time ((min)) | MS (ESI) m/z |
|---|---|---|---|---|
| 64 | pyrrolidinyl-3-OH (3S) | N,N-dicyclopropyl-6-ethyl-4-((5-(((3S)-3-hydroxy-1-pyrrolidinyl)carbonyl)-4-methyl-1,3-thiazol-2-yl)amino)-1-methyl-1,6-dihydroimidazo[4,5-d]pyrrolo[2,3-b]pyridine-7-carboxamide | 1.51 | 549.28 |
| 65 | N(CH3)CH2CH2SO2CH3 | N,N-dicyclopropyl-6-ethyl-1-methyl-4-((4-methyl-5-(methyl(2-(methylsulfonyl)ethyl)carbamoyl)-1,3-thiazol-2-yl)amino)-1,6-dihydroimidazo[4,5-d]pyrrolo[2,3-b]pyridine-7-carboxamide | 1.59 | 599.26 |
| 66 | 3-methoxy-azetidinyl | N,N-dicyclopropyl-6-ethyl-4-((5-((3-methoxy-1-azetidinyl)carbonyl)-4-methyl-1,3-thiazol-2-yl)amino)-1-methyl-1,6-dihydroimidazo[4,5-d]pyrrolo[2,3-b]pyridine-7-carboxamide | 1.80 | 549.28 |
| 67 | 3,3-difluorocyclobutyl-NH | N,N-dicyclopropyl-4-((5-(3,3-difluorocyclobutyl)carbamoyl)-4-methyl-1,3-thiazol-2-yl)amino)-6-ethyl-1-methyl-1,6-dihydroimidazo[4,5-d]pyrrolo[2,3-b]pyridine-7-carboxamide | 2.06 | 569.27 |
| 68 | CHF2CH2-NH | N,N-dicyclopropyl-4-((5-((2,2-difluoroethyl)carbamoyl)-4-methyl-1,3-thiazol-2-yl)amino)-6-ethyl-1-methyl-1,6-dihydroimidazo[4,5-d]pyrrolo[2,3-b]pyridine-7-carboxamide | 1.88 | 543.23 |
| 69 | tetrahydropyran-4-yl-NH | N,N-dicyclopropyl-6-ethyl-1-methyl-4-((4-nethyl-5-(tetrahydro-2H-pyran-4-ylcarbamoyl)-1,3-thiazol-2-yl)amino)-1,6-dihydroimidazo[4,5-d]pyrrolo[2,3-b]pyridine-7-carboxamide | 1.87 | 563.26 |
| 70 | thiomorpholinyl-SO2 | N,N-dicyclopropyl-4-((5-((1,1-dioxido-4-thiomorpholinyl)carbonyl)-4-methyl-1,3-thiazol-2-yl)amino)-6-ethyl-1-methyl-1,6-dihydroimidazo[4,5-d]pyrrolo[2,3-b]pyridine-7-carboxamide | 1.66 | 597.26 |

Analysis Condidtions—Column-Mac-Mod Halo 4.6×50 mm 2.7 um; Gradient—4 min from 0% B to 100% B; Flow rate—4 mL/min; Solvent—A=5:95 Acetonitrile:Water; B=90:5 Acetonitrile:Water; Modifier=10 mM NH₄OAc Example 71

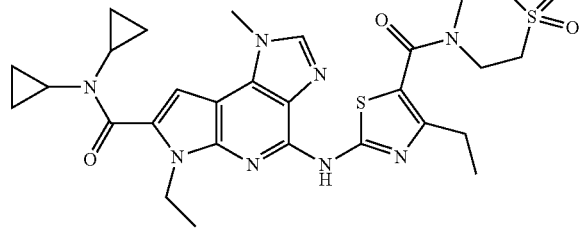

N,N-dicyclopropyl-6-ethyl-4-(4-ethyl-5-(1,1-dioxothiomorpholine-4-carbonyl)thiazol-2-ylamino)-1-methyl-1,6-dihydroimidazo[4,5-d]pyrrolo[2,3-b]pyridine-7-carboxamide 71A Preparation of methyl 247-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylate

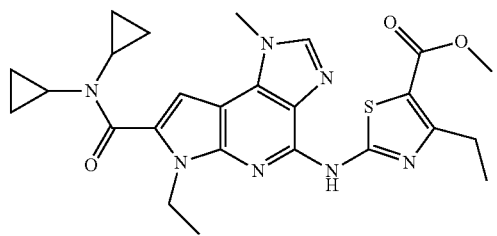 [SMILES: CCc1nc(Nc2nc3c(cc(C(=O)N(C4CC4)C4CC4)n3CC)c3c2ncn3C)sc1C(=O)OC]

To a stirred suspension of N,N-dicyclopropyl-6-ethyl-1-methyl-4-thioureido-1,6-dihydroimidazo[4,5-d]pyrrolo[2,3-b]pyridine-7-carboxamide (103 mg, 0.259 mmol) in EtOH (5 ml) was added freshly prepared methyl 2-bromo-3-oxopentanoate[1] (81 mg, 0.389 mmol) at room temperature. The slurry was then stirred at 65° C. for 2 h. The reaction mixture was then cooled to room temperature and concentrated in vacuo to afford a yellow solid. The solid was then taken up in methylene chloride and washed with saturated aqueous sodium bicarbonate solution. The organic phase was dried over anhydrous magnesium sulfate and concentrated in vacuo. The crude residue was then purified by silica-gel flash chromatography using an Isco 40 g column eluting from 0-5% methanol/methylene chloride to afford methyl 2-(7-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylate (37.5 mg, 28.5% yield) as a white solid.

MS (ESI) m/z 508.4 (M+H)

1H NMR (CDCl₃) δ ppm 9.38 (br s, 1 H), 7.75 (s, 1 H), 6.92 (s, 1 H), 4.76 (q, 2 H, J=6.94 Hz), 4.08 (s, 3H), 3.92 (s, 3H), 3.14 (q, 2H, J=7.68 Hz), 2.85 (m, 2H), 1.59 (t, 3H, J=6.94 Hz), 1.34 (t, 3H, J=7.49 Hz), 0.78-0.91 (m, 8H)

71B Preparation of 2-(7-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylic acid

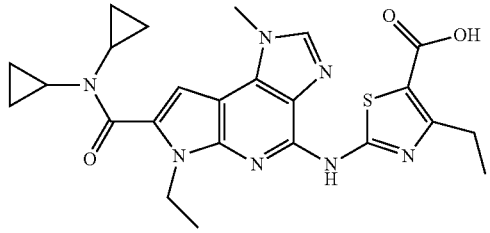 [SMILES: CCc1nc(Nc2nc3c(cc(C(=O)N(C4CC4)C4CC4)n3CC)c3c2ncn3C)sc1C(=O)O]

To a stirred solution of methyl 2-(7-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylate (example 71A, 103 mg, 0.203 mmol) in MeOH (2 mL) was added NaOH (1.420 mL, 1.420 mmol). The solution was then stirred at 65° C. for 18 hrs. The reaction mixture was then cooled to room temperature and concentrated in vacuo to afford yellow slurry. The mixture was then diluted with water, brought to pH 4 with 1N HCl, and the precipitate collected by vacuum filtration. The filtrate was then extracted with CH₂Cl₂; the organic layer was dried over anhydrous magnesium sulfate and concentrated in vacuo. The crude residue was then purified by silica-gel flash chromatography using an Isco 40 g column eluting from 0-8% MeOH/CH₂Cl₂. Desired fractions were combined with the collected precipitate and concentrated to afford 2-(7-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylic acid (126 mg, 126% yield) as an orange/yellow solid.

MS (ESI) m/z 494.2 (M+H)

1H NMR (CDCl₃) δ ppm 8.23 (s, 1 H), 7.28 (s, 1H), 4.62 (q, 2 H, J=6.94 Hz), 4.07 (s, 3H), 3.04 (q, 2H, J=7.49 Hz), 3.00 (m, 2H), 1.42 (t, 3H, J=7.07 Hz), 1.23 (t, 3H, J=7.63 Hz), 0.67-0.79 (m, 8H)

71 Preparation of N,N-dicyclopropyl-6-ethyl-4-(4-ethyl-5-(1,1-dioxothiomorpholine-4-carbonyl)thiazol-2-ylamino)-1-methyl-1,6-dihydroimidazo[4,5-d]pyrrolo[2,3-b]pyridine-7-carboxamide To a stirred solution of 2-(7-(dicyclopropylcarbamoyl)-6-ethyl-1-methyl-1,6-dihydroimidazo[4,5-d]pyrrolo[2,3-b]pyridin-4-ylamino)-4-ethylthiazole-5-carboxylic acid (example 69B, 33 mg, 0.067 mmol), HATU (50.8 mg, 0.134 mmol), 2,6-lutidine (0.020 mL, 0.174 mmol), and DMF (1 mL) was added thiomorpholine 1,1-dioxide (27.1 mg, 0.201 mmol). The solution was then stirred at 50° C. for 1.5 hrs. The reaction was then cooled to room temperature and diluted with methylene chloride. The solution was then washed with saturated aqueous sodium bicarbonate, 10% LiCl in H₂O, and saturated aqueous sodium bicarbonate again. The organic phase was dried over anhydrous magnesium sulfate and concentrated in vacuo. The crude residue was then purified by silica-gel flash chromatography using an Isco 40 g column eluting from 0-6% MeOH/CH₂Cl₂ to give N,N-dicyclopropyl-6-ethyl-4-(4-ethyl-5-(1,1-dioxothiomorpholine-4-carbonyl)thiazol-2-ylamino)-1-methyl-1,6-dihydroimidazo[4,5-d]pyrrolo[2,3-b]pyridine-7-carboxamide (21.7 mg, 52.6% yield) as a pale yellow solid.

MS (ESI) m/z 611.3 (M+H)

1H NMR (CDCl₃) δ ppm 7.68 (s, 1 H), 6.83 (s, 1 H), 4.65 (q, 2 H, J=7.04), 4.13 (m, 4H), 3.99 (s, 3H), 3.05 (m, 4H), 2.76 (m, 2H), 2.68 (q, 2H, J=7.56 Hz), 1.46 (t, 3H, J=7.04 Hz), 1.25 (t, 3H, J=7.59 Hz), 0.68-0.80 (m, 8H)

Example 72

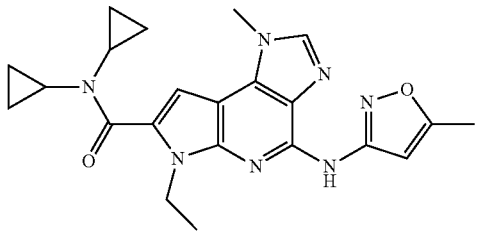 [SMILES: CCn1c(C(=O)N(C2CC2)C2CC2)cc2c3c(ncn3C)c(Nc3cc(C)on3)nc21]

N,N-dicyclopropyl-6-ethyl-1-methyl-4-(5-methyl-isoxazol-3-ylamino)-1,6-dihydroimidazo[4,5-d]pyrrolo[2,3-b]pyridine-7-carboxamide

72A Preparation of 4,4-bis(methylthio)but-3-en-2-one

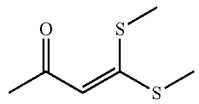

A solution of acetone (2.205 mL, 30.0 mmol) in carbon disulfide (1.81 mL, 30.0 mmol) was added to a suspension of sodium tert-butoxide (5.76 g, 60.0 mmol) in benzene (30 mL) while keeping the reaction temperature not exceeding 10° C. The reaction mixture was stirred at room temperature for 3 h and iodomethane (3.75 mL, 60.0 mmol) was added at 10° C. The resulting reaction mixture was stirred at room temperature overnight. The reaction mixture was diluted with ethyl acetate and washed twice with water. The organic layer was dried over magnesium sulfate, filtered and concentrated in vacuo. The crude product was purified by flash chromatography on silica gel using an automated ISCO system (80 g column, eluting with 10-35% ethyl acetate/hexanes) to give 4,4-bis(methylthio)but-3-en-2-one (3.456 g, 71.0% yield) as a yellow solid.

$^1$H NMR (400 MHz, CDCl$_3$) δ: 6.04 (s, 1H), 2.47 (s, 3H), 2.45 (s, 3H), 2.20 (s, 3H).

72B Preparation of (Z)—N,N-dicyclopropyl-6-ethyl-1-methyl-4-(1-(methylthio)-3-oxobut-1-enylamino)-1,6-dihydroimidazo[4,5-d]pyrrolo[2,3-b]pyridine-7-carboxamide

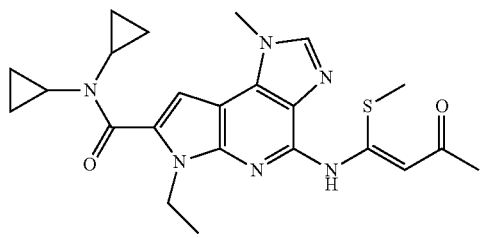 [SMILES: CCn1c(C(=O)N(C2CC2)C2CC2)cc2c3c(ncn3C)c(N/C(=C/C(C)=O)SC)nc21]

Sodium hydride (2.84 g, 71.1 mmol) was added to a solution of 4-amino-N, N-dicyclopropyl-6-ethyl-1-methyl-1,6-dihydroimidazo[4,5-d]pyrrolo[2,3-b]pyridine-7-carboxamide (example 1J, 8.02 g, 23.70 mmol) in DMF (60 mL) and the reaction mixture stirred at room temperature for 1 h. 4,4-bis(methylthio)but-3-en-2-one (example 70A, 5.77 g, 35.5 mmol) in DMF (10 ml) was added and stirring continued for three days. LC/MS showed about 75% completion. The reaction mixture was diluted with ethyl acetate and water was added. An off-white precipitate formed and was collected by filtration to give 5.1 g of product. The filtrate was transferred to a separatory funnel. The layers were separated and the aqueous layer was extracted with dichloromethane (3×50 ml), the combined organic layers were washed with saturated sodium bicarbonate and dried over magnesium sulfate, filtered and concentrated in vacuo. The crude product was purified by flash chromatography on silica gel using an ISCO system (220 g column, eluting with 2-8% methanol/dichloromethane) to give (Z)—N,N-dicyclopropyl-6-ethyl-1-methyl-4-(1-(methylthio)-3-oxobut-1-enylamino)-1,6-dihydroimidazo[4,5-d]pyrrolo[2,3-b]pyridine-7-carboxamide (6.6 g, 61.5% yield) along with 2.2 g of recovered 1J.

MS (ESI) m/z 453.3 (M+H).

$^1$H NMR (400 MHz, DMSO-d$_6$) δ: 14.42 (s, 1H), 8.16 (s, 1H), 7.24 (s, 1H), 5.54 (s, 1H), 4.52 (q, J=7.0 Hz, 2H), 4.05 (s, 3H), 2.89-2.97 (m, 2H), 2.43 (s, 3H), 2.14 (s, 3H), 1.34 (t, J=7.0 Hz, 3H), 0.71-0.80 (m, 4H), 0.63-0.70 (m, 4H).

72 Preparation of N,N-dicyclopropyl-6-ethyl-1-methyl-4-(5-methylisoxazol-3-ylamino)-1,6-dihydroimidazo[4,5-d]pyrrolo[2,3-b]pyridine-7-carboxamide A mixture of (Z)—N,N-dicyclopropyl-6-ethyl-1-methyl-4-(1-(methylthio)-3-oxobut-1-enylamino)-1,6-dihydroimidazo[4,5-d]pyrrolo[2,3-b]pyridine-7-carboxamide (22 mg, 0.049 mmol) and hydroxylamine (50% aqueous solution, 3.13 µL, 0.051 mmol) in ethanol (1 mL) was heated at reflux for 3 h and LC/MS showed completion of reaction. The reaction mixture was diluted with methanol and purified by preparative HPLC to furnish N,N-dicyclopropyl-6-ethyl-1-methyl-4-(5-methylisoxazol-3-ylamino)-1,6-dihydroimidazo[4,5-d]pyrrolo[2,3-b]pyridine-7-carboxamide (9 mg, 43.3% yield) as a white solid.

MS (ESI) m/z 420.1 (M+H).

$^1$H NMR (400 MHz, METHANOL-d$_4$) δ: 8.45 (s, 1H), 7.26 (s, 1H), 6.58 (s, 1H), 4.63 (q, J=7.2 Hz, 2H), 4.17 (s, 3H), 2.94-3.02 (m, 2H), 2.33 (s, 3H), 1.47 (t, J=7.2 Hz, 3H), 0.85-0.92 (m, 4H), 0.77-0.84 (m, 4H).

Example 73

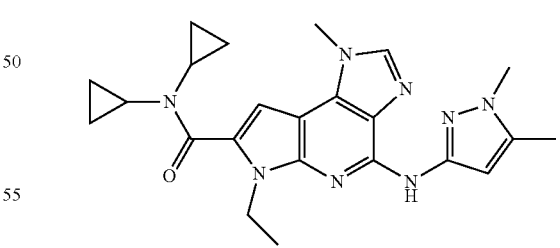

N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide A mixture of (Z)—N,N-dicyclopropyl-6-ethyl-1-methyl-4-(1-(methylthio)-3-oxobut-1-enylamino)-1,6-dihydroimidazo[4,5-d]pyrrolo[2,3-b]pyridine-7-carboxamide (example 72B, 70 mg, 0.155 mmol) and tert-butyl 1-methylhydrazinecarboxylate (0.046 mL, 0.309 mmol) in acetic acid (1 mL) wan stirred at 35° C. for 4 h (monitored by LC/MS until no starting material left). Formic acid (0.5 mL) was added and stirred at 60° C. for 6 h. Solvent was evaporated and the crude product was purified by flash chromatography on silica gel using an automated ISCO system (12 g column, eluting with 2-10% methanol/dichloromethane). The impure product was further purified by preparative HPLC to give N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide (45 mg, 63.9% yield) as an off-white solid.

MS (ESI) m/z 433.2 (M+H).

$^1$H NMR (500 MHz, CDCl$_3$) δ: 8.19 (s, 1H), 7.63 (s, 1H), 6.94 (s, 1H), 6.85 (s, 1H), 4.65 (q, J=7.0 Hz, 2H), 3.99 (s, 3H), 3.71 (s, 3H), 2.79-2.85 (m, 2H), 2.33 (s, 3H), 1.49 (t, J=7.2 Hz, 3H), 0.82-0.87 (m, 4H), 0.72-0.78 (m, 4H)

Alternative Synthesis of Example 73

73A Preparation of 4-iodo-N,N-dicyclopropyl-6-ethyl-1-methyl-1,6-dihydroimidazo[4,5-d]pyrrolo[2,3-b]pyridine-7-carboxamide

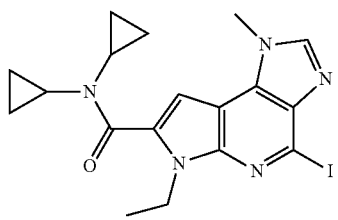 [SMILES: CCn1c(C(=O)N(C2CC2)C2CC2)cc2c3c(ncn3C)c(I)nc21]

To a stirred suspension of 4-amino-N,N-dicyclopropyl-6-ethyl-1-methyl-1,6-dihydroimidazo[4,5-d]pyrrolo[2,3-b]pyridine-7-carboxamide (34.4 mg, 0.102 mmol) in diiodomethane (102 μL) at 60° C. was slowly added isoamyl nitrite (27.4 μL, 0.203 mmol). The reaction mixture was stirred at 60° C. 5 h. After cooling to rt, the reaction mixture was diluted with dichloromethane. Saturated aqueous sodium bicarbonate was added and the aqueous layer was extracted with dichloromethane (3×). The combined organics were dried over anhydrous sodium sulfate, filtered and concentrated in vacuo. The crude residue was placed on the pump for 16 h to remove any additional diiodomethane. LCMS was deemed pure enough to be carried forward crude. The product was used immediately in the next reaction.

MS (ESI) m/z 450.1 (M+H)

73 Preparation of N,N-dicyclopropyl-6-ethyl-1-methyl-4-(1,5-dimethyl-1H-pyrazol-3-ylamino)-1,6-dihydroimidazo[4,5-d]pyrrolo[2,3-b]pyridine-7-carboxamide To a vial containing 1,5-dimethyl-1H-pyrazol-3-amine (13.60 mg, 0.122 mmol), Pd$_2$(dba)$_3$ (4.67 mg, 5.10 μmol), Xantphos (5.90 mg, 10.20 μmol), and cesium carbonate (100 mg, 0.306 mmol) was added N,N-dicyclopropyl-6-ethyl-4-iodo-1-methyl-1,6-dihydroimidazo[4,5-d]pyrrolo[2,3-b]pyridine-7-carboxamide (45.8 mg, 0.102 mmol) in DME (1020 μL). The reaction mixture was sparged with argon for 5 min, the vial was capped, and the reaction mixture was heated at 90° C. 1 h. The reaction mixture was diluted with dichloromethane and vacuum filtered through Celite. The filtrate was concentrated in vacuo. The crude residue was purified via flash column chromatography using an ISCO 12 g column eluting with 1-10% MeOH/CH$_2$Cl$_2$). N,N-Dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide (14 mg, 31.7% yield) was isolated as an off-white solid.

MS (ESI) m/z 433.2 (M+H).

$^1$H NMR (500 MHz, CDCl$_3$) δ: 8.19 (s, 1H), 7.63 (s, 1H), 6.94 (s, 1H), 6.85 (s, 1H), 4.65 (q, J=7.0 Hz, 2H), 3.99 (s, 3H), 3.71 (s, 3H), 2.79-2.85 (m, 2H), 2.33 (s, 3H), 1.49 (t, J=7.2 Hz, 3H), 0.82-0.87 (m, 4H), 0.72-0.78 (m, 4H)

Example 74

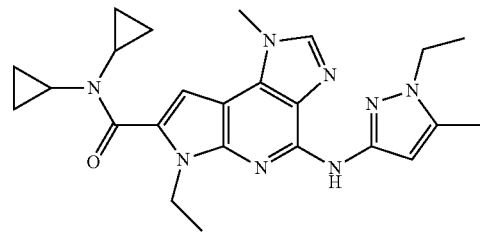

N,N-dicyclopropyl-6-ethyl-4-(1-ethyl-5-methyl-1H-pyrazol-3-ylamino)-1-methyl-1,6-dihydroimidazo[4,5-d]pyrrolo[2,3-b]pyridine-7-carboxamide 74A Preparation of tert-butyl 1,3-dioxoisoindolin-2-yl(ethyl)carbamate

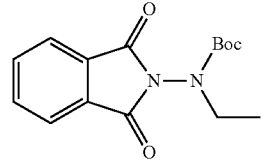 [SMILES: CCN(C(=O)OC(C)(C)C)N1C(=O)c2ccccc2C1=O]

Diisopropyl azodicarboxylate (2.92 mL, 15.00 mmol) was added in one portion to a solution of tert-butyl 1,3-dioxoisoindolin-2-ylcarbamate (2.62 g, 10 mmol, prepared following the procedure described by Nicolas Brosse et al. in *Eur. J. Org. Chem.* 4757-4764, 2003), triphenylphosphine (3.93 g, 15.00 mmol) and ethanol (0.691 g, 15.00 mmol) in THF (20 mL) at 0° C. and the reaction solution was stirred at room temperature for 1 h (monitored by TLC until completion). Solvent was evaporated and the residue was purified by flash chromatography on silica gel using an automated ISCO system (80 g column, eluting with 5-35% ethyl acetate/hexanes) to provide tert-butyl 1,3-dioxoisoindolin-2-yl(ethyl)carbamate (2.6 g, 90% yield) as a white solid which was used as it in the next step 74B Preparation of tert-butyl 1-ethylhydrazinecarboxylate

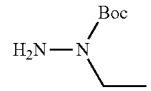

Methylhydrazine (1.415 mL, 26.9 mmol) was added to a solution of tert-butyl 1,3-dioxoisoindolin-2-yl(ethyl)carbamate (example 74A, 5.2 g, 17.91 mmol) in THF (40 mL) at 0° C. and the reaction mixture was stirred at room temperature overnight. A white precipitate formed and was filtered off through a pad of Celite, The filtrate was concentrated in vacuo. The residue was dissolved in ethyl acetate (50 ml) and extracted with 1N HCl (3×30 ml), the acid layer was washed with ethyl acetate (50 ml) and basified to pH 10 by addition of 20% NaOH. The basic solution was then extracted with ethyl acetate (3×50 ml) and the combined organic layers were washed with brine, dried over magnesium sulfate, filtered and concentrated in vacuo to give tert-butyl 1-ethylhydrazinecarboxylate (2.5 g, 87% yield) as colorless oil.

$^1$H NMR (400 MHz, CDCl$_3$) δ: 3.90 (br. s., 2H), 3.35 (q, J=7.0 Hz, 2H), 1.42 (s, 9H), 1.07 (t, J=7.0 Hz, 3H)

74 Preparation of N,N-dicyclopropyl-6-ethyl-4-(1-ethyl-5-methyl-1H-pyrazol-3-ylamino)-1-methyl-1,6-dihydroimidazo[4,5-d]pyrrolo[2,3-b]pyridine-7-carboxamide A mixture of (Z)—N,N-dicyclopropyl-6-ethyl-1-methyl-4-(1-(methylthio)-3-oxobut-1-enylamino)-1,6-dihydroimidazo[4,5-d]pyrrolo[2,3-b]pyridine-7-carboxamide (example 74B, 70 mg, 0.155 mmol) and tert-butyl 1-ethylhydrazinecarboxylate (49.6 mg, 0.309 mmol) in acetic acid (1 mL) wan stirred at 35° C. for 4 h (monitored by LC/MS until no starting material left). Formic acid (1 mL) was added and the reaction mixture stirred at 60° C. for 6 h. The solvent was evaporated and the crude product was purified by flash chromatography on silica gel using an automated ISCO system (12 g column, eluting with 2-10% methanol/dichloromethane). The material was further purified by preparative HPLC to afford N,N-dicyclopropyl-6-ethyl-4-(1-ethyl-5-methyl-1H-pyrazol-3-ylamino)-1-methyl-1,6-dihydroimidazo[4,5-d]pyrrolo[2,3-b]pyridine-7-carboxamide (38 mg, 53.4% yield) as an off-white solid.

MS (ESI) m/z 447.3 (M+H).
$^1$H NMR (500 MHz, CDCl$_3$) δ: 8.08 (s, 1H), 7.61 (s, 1H), 6.93 (s, 1H), 6.84 (s, 1H), 4.66 (q, J=7.1 Hz, 2H), 4.02 (q, J=7.2 Hz, 2H), 3.98 (s, 3H), 2.79-2.85 (m, 2H), 2.34 (s, 3H), 1.49 (t, J=7.1 Hz, 3H), 1.41 (t, J=7.2 Hz, 3H), 0.82-0.87 (m, 4H), 0.72-0.78 (m, 4H).

Example 75

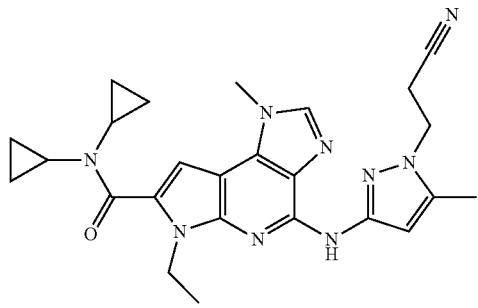 [SMILES: CCn1c(C(=O)N(C2CC2)C2CC2)cc2c3c(ncn3C)c(Nc3cc(C)n(CCC#N)n3)nc21]

4-(1-(2-cyanoethyl)-5-methyl-1H-pyrazol-3-ylamino)-N,N-dicyclopropyl-6-ethyl-1-methyl-1,6-dihydroimidazo[4,5-d]pyrrolo[2,3-b]pyridine-7-carboxamide The title compound was prepared using a method analogous to that used to prepare example 74.
MS (ESI) m/z 472.2 (M+H).
$^1$H NMR (400 MHz, CDCl$_3$) δ: 8.05 (s, 1H), 7.64 (s, 1H), 6.99 (s, 1H), 6.85 (s, 1H), 4.65 (q, J=7.0 Hz, 2H), 4.25 (t, J=6.8 Hz, 2H), 4.01 (s, 3H), 2.92 (t, J=6.7 Hz, 2H), 2.79-2.86 (m, 2H), 2.41 (s, 3H), 1.49 (t, J=7.2 Hz, 3H), 0.82-0.88 (m, 4H), 0.72-0.80 (m, 4H).

Example 76

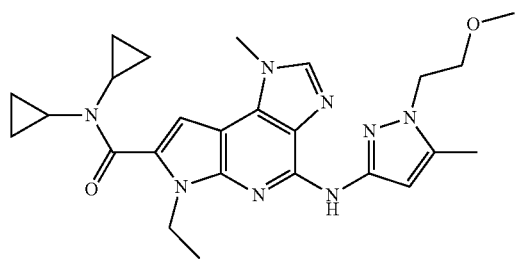 [SMILES: CCn1c(C(=O)N(C2CC2)C2CC2)cc2c3c(ncn3C)c(Nc3cc(C)n(CCOC)n3)nc21]

N,N-dicyclopropyl-6-ethyl-4-(1-(2-methoxyethyl)-5-methyl-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 74.
MS (ESI) m/z 477.2 (M+H).
$^1$H NMR (500 MHz, CDCl$_3$) δ: 8.09 (s, 1H), 7.61 (s, 1H), 6.94 (s, 1H), 6.84 (s, 1H), 4.66 (q, J=6.8 Hz, 2H), 4.12 (t, J=5.5 Hz, 2H), 3.98 (s, 3H), 3.74 (t, J=5.8 Hz, 2H), 3.32 (s, 3H), 2.78-2.86 (m, 2H), 2.36 (s, 3H), 1.49 (t, J=7.1 Hz, 3H), 0.81-0.89 (m, 4H), 0.71-0.80 (m, 4H).

Example 77

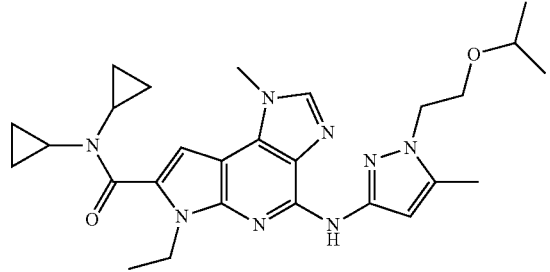 [SMILES: CCn1c(C(=O)N(C2CC2)C2CC2)cc2c3c(ncn3C)c(Nc3cc(C)n(CCOC(C)C)n3)nc21]

N,N-dicyclopropyl-6-ethyl-4-(1-(2-isopropoxyethyl)-5-methyl-1H-pyrazol-3-ylamino)-1-methyl-1,6-dihydroimidazo[4,5-d]pyrrolo[2,3-b]pyridine-7-carboxamide 77A Preparation of 2-isopropoxyethyl methanesulfonate

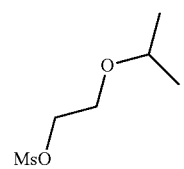

A round bottom flask was charged with 2-isopropoxyethanol (0.5 mL, 4.34 mmol) and dichloromethane (21.68 mL) and was cooled to 0° C. Triethylamine (1.208 mL, 8.67 mmol)

was added along with a tip of DMAP. Methanesulfonyl chloride (0.338 mL, 4.34 mmol) was added dropwise. The reaction mixture was slowly warmed to rt over 2 h. The reaction mixture was quenched with saturated aqueous ammonium chloride and transferred to a separatory funnel The aqueous layer was extracted with dichloromethane (2×). The combined organics were washed with brine, dried over anhydrous sodium sulfate, filtered and concentrated in vacuo. 2-Isopropoxyethyl methanesulfonate (1 g) was isolated as a clear oil and was immediately used in the next reaction.

1H NMR (400 MHz, CHLOROFORM-d) δ ppm 4.34-4.40 (m, 2H), 3.67-3.71 (m, 2H), 3.60-3.67 (m, 1H), 3.07 (s, 3H), 1.18 (d, 6H, J=8.0 Hz)

77B Preparation of tert-butyl 1,3-dioxoisoindolin-2-yl(2-isopropoxyethyl)carbamate

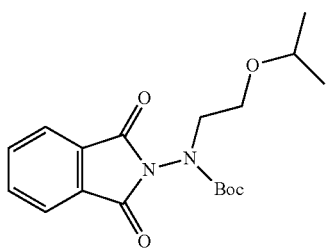 [SMILES: CC(C)OCCN(C(=O)OC(C)(C)C)N1C(=O)c2ccccc2C1=O]

A round bottom flask charged with 2-isopropoxyethyl methanesulfonate (example 77A, 0.791 g, 4.34 mmol) in acetonitrile (21.70 mL) was stirred under an atmosphere of nitrogen. tert-Butyl 1,3-dioxoisoindolin-2-ylcarbamate (1.138 g, 4.34 mmol) was added along with potassium carbonate (2.399 g, 17.36 mmol) and benzyltriethylammonium chloride (0.198 g, 0.868 mmol). The reaction mixture was heated at 50° C. 24 h and cooled to rt over the weekend. The reaction mixture was diluted with ethyl acetate and water. The aqueous layer was extracted with ethyl acetate. The combined organics were washed with brine, dried over anhydrous sodium sulfate, vacuum filtered through a plug of silica gel and concentrated in vacuo. The crude oil was used without additional purification (1.26 g, 83% yield).

MS (ESI) m/z 249.2 (M-$C_4H_9CO_2$)

1H NMR (400 MHz, CHLOROFORM-d) as a mixture of rotomers δ ppm 1H NMR (400 MHz, CHLOROFORM-d) d ppm 7.86-7.94 (m, 2 H), 7.73-7.82 (m, 2 H), 3.79-3.90 (m, 2 H), 3.58-3.66 (m, 2 H), 3.41-3.55 (m, 1 H), 1.31-1.56 (m, 9 H), 0.87-1.05 (m, 6 H)

77C Preparation of tert-butyl 1-(2-isopropoxyethyl)hydrazinecarboxylate

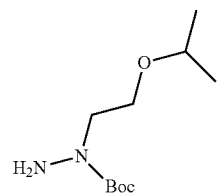

To a solution of tert-butyl 1,3-dioxoisoindolin-2-yl(2-isopropoxyethyl)carbamate (example 77B, 1.262 g, 3.62 mmol) in tetrahydrofuran (24.15 mL) at 0° C. was slowly added methylhydrazine (0.289 mL, 5.43 mmol). The reaction mixture was stirred at 0° C. for 3 h. The reaction mixture was filtered to remove the white precipitate and the filtrate was concentrated in vacuo. The semisolid was triturated with ethyl acetate (2×) and the triturant was concentrated in vacuo. This process was repeated to ultimately provide tert-butyl 1-(2-isopropoxyethyl)hydrazinecarboxylate (0.665 g, 84% yield) as a yellow oil.

1H NMR (400 MHz, CHLOROFORM-d) δ ppm 3.52-3.65 (m, 5 H), 1.48 (s, 9 H), 1.15 (d, 6 H, J=6.27 Hz)

77 Preparation of N,N-dicyclopropyl-6-ethyl-4-(1-(2-isopropoxyethyl)-5-methyl-1H-pyrazol-3-ylamino)-1-methyl-1,6-dihydroimidazo[4,5-d]pyrrolo[2,3-b]pyridine-7-carboxamide This compound was prepared according to example 73 using tert-butyl 1-(2-isopropoxyethyl)hydrazinecarboxylate (example 77C, 29.8 mg, 0.137 mmol) to provide N,N-dicyclopropyl-6-ethyl-4-(1-(2-isopropoxyethyl)-5-methyl-1H-pyrazol-3-ylamino)-1-methyl-1,6-dihydroimidazo[4,5-d]pyrrolo[2,3-b]pyridine-7-carboxamide (16.72 mg, 48.7% yield) as a white solid.

MS (ESI) m/z 505.4 (M+H)

1H NMR (400 MHz, CHLOROFORM-d) δ ppm 7.89 (s, 1 H), 6.99 (s, 1 H), 6.88 (s, 1H), 4.65 (q, 2 H, J=7.03 Hz), 4.22 (t, 2H, J=5.27 Hz), 4.06 (s, 3 H), 3.78 (t, 2H, J=5.27 Hz), 3.52 (dt, 1H, J=12.11, 6.12 Hz), 2.79-2.88 (m, 2 H), 2.41 (s, 3H), 1.50 (t, 3 H, J=7.03 Hz), 1.09 (d, 6H, J=6.27 Hz), 0.82-0.91 (m, 4 H), 0.71-0.81 (m, 4 H)

Example 78

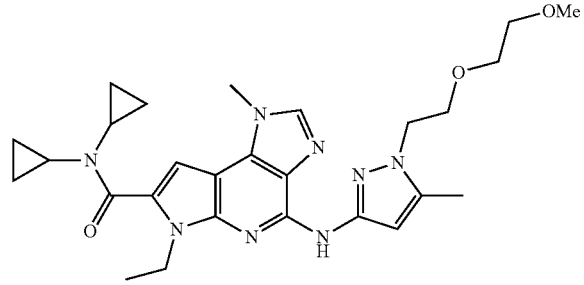 [SMILES: CCn1c(C(=O)N(C2CC2)C2CC2)cc2c3c(ncn3C)c(Nc3cc(C)n(CCOCCOC)n3)nc21]

N,N-dicyclopropyl-6-ethyl-4-(1-(2-(2-methoxyethoxy)ethyl)-5-methyl-1H-pyrazol-3-ylamino)-1-methyl-1,6-dihydroimidazo[4,5-d]pyrrolo[2,3-b]pyridine-7-carboxamide

78A Preparation of tert-butyl 1,3-dioxoisoindolin-2-yl(2-(2-methoxyethoxy)ethyl)carbamate

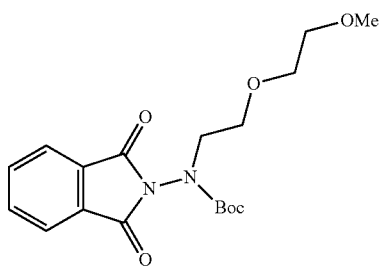 [SMILES: COCCOCCN(C(=O)OC(C)(C)C)N1C(=O)c2ccccc2C1=O]

The compound was prepared according to Example 77B using 1-bromo-2-(2-methoxyethoxy)ethane (0.259 mL, 1.906 mmol) to provide tert-butyl 1,3-dioxoisoindolin-2-yl (2-(2-methoxyethoxy)ethyl)carbamate (0.583 g, 84% yield) as a pale yellow oil.

MS (ESI) m/z 265.2 (M-C$_4$H$_9$CO$_2$)

1H NMR (400 MHz, CHLOROFORM-d) as a mixture of rotomers δ ppm 7.85-7.94 (m, 2 H), 7.73-7.82 (m, 2 H), 3.83-3.93 (m, 2 H), 3.67-3.74 (m, 2 H), 3.48-3.59 (m, 2 H), 3.30-3.43 (m, 2 H), 3.16-3.28 (m, 3 H), 1.29-1.55 (m, 9 H)

78B Preparation of tert-butyl 1-(2-(2-ethoxyethoxy)ethyl)hydrazinecarboxylate

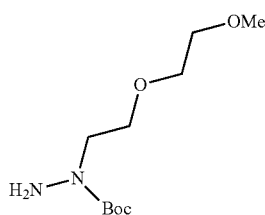 [SMILES: COCCOCCN(N)C(=O)OC(C)(C)C]

The compound was prepared according to example 77C using tert-butyl 1,3-dioxoisoindolin-2-yl(2-(2-methoxyethoxy)ethyl)carbamate (0.583 g, 1.600 mmol) to provide tert-butyl 1-(2-(2-methoxyethoxy)ethyl)hydrazinecarboxylate (0.4 g, 107% yield) as a yellow oil.

1H NMR (400 MHz, CHLOROFORM-d) δ ppm 3.51-3.70 (m, 8 H), 3.39 (s, 3 H), 1.48 (s, 9 H)

78 Preparation of N,N-dicyclopropyl-6-ethyl-4-(1-(2-(2-methoxyethoxy)ethyl)-5-methyl-1H-pyrazol-3-ylamino)-1-methyl-1,6-dihydroimidazo[4,5-d]pyrrolo[2,3-b]pyridine-7-carboxamide This compound was prepared according to example 74 using tert-butyl 1-(2-(2-methoxyethoxy)ethyl)hydrazinecarboxylate (example 78B, 43.2 mg, 0.184 mmol) to provide N,N-dicyclopropyl-6-ethyl-4-(1-(2-(2-methoxyethoxy)ethyl)-5-methyl-1H-pyrazol-3-ylamino)-1-methyl-1,6-dihydroimidazo[4,5-d]pyrrolo[2,3-b]pyridine-7-carboxamide (17.34 mg, 36% yield) as a white solid.

MS (ESI) m/z 521.4 (M+H)

1H NMR (400 MHz, CHLOROFORM-d) δ ppm 7.85 (br s, 1 H), 6.91 (s, 1 H), 6.87 (s, 1H), 4.65 (q, 2 H, J=7.03 Hz), 4.20 (t, 2H, J=5.27 Hz), 4.05 (s, 3 H), 3.87 (t, 2H, J=5.65 Hz), 3.53-3.59 (m, 2H), 3.50 (ddd, 2H, J=5.40, 2.89, 2.76 Hz), 2.77-2.87 (m, 2 H), 2.38 (s, 3H), 1.50 (t, 3 H, J=7.03 Hz), 0.82-0.91 (m, 4 H), 0.71-0.79 (m, 4 H)

Example 79

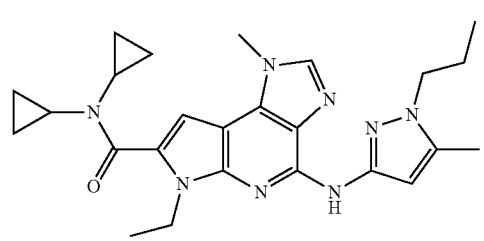 [SMILES: CCCn1nc(Nc2nc3c(cc(C(=O)N(C4CC4)C4CC4)n3CC)c3c2ncn3C)cc1C]

Preparation of N,N-dicyclopropyl-6-ethyl-1-methyl-4-(5-methyl-1-propyl-1H-pyrazol-3-ylamino)-1,6-dihydroimidazo[4,5-d]pyrrolo[2,3-b]pyridine-7-carboxamide

79A Preparation of tert-butyl 1-propylhydrazinecarboxylate

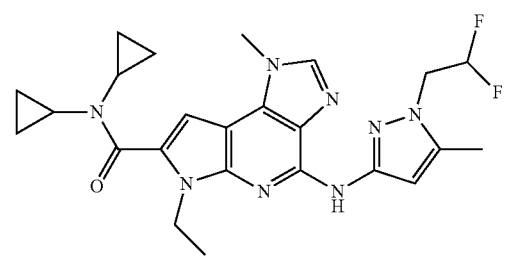 [SMILES: CCn1c(C(=O)N(C2CC2)C2CC2)cc2c3c(ncn3C)c(Nc3cc(C)n(CC(F)F)n3)nc21]

To a solution of propylhydrazine, oxalic acid salt (0.5 g, 3.05 mmol) in ethanol (3 mL) in a round bottom flask under nitrogen was added triethylamine (0.425 mL, 3.05 mmol). The reaction mixture was cooled to 0° C. and BOC$_2$O (0.707 mL, 3.05 mmol) dissolved in ethanol (1 mL) was added dropwise over 10 min. The reaction mixture was allowed to warm to room temperature for 16 h. Ethanol was removed by concentration in vacuo. The residue was taken up in water and ethyl acetate. The aqueous layer was extracted with ethyl acetate (3×). The combined organics were dried over anhydrous sodium sulfate, filtered and concentrated in vacuo. The crude product was used as such in the next reaction.

1H NMR (400 MHz, CHLOROFORM-d) δ ppm 3.30-3.36 (m, 2 H), 1.59 (dq, 3 H, J=14.40, 7.33 Hz), 1.48 (s, 9 H), 0.88 (t, 3 H, J=7.40 Hz)

79 Preparation of N,N-dicyclopropyl-6-ethyl-1-methyl-4-(5-methyl-1-propyl-1H-pyrazol-3-ylamino)-1,6-dihydroimidazo[4,5-d]pyrrolo[2,3-b]pyridine-7-carboxamide This compound was prepared according to example 74 using tert-butyl 1-propylhydrazinecarboxylate (example 79A, 19.87 mg, 0.114 mmol) to provide N,N-dicyclopropyl-6-ethyl-1-methyl-4-(5-methyl-1-propyl-1H-pyrazol-3-ylamino)-1,6-dihydroimidazo[4,5-d]pyrrolo[2,3-b]pyridine-7-carboxamide (15.6 mg, 59% yield) as a white solid.

MS (ESI) m/z 461.4 (M+H)

1H NMR (400 MHz, CHLOROFORM-d) δ ppm 7.74 (br s, 1 H), 6.92 (s, 1 H), 6.86 (s, 1 H), 4.66 (q, 2 H, J=7.11 Hz), 4.03 (s, 3 H), 3.95 (t, 2 H, J=7.15 Hz), 2.78-2.87 (m, 2 H), 2.34 (s, 3 H), 1.87 (dq, 3 H, J=14.49, 7.30 Hz), 1.50 (t, 3 H, J=7.15 Hz), 0.96 (t, 3 H, J=7.40 Hz), 0.83-0.89 (m, 4 H), 0.72-0.79 (m, 4 H)

Example 80

N,N-dicyclopropyl-4-(1-(2,2-difluoroethyl)-5-methyl-1H-pyrazol-3-ylamino)-6-ethyl-1-methyl-1,6-dihydroimidazo[4,5-d]pyrrolo[2,3-b]pyridine-7-carboxamide 80A Preparation of tert-butyl 2,2-difluoroethyl(1,3-dioxoisoindolin-2-yl)carbamate

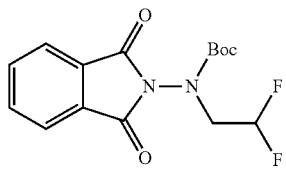 [SMILES: CC(C)(C)OC(=O)N(CC(F)F)N1C(=O)c2ccccc2C1=O]

The title compound was prepared using a method analogous to that used to prepare example 77A.

80B Preparation of tert-butyl 1-(2,2-difluoroethyl)hydrazinecarboxylate

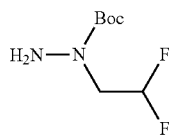

The title compound was prepared using a method analogous to that used to prepare example 77B.
¹H NMR (400 MHz, CHLOROFORM-d) δ: 5.94 (tt, J=56.3, 4.4 Hz, 1H), 3.74 (td, J=13.8, 4.4 Hz, 2H), 1.48 (s, 9H)

80 Preparation of N,N-dicyclopropyl-4-(1-(2,2-difluoroethyl)-5-methyl-1H-pyrazol-3-ylamino)-6-ethyl-1-methyl-1,6-dihydroimidazo[4,5-d]pyrrolo[2,3-b]pyridine-7-carboxamide The title compound was prepared using a method analogous to that used to prepare example 73.
MS (ESI) m/z 483.3 (M+H).
¹H NMR 500 MHz, (CHLOROFORM-d) δ: 8.17 (br. s., 1H), 7.66 (s, 1H), 7.01 (s, 1H), 6.85 (s, 1H), 6.05 (tt, J=56.0, 4.4 Hz, 1H), 4.65 (q, J=6.9 Hz, 2H), 4.30 (td, J=13.2, 4.3 Hz, 2H), 3.99 (s, 3H), 2.79-2.86 (m, 2H), 2.36 (s, 3H), 1.49 (t, J=7.1 Hz, 3H), 0.81-0.88 (m, 4H), 0.72-0.79 (m, 4H).

Example 81

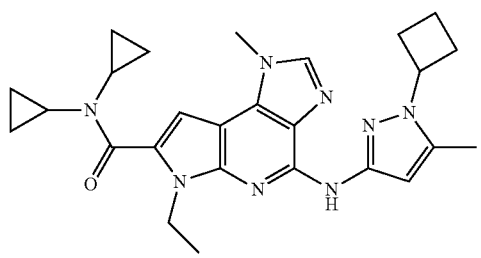 [SMILES: CCn1c(C(=O)N(C2CC2)C2CC2)cc2c3c(ncn3C)c(Nc3cc(C)n(C4CCC4)n3)nc21]

4-(1-cyclobutyl-5-methyl-1H-pyrazol-3-ylamino)-N,N-dicyclopropyl-6-ethyl-1-methyl-1,6-dihydroimidazo[4,5-d]pyrrolo[2,3-b]pyridine-7-carboxamide 81A Preparation of tert-butyl 1-cyclobutylhydrazinecarboxylate

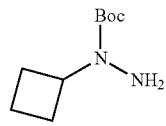

The title compound was prepared following the procedure described by So Ok Park et al. in J. Comb. Chem. 11, 315-326, 2009.

81 Preparation of 4-(1-cyclobutyl-5-methyl-1H-pyrazol-3-ylamino)-N,N-dicyclopropyl-6-ethyl-1-methyl-1,6-dihydroimidazo[4,5-d]pyrrolo[2,3-b]pyridine-7-carboxamide The title compound was prepared using a method analogous to that used to prepare example 73.
MS (ESI) m/z 473.4 (M+H).
¹H NMR (500 MHz, CHLOROFORM-d) δ: 8.05 (s, 1H), 6.91 (s, 1H), 6.79 (s, 1H), 4.68 (quin, J=8.4 Hz, 1H), 4.61 (q, J=7.1 Hz, 2H), 4.07 (s, 3H), 2.80-2.87 (m, 2H), 2.69-2.79 (m, 2H), 2.37-2.47 (m, 2H), 2.32 (s, 3H), 1.78-1.98 (m, 2H), 1.47 (t, J=7.1 Hz, 3H), 0.82-0.91 (m, 4H), 0.72-0.80 (m, 4H).

Example 82

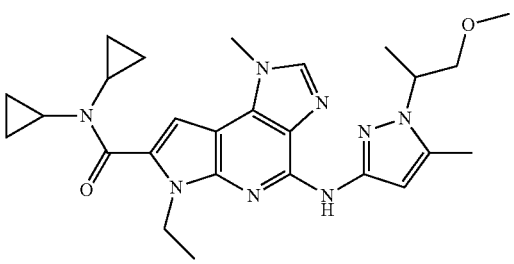 [SMILES: CCn1c(C(=O)N(C2CC2)C2CC2)cc2c3c(ncn3C)c(Nc3cc(C)n(C(C)COC)n3)nc21]

N,N-dicyclopropyl-6-ethyl-4-(1-(1-methoxypropan-2-yl)-5-methyl-1H-pyrazol-3-ylamino)-1-methyl-1,6-dihydroimidazo[4,5-d]pyrrolo[2,3-b]pyridine-7-carboxamide Prepared as described in example 77.
MS (ESI) m/z 491 (M+H).
1H NMR (400 MHz, CHLOROFORM-d) δ ppm 8.18 (br. s., 1 H) 7.63 (s, 1 H) 6.93 (s, 1 H) 6.85 (s, 1 H) 4.66 (q, J=7.04 Hz, 2 H) 4.29-4.48 (m, J=13.31, 6.82, 6.82, 6.71 Hz, 1 H) 4.00 (s, 3 H) 3.55-3.79 (m, 2 H) 3.29 (s, 3 H) 2.72-2.92 (m, 2 H) 2.36 (s, 3 H) 1.49 (t, J=7.04 Hz, 3 H) 1.46 (d, J=6.82 Hz, 2 H) 0.68-0.93 (m, 8 H).

Example 83

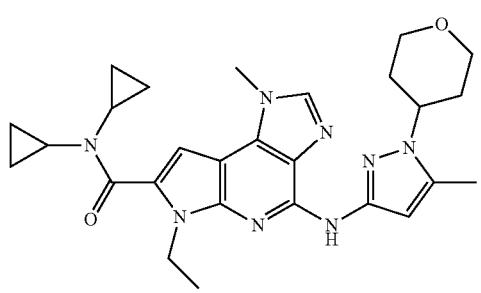 [SMILES: CCn1c(C(=O)N(C2CC2)C2CC2)cc2c3c(ncn3C)c(Nc3cc(C)n(C4CCOCC4)n3)nc21]

N,N-dicyclopropyl-6-ethyl-1-methyl-4-(5-methyl-1-(tetrahydro-2H-pyran-4-yl)-1H-pyrazol-3-ylamino)-1,6-dihydroimidazo[4,5-d]pyrrolo[2,3-b]pyridine-7-carboxamide Prepared using similar procedure as for example 77.

MS (ESI) m/z 503 (M+H).

1H NMR (500 MHz, CHLOROFORM-d) δ ppm 8.12 (s, 1 H) 7.64 (s, 1 H) 6.95 (s, 1 H) 6.86 (s, 1 H) 4.66 (q, J=7.21 Hz, 2 H) 4.09-4.23 (m, 3 H) 4.01 (s, 3 H) 3.55 (td, J=12.00, 1.80 Hz, 2 H) 2.73-2.89 (m, 2 H) 2.37 (s, 3 H) 2.25-2.36 (m, 2 H) 1.84 (dd, J=12.76, 2.22 Hz, 2 H) 1.50 (t, J=7.07 Hz, 3 H) 0.71-0.91 (m, 8 H).

Example 84

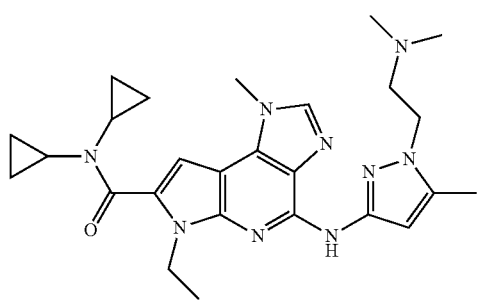 [SMILES: CCn1c(C(=O)N(C2CC2)C2CC2)cc2c3c(ncn3C)c(Nc3cc(C)n(CCN(C)C)n3)nc21]

N,N-dicyclopropyl-4-(1-(2-(dimethylamino)ethyl)-5-methyl-1H-pyrazol-3-ylamino)-6-ethyl-1-methyl-1,6-dihydroimidazo[4,5-d]pyrrolo[2,3-b]pyridine-7-carboxamide Prepared using similar procedure as for example 77.

MS (ESI) m/z 490 (M+H).

1H NMR (500 MHz, CHLOROFORM-d) δ ppm 8.08 (s, 1 H) 7.64 (s, 1 H) 6.96 (s, 1 H) 6.86 (s, 1 H) 4.65 (q, J=7.21 Hz, 2 H) 4.24 (br. s., 2 H) 4.01 (s, 3 H) 3.01-3.22 (m, 2 H) 2.70-2.89 (m, 2 H) 2.50 (br. s., 6 H) 2.37 (s, 3 H) 1.49 (t, J=7.07 Hz, 3 H) 0.71-0.91 (m, 8 H).

Example 85

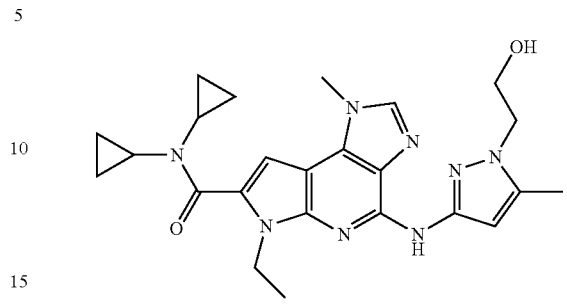

N,N-dicyclopropyl-6-ethyl-4-(1-(2-hydroxyethyl)-5-methyl-1H-pyrazol-3-ylamino)-1-methyl-1,6-dihydroimidazo[4,5-d]pyrrolo[2,3-b]pyridine-7-carboxamide Prepared using similar procedure as for example 77.

MS (ESI) m/z 463 (M+H).

1H NMR (500 MHz, MeOD) δ ppm 7.93 (s, 1 H) 7.16 (s, 1 H) 6.88 (s, 1 H) 4.60 (q, J=7.21 Hz, 2 H) 4.09 (t, J=5.55 Hz, 2 H) 4.05 (s, 3 H) 3.88 (t, J=5.55 Hz, 2 H) 2.88-3.00 (m, 2 H) 2.37 (s, 3 H) 1.43 (t, J=7.07 Hz, 3 H) 0.62-0.98 (m, 8 H).

Example 86

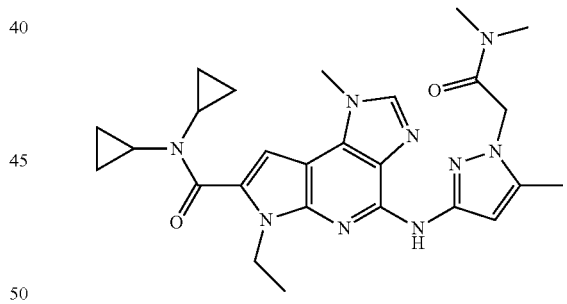

N,N-dicyclopropyl-4-(1-(2-(dimethylamino)-2-oxoethyl)-5-methyl-1H-pyrazol-3-ylamino)-6-ethyl-1-methyl-1,6-dihydroimidazo[4,5-d]pyrrolo[2,3-b]pyridine-7-carboxamide Prepared using similar procedure as for example 77.

MS (ESI) m/z 504 (M+H).

1H NMR (500 MHz, MeOD) δ ppm 7.93 (s, 1 H) 7.16 (s, 1 H) 6.99 (s, 1 H) 4.97 (s, 2 H) 4.61 (q, J=6.94 Hz, 2 H) 4.05 (s, 3 H) 3.15 (s, 3 H) 2.98 (s, 3 H) 2.79-2.97 (m, 2 H) 2.29 (s, 3 H) 1.44 (t, J=7.07 Hz, 3 H) 0.72-0.91 (m, 8 H).

Example 87

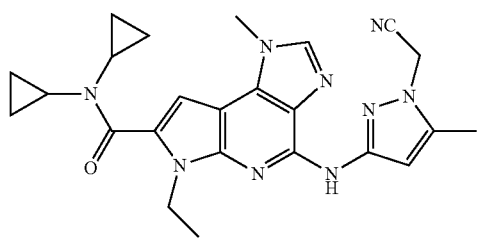 [SMILES: CCn1c(C(=O)N(C2CC2)C2CC2)cc2c3c(ncn3C)c(Nc3cc(C)n(CC#N)n3)nc21]

4-(1-(cyanomethyl)-5-methyl-1H-pyrazol-3-ylamino)-N,N-dicyclopropyl-6-ethyl-1-methyl-1,6-dihydroimidazo[4,5-d]pyrrolo[2,3-b]pyridine-7-carboxamide Prepared using similar procedure as for example 77.
MS (ESI) m/z 458 (M+H).
1H NMR (400 MHz, CHLOROFORM-d)™ ppm 8.17 (s, 1 H) 7.67 (s, 1 H) 7.10 (s, 1 H) 6.87 (s, 1 H) 4.93 (s, 2 H) 4.65 (q, J=7.04 Hz, 2 H) 4.01 (s, 3 H) 2.76-2.92 (m, 2 H) 2.43 (s, 3 H) 1.50 (t, J=7.04 Hz, 3 H) 0.68-0.93 (m, 8 H).

Example 88

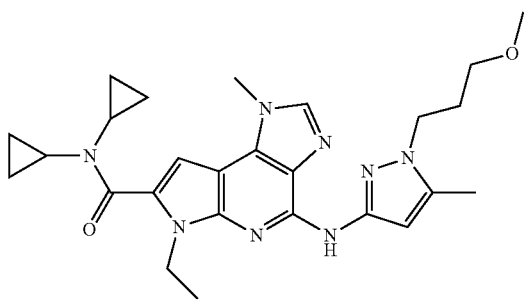 [SMILES: CCn1c(C(=O)N(C2CC2)C2CC2)cc2c3c(ncn3C)c(Nc3cc(C)n(CCCOC)n3)nc21]

N,N-dicyclopropyl-6-ethyl-4-(1-(3-methoxypropyl)-5-methyl-1H-pyrazol-3-ylamino)-1-methyl-1,6-dihydroimidazo[4,5-d]pyrrolo[2,3-b]pyridine-7-carboxamide Prepared using similar procedure as for example 77.
MS (ESI) m/z 491 (M+H).
1H NMR (400 MHz, CHLOROFORM-d)™ ppm 8.11 (s, 1 H) 7.62 (s, 1 H) 6.92 (s, 1 H) 6.78-6.89 (m, 1 H) 4.66 (q, J=7.04 Hz, 2 H) 4.06 (t, J=6.60 Hz, 2 H) 3.98 (s, 3 H) 3.29-3.39 (m, 4 H) 2.75-2.91 (m, 2 H) 2.34 (s, 3 H) 2.08 (dq, J=6.38, 6.16 Hz, 2 H) 1.50 (t, J=7.04 Hz, 3 H) 0.70-0.94 (m, 8 H).

Example 89

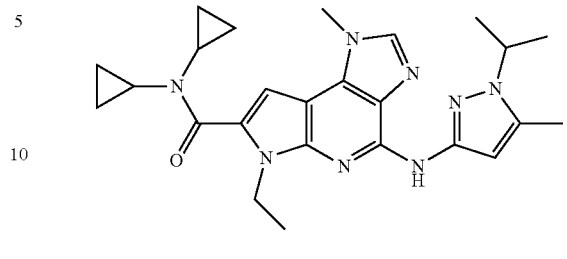

N,N-dicyclopropyl-6-ethyl-4-(1-isopropyl-5-methyl-1H-pyrazol-3-ylamino)-1-methyl-1,6-dihydroimidazo[4,5-d]pyrrolo[2,3-b]pyridine-7-carboxamide Prepared using similar procedure as for example 77.
MS (ESI) m/z 461 (M+H).
1H NMR (400 MHz, CHLOROFORM-d) δ ppm 8.15 (s, 1 H) 7.62 (s, 1 H) 6.91 (s, 1 H) 6.85 (s, 1 H) 4.66 (q, J=7.19 Hz, 2 H) 4.25-4.48 (m, 1 H) 3.99 (s, 3 H) 2.66-2.90 (m, J=7.13, 7.13, 3.85, 3.47 Hz, 2 H) 2.34 (s, 3 H) 1.38-1.58 (m, 9 H) 0.68-0.91 (m, 8 H).

Example 90

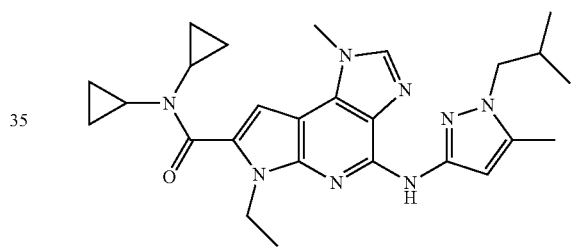

N,N-dicyclopropyl-6-ethyl-4-(1-isobutyl-5-methyl-1H-pyrazol-3-ylamino)-1-methyl-1,6-dihydroimidazo[4,5-d]pyrrolo[2,3-b]pyridine-7-carboxamide Prepared using similar procedure as for example 77.
MS (ESI) m/z 475 (M+H).
1H NMR (400 MHz, CHLOROFORM-d) δ ppm 8.11 (s, 1 H) 7.62 (s, 1 H) 6.93 (s, 1 H) 6.85 (s, 1 H) 4.66 (q, J=7.04 Hz, 2 H) 3.99 (s, 3 H) 3.74 (d, J=7.48 Hz, 2 H) 2.74-2.89 (m, 2 H) 2.33 (s, 3 H) 2.18-2.29 (m, 1 H) 1.50 (t, J=7.04 Hz, 3 H) 0.94 (d, J=6.60 Hz, 6 H) 0.72-0.88 (m, 8 H).

Example 91

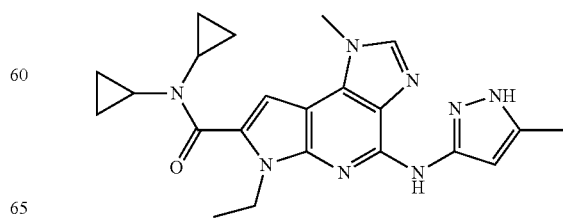

Preparation of N,N-dicyclopropyl-6-ethyl-1-methyl-4-(5-methyl-1H-pyrazol-3-ylamino)-1,6-dihydroimidazo[4,5-d]pyrrolo[2,3-b]pyridine-7-carboxamide Prepared using similar protocol as for example 72 from hydrazine.
MS (ESI) m/z 419.3 (M+H)
1H NMR (400 MHz, CHLOROFORM-d) δ ppm 8.70 (br s, 1 H), 7.91 (br s, 1 H), 6.87 (s, 1 H), 6.09 (br s, 1 H), 4.64 (q, 2 H, J=7.03 Hz), 4.08 (s, 3 H), 2.74-2.95 (m, 2 H), 2.41 (s, 3 H), 1.51 (t, 3 H, J=7.15 Hz), 0.81-0.95 (m, 4 H), 0.70-0.81 (m, 4 H)

Example 92

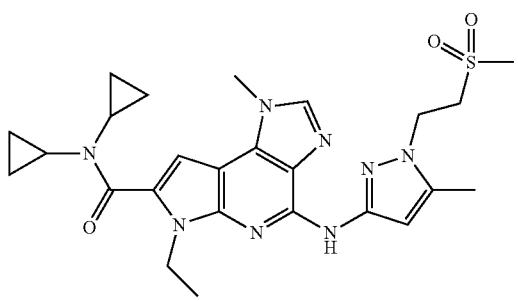 [SMILES: CCn1c(C(=O)N(C2CC2)C2CC2)cc2c3c(ncn3C)c(Nc3cc(C)n(CCS(C)(=O)=O)n3)nc21]

N,N-dicyclopropyl-6-ethyl-1-methyl-4-((5-methyl-1-(2-(methylsulfonyl)ethyl)-1H-pyrazol-3-yl)amino)-1,6-dihydroimidazo[4,5-d]pyrrolo[2,3-b]pyridine-7-carboxamide Prepared using the same procedure as used for example 77.
MS (ESI) m/z 525.3 (M+H)
1H NMR (CDCl₃) δ ppm 8.25 (br s, 1H), 7.75 (s, 1H), 6.86 (s, 1H), 6.77 (s, 1H), 4.54 (q, 2H, J=8 Hz), 4.36 (t, 2H, J=8 Hz), 3.97 (s, 3H), 3.58 (t, 2H, J=8 Hz), 2.71-2.77 (m, 2H), 2.44 (s, 3H), 2.34 (s, 3H), 1.41 (t, 3H, J=8 Hz), 0.75-0.78 (m, 4H), 0.67-0.71 (m, 4H).

Example 93

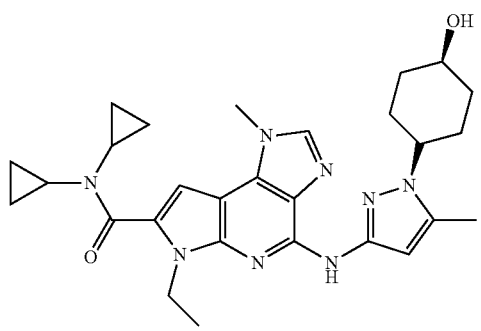

N,N-dicyclopropyl-6-ethyl-4-((1-(cis-4-hydroxycyclohexyl)-5-methyl-1H-pyrazol-3-yl)amino)-1-methyl-1,6-dihydroimidazo[4,5-d]pyrrolo[2,3-b]pyridine-7-carboxamide Prepared using the same procedure as used for example 77.
MS (ESI) m/z 517.4 (M+H)
1H NMR (CDCl₃) δ ppm 8.14 (br s, 1H), 7.56 (s, 1H), 6.83 (s, 1H), 6.76 (s, 1H), 4.59 (q, 2H, J=8 Hz), 4.01-4.02 (m, 1H), 3.93 (s, 3H), 3.88-3.93 (m, 1H), 2.73-2.77 (m, 2H), 2.28 (s, 3H), 2.25-2.33 (m, 2H), 1.93-1.96 (m, 2H), 1.59-1.73 (m, 4H), 1.42 (t, 3H, J=8 Hz), 0.73-0.78 (m, 4H), 0.66-0.70 (m, 4H).

Example 94

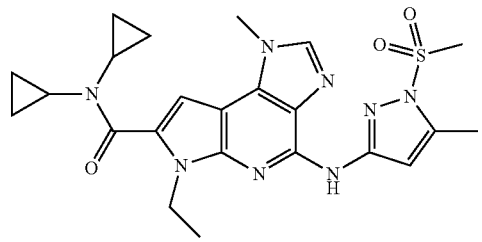 [SMILES: CCn1c(C(=O)N(C2CC2)C2CC2)cc2c3c(ncn3C)c(Nc3cc(C)n(S(C)(=O)=O)n3)nc21]

N,N-dicyclopropyl-6-ethyl-1-methyl-4-((5-methyl-1-(methylsulfonyl)-1H-pyrazol-3-yl)amino)-1,6-dihydroimidazo[4,5-d]pyrrolo[2,3-b]pyridine-7-carboxamide Prepared using the same procedure as used for example 77.
MS (ESI) m/z 497.3 (M+H)
1H NMR (CDCl₃) δ ppm 8.46 (br s, 1H), 7.75 (s, 1H), 7.16 (s, 1H), 6.78 (s, 1H), 4.54 (q, 2H, J=8 Hz), 3.97 (s, 3H), 3.19 (s, 3H), 2.72-2.76 (m, 2H), 2.51 (s, 3H), 1.41 (t, 3H, J=8 Hz), 0.72-0.78 (m, 4H), 0.66-0.69 (m, 4H).

Example 95

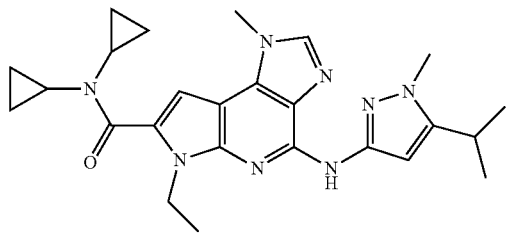 [SMILES: CCn1c(C(=O)N(C2CC2)C2CC2)cc2c3c(ncn3C)c(Nc3cc(C(C)C)n(C)n3)nc21]

N,N-dicyclopropyl-6-ethyl-4-(5-isopropyl-1-methyl-1H-pyrazol-3-ylamino)-1-methyl-1,6-dihydroimidazo[4,5-d]pyrrolo[2,3-b]pyridine-7-carboxamide 95A Preparation of 4-methyl-1,1-bis(methylthio)pent-1-en-3-one

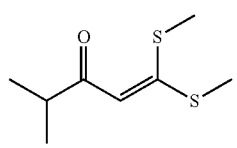

The title compound was prepared using a method analogous to that used to prepare Example 70A.
1H NMR (400 MHz, CDCl₃) δ: 6.08 (s, 1H), 2.47 (s, 3H), 2.46 (s, 3H), 1.14 (s, 3H), 1.12 (s, 3H).

95B Preparation of (Z)—N,N-dicyclopropyl-6-ethyl-1-methyl-4-(4-methyl-1-(methylthio)-3-oxopent-1-enylamino)-1,6-dihydroimidazo[4,5-d]pyrrolo[2,3-b]pyridine-7-carboxamide

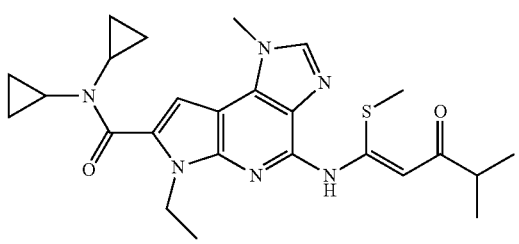 [SMILES: CCn1c(C(=O)N(C2CC2)C2CC2)cc2c3c(ncn3C)c(N/C(=C/C(=O)C(C)C)SC)nc21]

The title compound was prepared using a method analogous to that used to prepare example 70B.
MS (ESI) m/z 481.4 (M+H).

95 Preparation of N,N-dicyclopropyl-6-ethyl-4-(5-isopropyl-1-methyl-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 73.
MS (ESI) m/z 461.4 (M+H).
$^1$H NMR (500 MHz, CDCl$_3$) δ: 7.80 (s, 1H), 7.07 (s, 1H), 6.86 (s, 1H), 4.60 (q, J=6.9 Hz, 2H), 4.02 (s, 3H), 3.79 (s, 3H), 2.93-3.01 (m, 1H), 2.79-2.86 (m, 2H), 1.52 (t, J=7.1 Hz, 3H), 1.35 (d, J=6.9 Hz, 6H), 0.82-0.89 (m, 4H), 0.72-0.78 (m, 4H).

Example 96

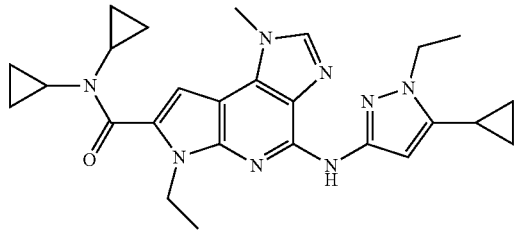 [SMILES: CCn1nc(Nc2nc3c(cc(C(=O)N(C4CC4)C4CC4)n3CC)c3c2ncn3C)cc1C1CC1]

N,N-dicyclopropyl-4-(5-cyclopropyl-1-ethyl-1H-pyrazol-3-ylamino)-6-ethyl-1-methyl-1,6-dihydroimidazo[4,5-d]pyrrolo[2,3-b]pyridine-7-carboxamide 96A Preparation of 1-cyclopropyl-3,3-bis(methylthio)prop-2-en-1-one

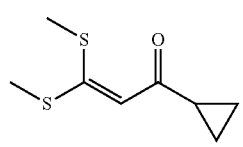

The title compound was prepared using a method analogous to that used to prepare example 72A.
$^1$H NMR (400 MHz, CDCl$_3$) δ: 6.23 (s, 1H), 2.50 (s, 3H), 2.48 (s, 3H), 1.86-1.94 (m, 1H), 1.09 (quin, J=3.7 Hz, 2H), 0.82-0.88 (m, 2H).

96B Preparation of (Z)—N,N-dicyclopropyl-4-(3-cyclopropyl-1-(methylthio)-3-oxoprop-1-enylamino)-6-ethyl-1-methyl-1,6-dihydroimidazo[4,5-d]pyrrolo[2,3-b]pyridine-7-carboxamide

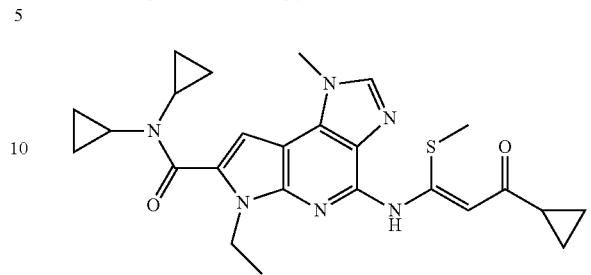

The title compound was prepared using a method analogous to that used to prepare example 72B.
MS (ESI) m/z 479.3 (M+H).
$^1$H NMR (400 MHz, CDCl$_3$) δ: 14.81 (s, 1H), 7.75 (s, 1H), 6.85 (s, 1H), 5.58 (s, 1H), 4.62 (q, J=7.0 Hz, 2H), 4.00 (s, 3H), 2.75-2.85 (m, 2H), 2.45 (s, 3H), 1.76-1.86 (m, 1H), 1.46 (t, J=7.0 Hz, 3H), 1.17-1.28 (m, 2H), 0.69-0.91 (m, 10H).

96 Preparation of N,N-dicyclopropyl-4-(5-cyclopropyl-1-ethyl-1H-pyrazol-3-ylamino)-6-ethyl-1-methyl-1,6-dihydroimidazo[4,5-d]pyrrolo[2,3-b]pyridine-7-carboxamide The title compound was prepared using a method analogous to that used to prepare example 73.
MS (ESI) m/z 473.3 (M+H).

Example 97

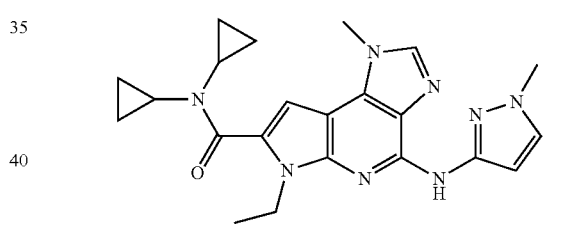

N,N-dicyclopropyl-6-ethyl-1-methyl-4-(1-methyl-1H-pyrazol-3-ylamino)-1,6-dihydroimidazo[4,5-d]pyrrolo[2,3-b]pyridine-7-carboxamide 97A Preparation of 4-bromo-N,N-dicyclopropyl-6-ethyl-1-methyl-1,6-dihydroimidazo[4,5-d]pyrrolo[2,3-b]pyridine-7-carboxamide

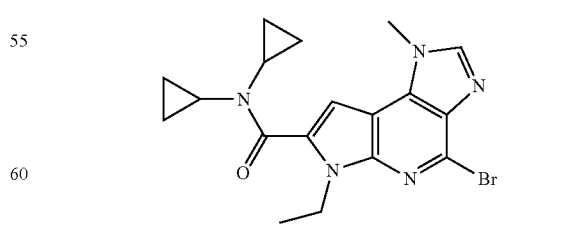

A round bottom flask charged with 4-amino-N,N-dicyclopropyl-6-ethyl-1-methyl-1,6-dihydroimidazo[4,5-d]pyrrolo[2,3-b]pyridine-7-carboxamide (134.4 mg, 0.397 mmol) under an atmosphere of nitrogen was treated with dibromomethane (397 μL). Isoamyl nitrate (107 μL, 0.794 mmol) was added and the reaction mixture was heated at 60° C. 3.5 h and cooled to rt. The reaction mixture was diluted with ethyl acetate and washed with saturated aqueous sodium bicarbonate. The organics were dried over anhydrous sodium sulfate, filtered and concentrated in vacuo. 4-Bromo-N,N-dicyclopropyl-6-ethyl-1-methyl-1,6-dihydroimidazo[4,5-d]pyrrolo[2,3-b]pyridine-7-carboxamide (0.156 g, 0.388 mmol, 98% yield) was isolated as a brown glassy solid. The product was used immediately in the next reaction.

MS (ESI) m/z 404.2 (M+H)

97 Preparation of N,N-dicyclopropyl-6-ethyl-1-methyl-4-(1-methyl-1H-pyrazol-3-ylamino)-1,6-dihydroimidazo[4,5-d]pyrrolo[2,3-b]pyridine-7-carboxamide To a vial containing 1-methyl-1H-pyrazol-3-amine (11.89 mg, 0.122 mmol), Pd$_2$(dba)$_3$ (4.67 mg, 5.10 mmol), Xantphos (5.90 mg, 10.20 mmol), and cesium carbonate (100 mg, 0.306 mmol) was added 4-bromo-N,N-dicyclopropyl-6-ethyl-1-methyl-1,6-dihydroimidazo[4,5-d]pyrrolo[2,3-b]pyridine-7-carboxamide (example 97A, 41.0 mg, 0.102 mmol) in DME (1020 μL). The reaction mixture was sparged with argon for 5 min, the vial was capped, and the reaction mixture was heated at 60° C. for 4 h and 80° C. for 16 h. The reaction mixture was concentrated in vacuo. The crude residue was purified by flash column chromatography using an Isco 40 g column eluting with 0-5% MeOH/CH$_2$Cl$_2$ followed by additional purification with preparative HPLC. N,N-Dicyclopropyl-6-ethyl-1-methyl-4-(1-methyl-1H-pyrazol-3-ylamino)-1,6-dihydroimidazo[4,5-d]pyrrolo[2,3-b]pyridine-7-carboxamide (13 mg, 0.030 mmol, 29.5% yield) was isolated as a white solid.

MS (ESI) m/z 419.3 (M+H)
1H NMR (400 MHz, CHLOROFORM-d) δ ppm 8.17 (s, 1 H), 7.64 (s, 1 H), 7.31 (d, 1H, J=2.26 Hz), 7.16 (d, 1 H, J=2.26 Hz), 6.86 (s, 1 H), 4.65 (q, 2 H, J=7.03 Hz), 4.01 (s, 3 H), 3.85 (s, 3H), 2.78-2.87 (m, 2 H), 1.49 (t, 3 H, J=7.15 Hz), 0.81-0.89 (m, 4 H), 0.71-0.80 (m, 4 H)

Example 98

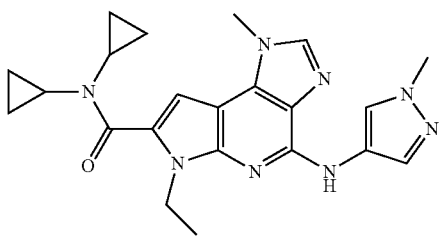 [SMILES: CCn1c(C(=O)N(C2CC2)C2CC2)cc2c3c(ncn3C)c(Nc3cnn(C)c3)nc21]

N,N-dicyclopropyl-6-ethyl-1-methyl-4-(1-methyl-1H-pyrazol-4-ylamino)-1,6-dihydroimidazo[4,5-d]pyrrolo[2,3-b]pyridine-7-carboxamide Prepared using similar procedure as used for example 97.
$^1$H NMR (500 MHz, CHLOROFORM-d) δ: 8.15 (s, 1H), 7.72 (s, 1H), 7.67 (s, 1H), 7.66 (br. s., 1H), 6.85 (s, 1H), 4.65 (q, J=7.2 Hz, 2H), 4.01 (s, 3H), 3.95 (s, 3H), 2.79-2.86 (m, 2H), 1.50 (t, J=7.1 Hz, 3H), 0.81-0.89 (m, 4H), 0.73-0.79 (m, 4H).

Example 99

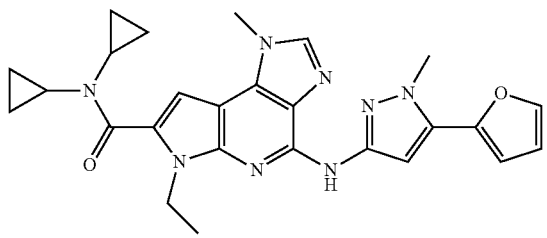 [SMILES: CCn1c(C(=O)N(C2CC2)C2CC2)cc2c3c(ncn3C)c(Nc3cc(-c4ccco4)n(C)n3)nc21]

N,N-dicyclopropyl-6-ethyl-4-((5-(2-furyl)-1-methyl-1H-pyrazol-3-yl)amino)-1-methyl-1,6-dihydroimidazo[4,5-d]pyrrolo[2,3-b]pyridine-7-carboxamide Prepared in a similar method used for example 73.
MS (ESI) m/z 485.4 (M+H)
1H NMR (CDCl$_3$) δ ppm 8.03 (br s, 1H), 7.58 (s, 1H), 7.48 (m, 1H), 7.35 (s, 1H), 6.79 (s, 1 H), 6.54 (d, 1H, J=3.3 Hz), 6.47 (m, 1H), 4.58 (q, 2 H, J=7.04 Hz), 3.94 (s, 3H), 3.93 (s, 3H), 2.74 (m, 2H), 1.44 (t, 3H), 0.69-0.79 (m, 8H)

Example 100

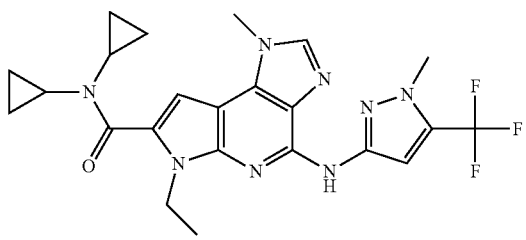 [SMILES: CCn1c(C(=O)N(C2CC2)C2CC2)cc2c3c(ncn3C)c(Nc3cc(C(F)(F)F)n(C)n3)nc21]

N,N-dicyclopropyl-6-ethyl-1-methyl-4-((1-methyl-5-(trifluoromethyl)-1H-pyrazol-3-yl)amino)-1,6-dihydroimidazo[4,5-d]pyrrolo[2,3-b]pyridine-7-carboxamide Prepared in a similar method used for example 73.
MS (ESI) m/z 487.3 (M+H)
1H NMR (CDCl$_3$) δ ppm 7.41 (s, 1 H), 7.12 (s, 1H), 6.78 (s, 1 H), 4.52 (q, 2H, J=7.04 Hz), 4.11 (s, 3H), 3.86 (s, 3H), 2.74 (m, 2H), 1.42 (t, 3H, J=7.15 Hz), 0.67-0.80 (m, 8H)

Example 101

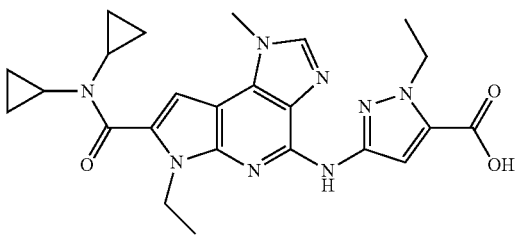 [SMILES: CCn1nc(Nc2nc3c(cc(C(=O)N(C4CC4)C4CC4)n3CC)c3c2ncn3C)cc1C(=O)O]

3-(7-(dicyclopropylcarbamoyl)-6-ethyl-1-methyl-1,
6-dihydroimidazo[4,5-d]pyrrolo[2,3-b]pyridin-4-
ylamino)-1-ethyl-1H-pyrazole-5-carboxylic acid 101A Preparation of (Z)—N,N-dicyclopropyl-4-(4,4-
dimethoxy-1-(methylthio)-3-oxobut-1-enylamino)-6-
ethyl-1-methyl-1,6-dihydroimidazo[4,5-d]pyrrolo[2,
3-b]pyridine-7-carboxamide

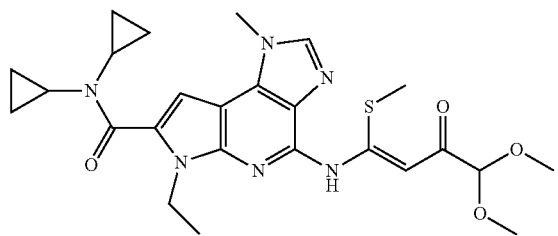 [SMILES: CCn1c(C(=O)N(C2CC2)C2CC2)cc2c3c(ncn3C)c(N/C(=C/C(=O)C(OC)OC)SC)nc21]

Sodium hydride (142 mg, 3.55 mmol) was added to 4-amino-N,N-dicyclopropyl-6-ethyl-1-methyl-1,6-dihydroimidazo[4,5-d]pyrrolo[2,3-b]pyridine-7-carboxamide (example 1J, 400 mg, 1.182 mmol) in DMF (7 mL) at room temperature and the mixture stirred for 30 min, 1,1-dimethoxy-4,4-bis(methylthio)but-3-en-2-one (394 mg, 1.773 mmol) was added and stirring continued overnight. The reaction mixture was diluted with ethyl acetate and washed with water, 10% lithium chloride and water. The organic layer was dried over magnesium sulfate, filtered and concentrated in vacuo. The crude product was purified by flash chromatography on silica gel using an automated ISCO system (80 g column, eluting with 2-5% methanol/dichloromethane). (Z)—N,N-Dicyclopropyl-4-(4,4-dimethoxy-1-(methylthio)-3-oxobut-1-enylamino)-6-ethyl-1-methyl-1,6-dihydroimidazo[4,5-d]pyrrolo[2,3-b]pyridine-7-carboxamide (484 mg, 0.944 mmol, 80% yield) was obtained as a yellow solid.

101B Preparation of (Z)-tert-butyl 2-(1-(7-(dicyclopropylcarbamoyl)-6-ethyl-1-methyl-1,6-dihydroimidazo[4,5-d]pyrrolo[2,3-b]pyridin-4-ylamino)-4,4-dimethoxy-3-oxobut-1-enyl)-1-ethylhydrazinecarboxylate

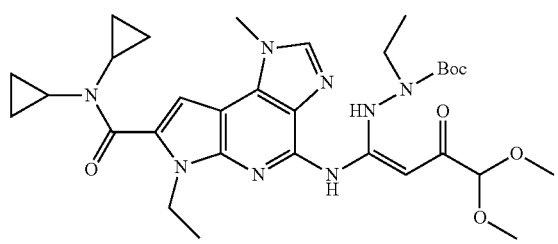 [SMILES: CCN(N/C(=C\C(=O)C(OC)OC)Nc1nc2c(cc(C(=O)N(C3CC3)C3CC3)n2CC)c2c1ncn2C)C(=O)OC(C)(C)C]

A mixture of (Z)—N,N-dicyclopropyl-4-(4,4-dimethoxy-1-(methylthio)-3-oxobut-1-enylamino)-6-ethyl-1-methyl-1,6-dihydroimidazo[4,5-d]pyrrolo[2,3-b]pyridine-7-carboxamide (example 101A, 160 mg, 0.312 mmol) and tert-butyl 1-ethylhydrazinecarboxylate (125 mg, 0.780 mmol) in acetic acid (2 mL) wan stirred at 35° C. overnight. Solvent was evaporated and the crude product was purified by flash chromatography on silica gel using an automated ISCO system (40 g column, eluting with 2-8% methanol/dichloromethane). (Z)-tert-Butyl 2-(1-(7-(dicyclopropylcarbamoyl)-6-ethyl-1-methyl-1,6-dihydroimidazo[4,5-d]pyrrolo[2,3-b]pyridin-4-ylamino)-4,4-dimethoxy-3-oxobut-1-enyl)-1-ethylhydrazinecarboxylate (195 mg, 0.312 mmol, 100% yield) was obtained as a yellow solid.

MS (ESI) m/z 625.5 (M+H).

101C Preparation of N,N-dicyclopropyl-6-ethyl-4-
(1-ethyl-5-formyl-1H-pyrazol-3-ylamino)-1-methyl-
1,6-dihydroimidazo[4,5-d]pyrrolo[2,3-b]pyridine-7-
carboxamide

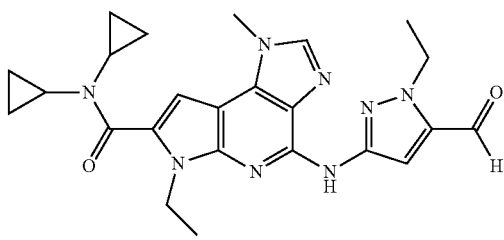 [SMILES: CCn1nc(Nc2nc3c(cc(C(=O)N(C4CC4)C4CC4)n3CC)c3c2ncn3C)cc1C=O]

A mixture of (Z)-tert-butyl 2-(1-(7-(dicyclopropylcarbamoyl)-6-ethyl-1-methyl-1,6-dihydroimidazo[4,5-d]pyrrolo[2,3-b]pyridin-4-ylamino)-4,4-dimethoxy-3-oxobut-1-enyl)-1-ethylhydrazinecarboxylate (187 mg, 0.299 mmol) and TFA (25% in dichloroethane, 1.0 mL, 2.99 mmol) was heated at 60° C. for 0.5 h and LC/MS showed completion of reaction. Solvent was evaporated and the residue was partitioned between saturated sodium bicarbonate and dichloromethane. The layers were separated and aqueous layer was extracted with dichloromethane two more times. The combined organic layer was dried over magnesium sulfate, filtered and concentrated in vacuo. The crude product was purified by flash chromatography on silica gel using an automated ISCO system (24 g column, eluting with 1-5% methanol/dichloromethane). N,N-dicyclopropyl-6-ethyl-4-(1-ethyl-5-formyl-1H-pyrazol-3-ylamino)-1-methyl-1,6-dihydroimidazo[4,5-d]pyrrolo[2,3-b]pyridine-7-carboxamide (80 mg, 0.174 mmol, 58.0% yield) was obtained as a yellow solid.

MS (ESI) m/z 461.4 (M+H).

$^1$H NMR (500 MHz, CDCl$_3$) δ: 9.88 (s, 1H), 8.25 (s, 1H), 7.76 (s, 1H), 7.67 (s, 1H), 6.87 (s, 1H), 4.67 (d, J=7.2 Hz, 2H), 4.52 (q, J=7.1 Hz, 2H), 4.02 (s, 3H), 2.80-2.86 (m, 2H), 1.52 (t, J=7.1 Hz, 3H), 1.44 (t, J=7.2 Hz, 3H), 0.83-0.89 (m, 4H), 0.73-0.79 (m, 4H)

101 Preparation of 3-(7-(dicyclopropylcarbamoyl)-6-
ethyl-1-methyl-1,6-dihydroimidazo[4,5-d]pyrrolo[2,
3-b]pyridin-4-ylamino)-1-ethyl-1H-pyrazole-5-car-
boxylic acid A mixture of N,N-dicyclopropyl-6-ethyl-4-(1-ethyl-5-formyl-1H-pyrazol-3-ylamino)-1-methyl-1,6-dihydroimidazo[4,5-d]pyrrolo[2,3-b]pyridine-7-carboxamide (example 101C, 27 mg, 0.059 mmol) and OXONE (79 mg, 0.129 mmol) in DMF was stirred at room temperature for 20 hrs. Water was added and the mixture was extracted with dichloromethane 3 times. The organic layer was dried over magnesium sulfate, filtered and concentrated in vacuo. The crude product was purified with preparative HPLC to give 3-(7-(dicyclopropylcarbamoyl)-6-ethyl-1-methyl-1,6-dihydroimidazo[4,5-d]pyrrolo[2,3-b]pyridin-4-ylamino)-1-ethyl-1H-pyrazole-5-carboxylic acid (20 mg, 98% yield)

MS (ESI) m/z 477.4 (M+H).

$^1$H NMR (500 MHz, METHANOL-d$_4$) δ: 7.96 (s, 1H), 7.48 (s, 1H), 7.18 (s, 1H), 4.70 (q, J=6.9 Hz, 2H), 4.60 (q, J=7.2 Hz, 2H), 4.09 (s, 3H), 2.94-3.00 (m, 2H), 1.45 (t, J=6.94 Hz, 3H), 1.44 (t, J=7.21 Hz, 3H), 0.85-0.92 (m, 4H), 0.77-0.82 (m, 4H)

Example 102

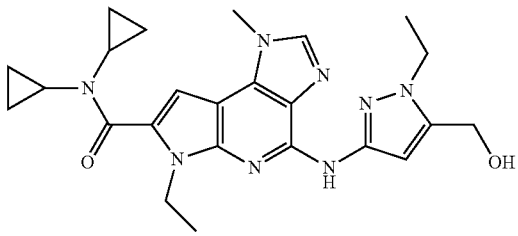 [SMILES: CCn1nc(Nc2nc3c(cc(C(=O)N(C4CC4)C4CC4)n3CC)c3c2ncn3C)cc1CO]

N,N-dicyclopropyl-6-ethyl-4-(1-ethyl-5-(hydroxymethyl)-1H-pyrazol-3-ylamino)-1-methyl-1,6-dihydroimidazo[4,5-d]pyrrolo[2,3-b]pyridine-7-carboxamide Sodium boronhydride (10 wt % on alumina, 13.14 mg, 0.035 mmol) was added to N,N-dicyclopropyl-6-ethyl-4-(1-ethyl-5-formyl-1H-pyrazol-3-ylamino)-1-methyl-1,6-dihydroimidazo[4,5-d]pyrrolo[2,3-b]pyridine-7-carboxamide (example 101C, 16 mg, 0.035 mmol) in methanol (1 mL) at room temperature and the reaction mixture stirred for 0.5 h. The solid alumina was filtered off and the filtrate was concentrated in vacuo. The crude product was purified by flash chromatography on silica gel using an automated ISCO system (4 g column, eluting with 2-10% methanol/dichloromethane). N,N-dicyclopropyl-6-ethyl-4-(1-ethyl-5-(hydroxymethyl)-1H-pyrazol-3-ylamino)-1-methyl-1,6-dihydroimidazo[4,5-d]pyrrolo[2,3-b]pyridine-7-carboxamide (14 mg, 86% yield) was obtained as a white solid.

MS (ESI) m/z 563.4 (M+H).

$^1$H NMR (500 MHz, CDCl$_3$) δ: 8.09 (s, 1H), 7.59 (s, 1H), 7.08 (s, 1H), 6.81 (s, 1H), 4.72 (d, J=4.7 Hz, 2H), 4.57 (q, J=7.2 Hz, 2H), 4.15 (q, J=7.3 Hz, 2H), 3.97 (s, 3H), 2.76-2.84 (m, 3H), 1.46 (t, J=7.2 Hz, 3H), 1.41 (t, J=7.1 Hz, 3H), 0.81-0.87 (m, 4H), 0.71-0.76 (m, 4H)

Example 103

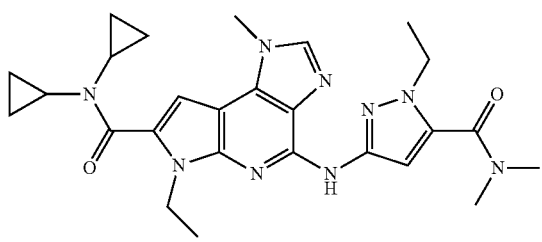 [SMILES: CCn1nc(Nc2nc3c(cc(C(=O)N(C4CC4)C4CC4)n3CC)c3c2ncn3C)cc1C(=O)N(C)C]

N,N-dicyclopropyl-4-(5-(dimethylcarbamoyl)-1-ethyl-1H-pyrazol-3-ylamino)-6-ethyl-1-methyl-1,6-dihydroimidazo[4,5-d]pyrrolo[2,3-b]pyridine-7-carboxamide A mixture of 3-(7-(dicyclopropylcarbamoyl)-6-ethyl-1-methyl-1,6-dihydroimidazo[4,5-d]pyrrolo[2,3-b]pyridin-4-ylamino)-1-ethyl-1H-pyrazole-5-carboxylic acid (example 101, 28 mg, 0.059 mmol), HATU (26.8 mg, 0.071 mmol) and dimethylamine (2M in THF, 59 μL, 0.118 mmol) in DMF (1 mL) was stirred at room temperature for 2 h. Water was added and the reaction mixture was extracted with ethyl acetate 3 times. The combined organic layers were washed twice with 10% lithium chloride, dried over magnesium sulfate, filtered and concentrated in vacuo. The crude was purified by preparative HPLC (Phenomenex Luna 5u C18 column, 21.2× 250 mm column, retention time 15.317 min, 30-100% gradient aqueous methanol over 20 minutes containing 10 mM ammonium acetate, flow rate 20 ml/min and monitoring at 254 nm). N,N-dicyclopropyl-4-(5-(dimethylcarbamoyl)-1-ethyl-1H-pyrazol-3-ylamino)-6-ethyl-1-methyl-1,6-dihydroimidazo[4,5-d]pyrrolo[2,3-b]pyridine-7-carboxamide (20 mg, 66.9% yield) was obtained as an off-white solid.

MS (ESI) m/z 504.5 (M+H).

$^1$H NMR (500 MHz, CDCl$_3$) δ: 8.38 (br. S, 1H), 7.75 (s, 1H), 7.28 (s, 1H), 6.86 (s, 1H), 4.61 (q, J=7.2 Hz, 2H), 4.27 (q, J=7.0 Hz, 5H), 4.03 (s, 3H), 3.27 (s, 3H), 3.17 (s, 3H), 2.79-2.86 (m, 2H), 1.47 (t, J=7.14 Hz, 3H), 1.46 (t, J=7.14 Hz, 3H), 0.83-0.89 (m, 4H), 0.73-0.78 (m, 4H)

Example 104

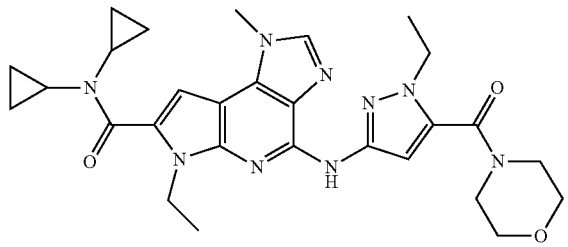 [SMILES: CCn1nc(Nc2nc3c(cc(C(=O)N(C4CC4)C4CC4)n3CC)c3c2ncn3C)cc1C(=O)N1CCOCC1]

N,N-dicyclopropyl-6-ethyl-4-(1-ethyl-5-(morpholine-4-carbonyl)-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 103.

MS (ESI) m/z 546.5 (M+H).

$^1$H NMR (500 MHz, CDCl$_3$) δ: 7.95 (s, 1H), 7.19 (s, 1H), 6.87 (s, 1H), 4.60 (q, J=6.9 Hz, 2H), 4.28 (q, J=7.2 Hz, 5H), 4.07 (s, 3H), 3.82 (br. s., 5H), 3.76 (br. s., 3H), 2.74-2.93 (m, 4H), 1.48 (t, J=7.14 Hz, 3H), 1.47 (t, J=7.14 Hz, 3H), 0.84-0.90 (m, 4H), 0.74-0.78 (m, 4H).

Example 105

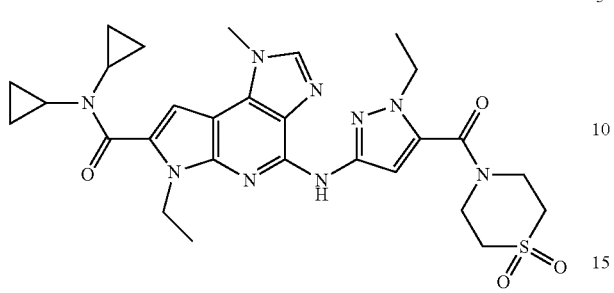

N,N-dicyclopropyl-6-ethyl-4-(1-ethyl-5-(thiomorpholine 1,1-dioxide-4-carbonyl)-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 103.

MS (ESI) m/z 594.5 (M+H).

$^1$H NMR (500 MHz, CDCl$_3$) δ: 7.95 (s, 1H), 7.19 (s, 1H), 6.83 (s, 1H), 4.55 (q, J=7.03 Hz, 2H), 4.20-4.34 (m, 6H), 4.06 (s, 3H), 3.13 (br. s., 4H), 2.77-2.89 (m, 2H), 1.46 (t, J=7.21 Hz, 3H), 1.43 (t, J=7.21 Hz, 3H), 0.82-0.88 (m, 4H), 0.72-0.77 (m, 4H).

Example 106

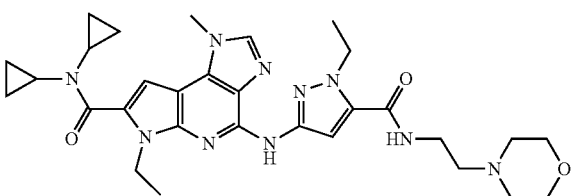

N,N-dicyclopropyl-6-ethyl-4-(1-ethyl-5-(2-morpholinoethylcarbamoyl)-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 103.

MS (ESI) m/z 589.6 (M+H).

$^1$H NMR (500 MHz, CDCl$_3$) δ: 8.18 (s, 1H), 7.68 (s, 1H), 7.45 (s, 1H), 6.87 (s, 1H), 4.64 (q, J=6.9 Hz, 2H), 4.54 (q, J=7.2 Hz, 2H), 4.03 (s, 3H), 3.77 (br. s., 4H), 3.61 (br. s., 2H), 2.80-2.87 (m, 2H), 2.67 (br. s., 2H), 2.57 (br. s., 3H), 1.71 (br. s., 3H), 1.53 (t, J=7.1 Hz, 3H), 1.46 (t, J=7.1 Hz, 3H), 0.84-0.90 (m, 4H), 0.74-0.79 (m, 4H).

Example 107

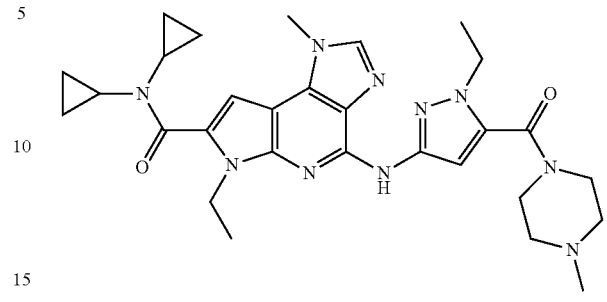

N,N-dicyclopropyl-6-ethyl-4-(1-ethyl-5-(4-methylpiperazine-1-carbonyl)-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 103.

MS (ESI) m/z 559.5 (M+H).

$^1$H NMR (500 MHz, CDCl$_3$) δ: 8.19 (s, 1H), 7.66 (s, 1H), 7.26 (s, 1H), 6.87 (s, 1H), 4.63 (q, J=6.9 Hz, 2H), 4.26 (q, J=7.2 Hz, 2H), 4.02 (s, 3H), 3.88 (br. s., 4H), 2.80-2.86 (m, 2H), 2.54 (br. s., 4H), 2.40 (br. s., 3H), 1.48 (t, J=7.1 Hz, 3H), 1.47 (t, J=7.1 Hz, 3H), 0.82-0.90 (m, 4H), 0.73-0.79 (m, 4H).

Example 108

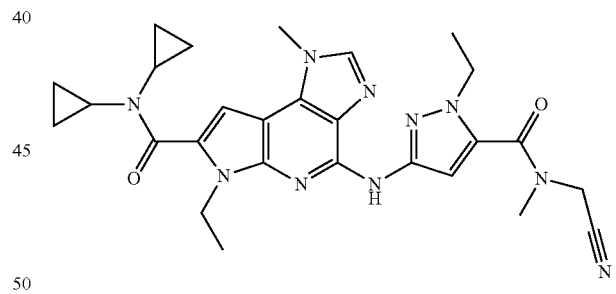

4-(5-((cyanomethyl)(methyl)carbamoyl)-1-ethyl-1H-pyrazol-3-ylamino)-N,N-dicyclopropyl-6-ethyl-1-methyl-1,6-dihydroimidazo[4,5-d]pyrrolo[2,3-b]pyridine-7-carboxamide The title compound was prepared using a method analogous to that used to prepare example 103.

MS (ESI) m/z 529.3 (M+H).

$^1$H NMR (500 MHz, CDCl$_3$) δ: 8.37 (br. s., 1H), 7.77 (s, 1H), 7.39 (s, 1H), 6.86 (s, 1H), 4.62 (q, J=7.2 Hz, 2H), 4.54 (br. s., 2H), 4.27-4.34 (m, 1H), 4.04 (s, 3H), 3.41 (br. s., 3H), 2.79-2.86 (m, 2H), 1.47 (t, J=7.2 Hz, 6H), 0.83-0.89 (m, 4H), 0.73-0.78 (m, 4H).

Example 109

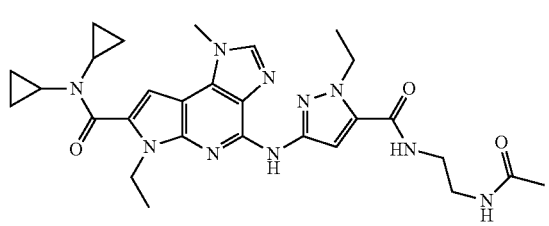 [SMILES: CCn1nc(Nc2nc3c(cc(C(=O)N(C4CC4)C4CC4)n3CC)c3c2ncn3C)cc1C(=O)NCCNC(C)=O]

4-((5-((2-acetamidoethyl)carbamoyl)-1-ethyl-1H-pyrazol-3-yl)amino)-N,N-dicyclopropyl-6-ethyl-1-methyl-1,6-dihydroimidazo[4,5-d]pyrrolo[2,3-b]pyridine-7-carboxamide The title compound was prepared using a method analogous to that used to prepare example 103.

MS (ESI) m/z 561.5 (M+H).

$^1$H NMR (500 MHz, CDCl$_3$) δ: 7.77 (br. s., 2H), 7.40 (s, 1H), 6.72 (s, 1H), 4.48-4.56 (m, 4H), 3.99 (s, 3H), 3.61-3.66 (m, 2H), 3.52-3.58 (m, 2H), 2.81 (m, 2H), 2.02 (s, 3H), 1.44 (t, J=7.1 Hz, 3H), 1.34 (t, J=6.9 Hz, 3H), 1.26 (s, 1H), 0.82-0.90 (m, 4H), 0.70-0.77 (m, 4H)

Example 110

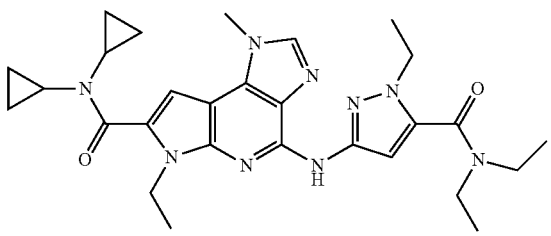 [SMILES: CCN(CC)C(=O)c1cc(Nc2nc3c(cc(C(=O)N(C4CC4)C4CC4)n3CC)c3c2ncn3C)nn1CC]

N,N-dicyclopropyl-4-((5-(diethylcarbamoyl)-1-ethyl-1H-pyrazol-3-yl)amino)-6-ethyl-1-methyl-1,6-dihydroimidazo[4,5-d]pyrrolo[2,3-b]pyridine-7-carboxamide The title compound was prepared using a method analogous to that used to prepare example 103.

MS (ESI) m/z 532.4 (M+H).

$^1$H NMR (500 MHz, CDCl$_3$) δ: 8.29 (br. S., 1H), 7.70 (s, 1H), 7.23 (s, 1H), 6.85 (s, 1H), 4.62 (q, J=6.9 Hz, 2H), 4.20 (q, J=7.2 Hz, 2H), 4.00 (s, 3H), 3.51-3.62 (m, 4H), 2.77-2.85 (m, 2H), 1.40-1.47 (m, 6H), 1.27 (t, J=7.1 Hz, 6H), 0.80-0.88 (m, 4H), 0.72-0.77 (m, 4H)

Example 111

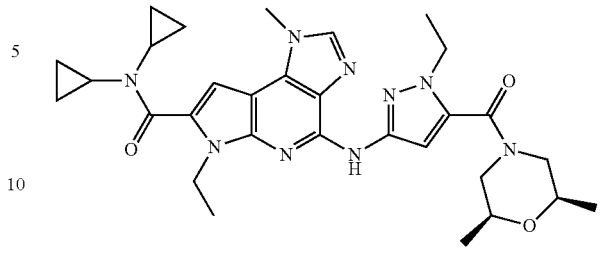

N,N-dicyclopropyl-4-((5-(((2R,6S)-2,6-dimethyl-4-morpholinyl)carbonyl)-1-ethyl-1H-pyrazol-3-yl)amino)-6-ethyl-1-methyl-1,6-dihydroimidazo[4,5-d]pyrrolo[2,3-b]pyridine-7-carboxamide The title compound was prepared using a method analogous to that used to prepare example 103.

MS (ESI) m/z 574.4 (M+H).

$^1$H NMR (500 MHz, CDCl$_3$) δ: 8.30 (br. S., 1H), 7.72 (s, 1H), 7.21 (s, 1H), 6.86 (s, 1H), 4.62 (q, J=6.9 Hz, 2H), 4.21-4.28 (m, 2H), 4.07-4.20 (m, 2H), 4.01 (s, 3H), 3.61 (br. s, 2H), 2.91 (br. s, 1H), 2.79-2.85 (m, 2H), 2.60 (br. S. 1H), 1.47 (t, J=7.2 Hz, 3H), 1.45 (t, J=7.2 Hz, 3H), 1.07-1.36 (m, 6H), 0.81-0.88 (m, 4H), 0.72-0.78 (m, 4H)

Example 112

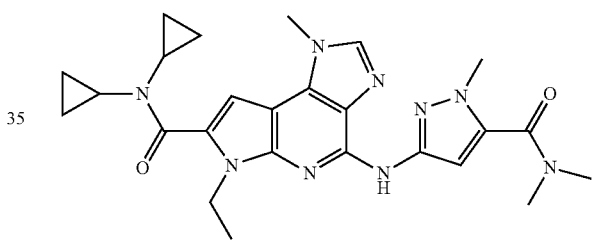

N,N-dicyclopropyl-4-(5-(dimethylcarbamoyl)-1-methyl-1H-pyrazol-3-ylamino)-6-ethyl-1-methyl-1,6-dihydroimidazo[4,5-d]pyrrolo[2,3-b]pyridine-7-carboxamide 112A Preparation of (Z)-tert-butyl 2-(1-(7-(dicyclopropylcarbamoyl)-6-ethyl-1-methyl-1,6-dihydroimidazo[4,5-d]pyrrolo[2,3-b]pyridin-4-ylamino)-4,4-dimethoxy-3-oxobut-1-enyl)-1-methylhydrazinecarboxylate

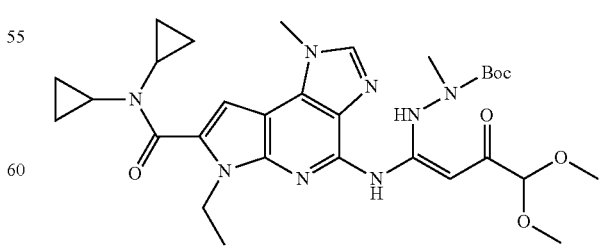

The title compound was prepared using a method analogous to that used to prepare example 101B.

MS (ESI) m/z 611.7 (M+H).

112B Preparation of N,N-dicyclopropyl-6-ethyl-4-(5-formyl-1-methyl-1H-pyrazol-3-ylamino)-1-methyl-1,6-dihydroimidazo[4,5-d]pyrrolo[2,3-b]pyridine-7-carboxamide

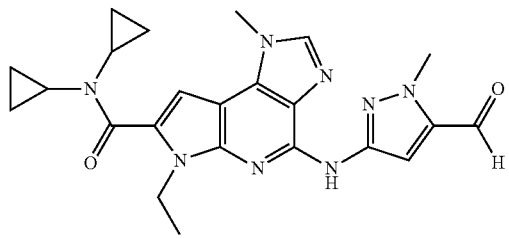 [SMILES: CCn1c(C(=O)N(C2CC2)C2CC2)cc2c3c(ncn3C)c(Nc3cc(C=O)n(C)n3)nc21]

The title compound was prepared using a method analogous to that used to prepare Example 101C.
MS (ESI) m/z 447.3 (M+H).

112C Preparation of 3-(7-(dicyclopropylcarbamoyl)-6-ethyl-1-methyl-1,6-dihydroimidazo[4,5-d]pyrrolo[2,3-b]pyridin-4-ylamino)-1-methyl-1H-pyrazole-5-carboxylic acid

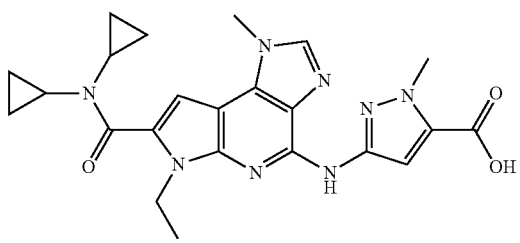 [SMILES: CCn1c(C(=O)N(C2CC2)C2CC2)cc2c3c(ncn3C)c(Nc3cc(C(=O)O)n(C)n3)nc21]

The title compound was prepared using a method analogous to that used to prepare example 101.
MS (ESI) m/z 463.3 (M+H).

112 Preparation of N,N-dicyclopropyl-4-(5-(dimethylcarbamoyl)-1-methyl-1H-pyrazol-3-ylamino)-6-ethyl-1-methyl-1,6-dihydroimidazo[4,5-d]pyrrolo[2,3-b]pyridine-7-carboxamide A mixture of 3-(7-(dicyclopropylcarbamoyl)-6-ethyl-1-methyl-1,6-dihydroimidazo[4,5-d]pyrrolo[2,3-b]pyridin-4-ylamino)-1-methyl-1H-pyrazole-5-carboxylic acid (39.8 mg, 0.086 mmol), HATU (49.0 mg, 0.129 mmol) and dimethylamine, 2M in THF (0.086 mL, 0.172 mmol) in DMF (2 mL) was stirred at room temperature for 2 h. Water was added and the reaction mixture was extracted with ethyl acetate 3 times. The combined organic layers were washed twice with 10% lithium chloride, dried over magnesium sulfate, filtered and concentrated in vacuo. The crude was purified by preparative HPLC to give N,N-dicyclopropyl-4-(5-(dimethylcarbamoyl)-1-methyl-1H-pyrazol-3-ylamino)-6-ethyl-1-methyl-1,6-dihydroimidazo[4,5-d]pyrrolo[2,3-b]pyridine-7-carboxamide (23 mg, 54.1% yield) as an off-white solid.
MS (ESI) m/z 490.2 (M+H).
$^1$H NMR (400 MHz, CDCl$_3$) δ: 8.28 (s, 1H), 7.67 (s, 1H), 7.34 (s, 1H), 6.86 (s, 1H), 4.61 (q, J=7.0 Hz, 2H), 4.01 (s, 3H), 3.95 (s, 3H), 3.29 (s, 3H), 3.16 (s, 3H), 2.79-2.86 (m, 2H), 1.47 (t, J=7.0 Hz, 3H), 0.82-0.89 (m, 4H), 0.72-0.79 (m, 4H).

Example 113

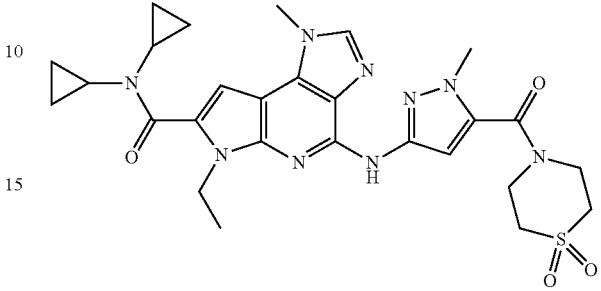

N,N-dicyclopropyl-6-ethyl-4-(1-methyl-5-(thiomorpholine 1,1-dioxide-4-carbonyl)-1H-pyrazol-3-ylamino)-1-methyl-1,6-dihydroimidazo[4,5-d]pyrrolo[2,3-b]pyridine-7-carboxamide The title compound was prepared using a method analogous to that used to prepare example 112.
MS (ESI) m/z 580.3 (M+H).
$^1$H NMR (400 MHz, CDCl$_3$) δ: 8.29 (s., 1H), 7.69 (s, 1H), 7.30 (s, 1H), 6.83 (s, 1H), 4.57 (q, J=6.8 Hz, 2H), 4.31 (br. s., 4H), 4.00 (s, 3H), 3.93 (s, 3H), 3.15 (br. s., 4H), 2.77-2.88 (m, 2H), 1.45 (t, J=7.0 Hz, 3H), 0.80-0.91 (m, 4H), 0.69-0.80 (m, 4H).

Example 114

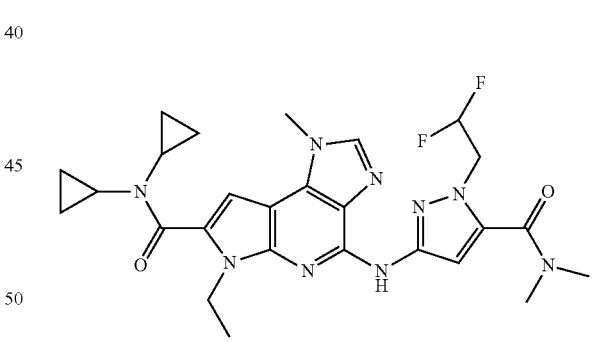

N,N-dicyclopropyl-4-(1-(2,2-difluoroethyl)-5-(dimethylcarbamoyl)-1H-pyrazol-3-ylamino)-6-ethyl-1-methyl-1,6-dihydroimidazo[4,5-d]pyrrolo[2,3-b]pyridine-7-carboxamide The title compound was prepared using a method analogous to that used to prepare Example 112; except utilizing example 80A.
MS (ESI) m/z 540.4 (M+H).
$^1$H NMR (400 MHz, CHLOROFORM-d) δ: 8.41 (br. s., 1H), 7.73 (s, 1H), 7.43 (s, 1H), 6.86 (s, 1H), 6.17 (tt, J=55.9, 4.2 Hz, 1H), 4.57-4.72 (m, 4H), 4.01 (s, 3H), 3.30 (s, 3H), 3.16 (s, 3H), 2.78-2.86 (m, 2H), 1.47 (t, J=7.0 Hz, 3H), 0.80-0.89 (m, 4H), 0.71-0.80 (m, 4H).

Example 115

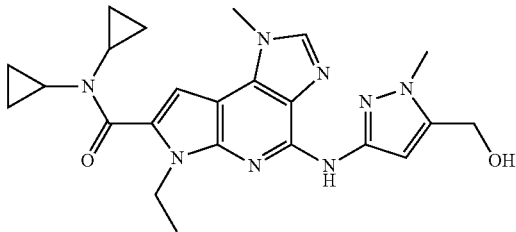 [SMILES: CCn1c(C(=O)N(C2CC2)C2CC2)cc2c3c(ncn3C)c(Nc3cc(CO)n(C)n3)nc21]

N,N-dicyclopropyl-6-ethyl-4-(5-(hydroxymethyl)-1-methyl-1H-pyrazol-3-ylamino)-1-methyl-1,6-dihydroimidazo[4,5-d]pyrrolo[2,3-b]pyridine-7-carboxamide Title compound was prepared by a method similar to that used for example 102.

MS (ESI) m/z 449.3 (M+H)

1H NMR (CDCl$_3$) δ ppm 8.11 (br s, 1H), 7.67 (s, 1H), 7.16 (s, 1H), 6.88 (s, 1H), 4.75 (d, 2H, J=5.94 Hz), 4.67 (q, 2H, J=7.26 Hz), 4.03 (s, 3H), 3.89 (s, 3H), 2.84 (m, 2H), 1.68 (t, 3H, J=6.16 Hz), 1.50 (t, 3H, J=7.15 Hz), 0.75-0.89 (m, 8H)

Example 116

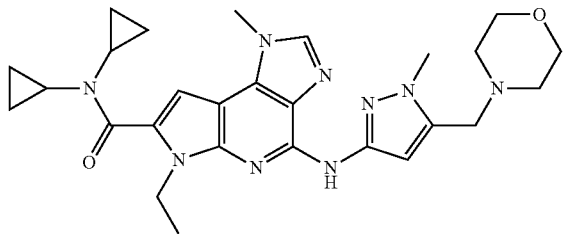 [SMILES: CCn1c(C(=O)N(C2CC2)C2CC2)cc2c3c(ncn3C)c(Nc3cc(CN4CCOCC4)n(C)n3)nc21]

N,N-dicyclopropyl-6-ethyl-1-methyl-4-(1-methyl-5-(morpholinomethyl)-1H-pyrazol-3-ylamino)-1,6-dihydroimidazo[4,5-d]pyrrolo[2,3-b]pyridine-7-carboxamide To a stirred solution of N,N-dicyclopropyl-6-ethyl-4-(5-formyl-1-methyl-1H-pyrazol-3-ylamino)-1-methyl-1,6-dihydroimidazo[4,5-d]pyrrolo[2,3-b]pyridine-7-carboxamide (example 112B, 22 mg, 0.049 mmol) and molecular seives 4 Å (30 mg) in MeOH (2 mL) was added morpholine (0.017 mL, 0.197 mmol). After the solution was stirred at room temperature for 12 hrs, sodium borohydride (7.46 mg, 0.197 mmol) was then added and stirred for 3 hrs. The solution was brought to pH=4 with 1N HCl, neutralized with saturated aqueous sodium bicarbonate, and then extracted with CH$_2$Cl$_2$. The organic layer was dried over anhydrous magnesium sulfate and concentrated in vacuo. The residue was purified by silica-gel flash chromatography using an Isco 40 g column eluting from 0-10% MeOH/CH$_2$Cl$_2$ to yield N,N-dicyclopropyl-6-ethyl-1-methyl-4-(1-methyl-5-(morpholinomethyl)-1H-pyrazol-3-ylamino)-1,6-dihydroimidazo[4,5-d]pyrrolo[2,3-b]pyridine-7-carboxamide (14.3 mg, 0.027 mmol, 54.9% yield) as a white solid.

MS (ESI) m/z 518.3 (M+H)

1H NMR (CDCl$_3$) δ ppm 7.99 (br s, 1 H), 7.57 (s, 1 H), 6.99 (s, 1 H), 6.78 (s, 1H), 4.56 (q, 2 H J=7.04 Hz), 3.93 (s, 3H), 3.77 (s, 3H), 3.64 (m, 4H), 3.48 (s, 2H), 2.75 (m, 2H), 2.45 (m, 4H), 1.42 (t, 3H J=7.02 Hz), 0.66-0.80 (m, 8H)

Example 117

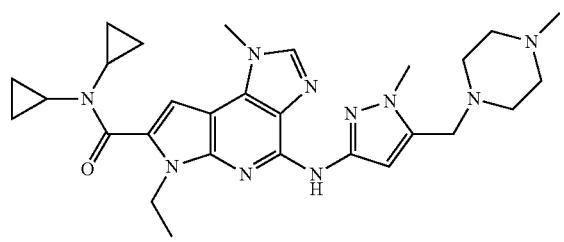 [SMILES: CCn1c(C(=O)N(C2CC2)C2CC2)cc2c3c(ncn3C)c(Nc3cc(CN4CCN(C)CC4)n(C)n3)nc21]

N,N-dicyclopropyl-6-ethyl-1-methyl-4-(1-methyl-5-((4-methylpiperazin-1-yl)methyl)-1H-pyrazol-3-ylamino)-1,6-dihydroimidazo[4,5-d]pyrrolo[2,3-b]pyridine-7-carboxamide Synthesized using a method analogous to that used to prepare example 116.

MS (ESI) m/z 531.4 (M+H)

1H NMR (CDCl$_3$) δ ppm 8.05 (br s, 1 H), 7.60 (s, 1 H), 7.01 (s, 1H), 6.78 (s, 1 H), 4.56 (q, 2 H J=6.75 Hz), 3.95 (s, 3H), 3.72 (s, 3H), 3.61 (s, 2H), 2.96 (m, 4H), 2.76 (m, 4H), 2.74 (m, 2H), 2.71 (s, 3H), 1.42 (t, 3H, J=7.04 Hz), 0.67-0.80 (m, 8H)

Example 118

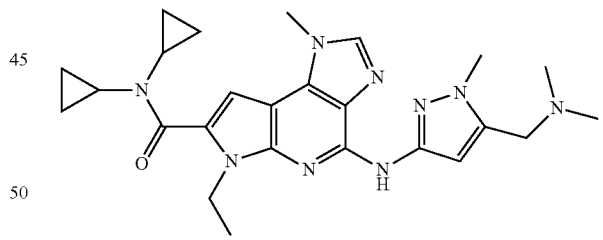

N,N-dicyclopropyl-4-(5-((dimethylamino)methyl)-1-methyl-1H-pyrazol-3-ylamino)-6-ethyl-1-methyl-1,6-dihydroimidazo[4,5-d]pyrrolo[2,3-b]pyridine-7-carboxamide Synthesized using a method analogous to that used to prepare example 116.

MS (ESI) m/z 476.4 (M+H)

1H NMR (CDCl$_3$) δ ppm 7.45 (s, 1 H), 7.33 (s, 1H), 6.84 (s, 1 H), 4.52 (q, 2H, J=7.04 Hz), 4.25 (s, 2H), 3.98 (s, 3H), 3.90 (s, 3H), 2.80 (s, 6H), 2.77 (m, 2H), 1.37 (t, 3H, J=6.82 Hz), 0.64-0.87 (m, 8H)

Example 119

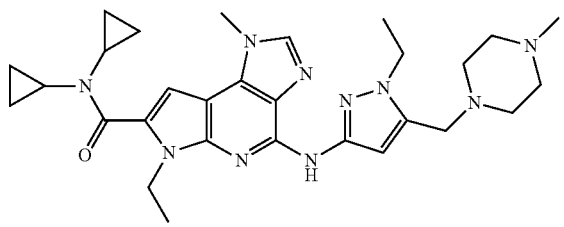 [SMILES: CCn1nc(Nc2nc3c(cc(C(=O)N(C4CC4)C4CC4)n3CC)c3c2ncn3C)cc1CN1CCN(C)CC1]

N,N-dicyclopropyl-6-ethyl-4-(1-ethyl-5-((4-methylpiperazin-1-yl)methyl)-1H-pyrazol-3-ylamino)-1-methyl-1,6-dihydroimidazo[4,5-d]pyrrolo[2,3-b]pyridine-7-carboxamide Prepared using intermediate 101B and procedure as used for example 116.

MS (ESI) m/z 545.4 (M+H)

1H NMR (CDCl$_3$) δ ppm 8.03 (s, 1 H), 7.57 (s, 1 H), 7.00 (s, 1H), 6.78 (s, 1 H), 4.55 (q, 2 H, J=7.04 Hz), 4.03 (q, 2H, J=5.72 Hz), 3.94 (s, 3H), 3.60 (s, 2H), 2.93 (br s, 3H), 2.63-2.84 (br m, 10H), 1.42 (t, 3H, J=7.04 Hz), 1.35 (t. 3H, J=7.26 Hz), 0.69-0.79 (m, 8H)

Example 120

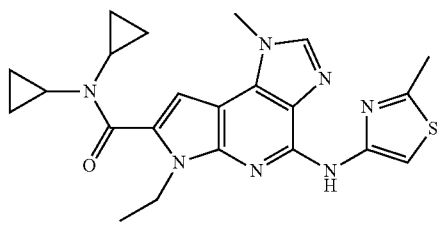 [SMILES: CCn1c(C(=O)N(C2CC2)C2CC2)cc2c3c(ncn3C)c(Nc3csc(C)n3)nc21]

N,N-dicyclopropyl-6-ethyl-1-methyl-4-(2-methylthiazol-4-ylamino)-1,6-dihydroimidazo[4,5-d]pyrrolo[2,3-b]pyridine-7-carboxamide

120A Preparation of 4-(2-chloroacetamido)-N,N-dicyclopropyl-6-ethyl-1-methyl-1,6-dihydroimidazo[4,5-d]pyrrolo[2,3-b]pyridine-7-carboxamide

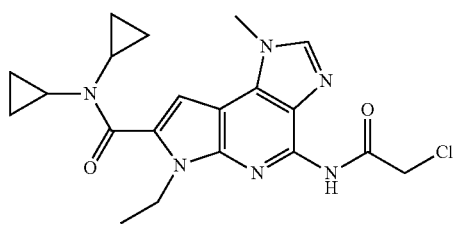 [SMILES: CCn1c(C(=O)N(C2CC2)C2CC2)cc2c3c(ncn3C)c(NC(=O)CCl)nc21]

To a round bottom flask charged with 4-amino-N,N-dicyclopropyl-6-ethyl-1-methyl-1,6-dihydroimidazo[4,5-d]pyrrolo[2,3-b]pyridine-7-carboxamide (example 1J, 47.2 mg, 0.139 mmol) was added dichloromethane (697 µL) and triethylamine (35.0 µL, 0.251 mmol). Chloroacetyl chloride (12.20 µL, 0.153 mmol) was added dropwise. The reaction mixture was stirred at rt for 16 h. Additional chloroacetyl chloride (12.20 µL, 0.153 mmol) was added. The reaction mixture was diluted with dichloromethane. The organics were washed with water, dried over anhydrous sodium sulfate, filtered and concentrated in vacuo. 4-(2-Chloroacetamido)-N,N-dicyclopropyl-6-ethyl-1-methyl-1,6-dihydroimidazo[4,5-d]pyrrolo[2,3-b]pyridine-7-carboxamide (58.5 mg, 101% yield) was isolated as an orange paste. Material was used in subsequent reactions with no further purification.

MS (ESI) m/z 415.0 (M+H)

1H NMR (400 MHz, CHLOROFORM-d) δ ppm 8.04 (br s, 1H), 6.90 (s, 1H), 5.31 (s, 2H), 4.62 (q, 2H, J=7.11 Hz), 4.24 (s, 3H), 2.77-2.88 (m, 2H), 1.47 (t, 3H, J=7.03 Hz), 0.83-0.92 (m, 4H), 0.71-0.80 (m, 4H)

120 Preparation of N,N-dicyclopropyl-6-ethyl-1-methyl-4-(2-methylthiazol-4-ylamino)-1,6-dihydroimidazo[4,5-d]pyrrolo[2,3-b]pyridine-7-carboxamide To a solution of 4-(2-chloroacetamido)-N,N-dicyclopropyl-6-ethyl-1-methyl-1,6-dihydroimidazo[4,5-d]pyrrolo[2,3-b]pyridine-7-carboxamide (58.5 mg, 0.141 mmol) in DMF (176 µL) was added thioacetamide (12.71 mg, 0.169 mmol). The vial was capped and the reaction mixture was heated at 80° C. 3 h. The reaction mixture was concentrated in vacuo. The crude residue was taken up in MeOH and purified by prep-HPLC. N,N-Dicyclopropyl-6-ethyl-1-methyl-4-(2-methylthiazol-4-ylamino)-1,6-dihydroimidazo[4,5-d]pyrrolo[2,3-b]pyridine-7-carboxamide (4.05 mg, 6.6% yield) was isolated as an off-white solid.

MS (ESI) m/z 436.0 (M+H)

1H NMR (400 MHz, DMSO-d$_6$) δ ppm 8.78 (s, 1H), 8.08 (s, 1H), 7.74 (s, 1H), 7.20 (s, 1H), 4.55 (q, 2H, J=7.19 Hz), 4.03 (s, 3H), 2.87-2.98 (m, 2H), 2.65 (s, 3H), 1.34 (t, 3H, J=7.03 Hz), 0.73-0.81 (m, 4H), 0.62-0.69 (m, 4H)

Example 121

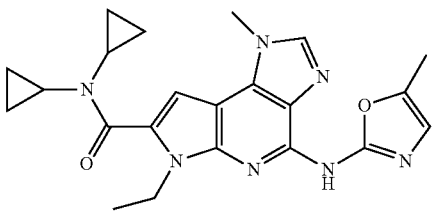 [SMILES: CCn1c(C(=O)N(C2CC2)C2CC2)cc2c3c(ncn3C)c(Nc3ncc(C)o3)nc21]

N,N-dicyclopropyl-6-ethyl-1-methyl-4-(5-methyloxazol-2-ylamino)-1,6-dihydroimidazo[4,5-d]pyrrolo[2,3-b]pyridine-7-carboxamide

121A Preparation of 1-azidopropan-2-one

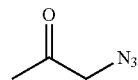

To a solution of chloroacetone (0.680 mL, 8.53 mmol) in acetone (10 mL) and water (5.00 mL) was added sodium azide (0.555 g, 8.53 mmol). The reaction mixture was stirred at rt 3.5 h. The reaction mixture was concentrated under reduced pressure. The remaining aqueous solution was extracted with dichloromethane (2×). The combined organics were washed with brine, dried over anhydrous sodium sulfate, filtered and concentrated in vacuo to yield 1-azidopropan-2-one (0.641 g, 6.47 mmol, 76% yield) as a brown oil. This material was used without any purification.

1H NMR (400 MHz, CHLOROFORM-d) δ ppm 3.96 (s, 2H), 2.21 (s, 3H)

121B Preparation of N,N-dicyclopropyl-6-ethyl-4-isothiocyanato-1-methyl-1,6-dihydroimidazo[4,5-d]pyrrolo[2,3-b]pyridine-7-carboxamide

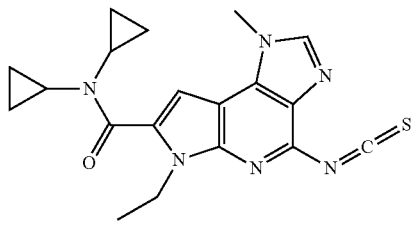 [SMILES: CCn1c(C(=O)N(C2CC2)C2CC2)cc2c3c(ncn3C)c(N=C=S)nc21]

To a mixture of 4-amino-N,N-dicyclopropyl-6-ethyl-1-methyl-1,6-dihydroimidazo[4,5-d]pyrrolo[2,3-b]pyridine-7-carboxamide (example 1J, 194.5 mg, 0.575 mmol) in dichloromethane (2874 µL) in a round bottom flask under nitrogen was added 1,1'-thiocarbonyldi-2(1H)-pyridone (133 mg, 0.575 mmol). The reaction mixture was stirred at rt for 16 h. The reaction mixture was concentrated under reduced pressure. N,N-Dicyclopropyl-6-ethyl-4-isothiocyanato-1-methyl-1,6-dihydroimidazo[4,5-d]pyrrolo[2,3-b]pyridine-7-carboxamide (180 mg, 94% yield) was isolated as a yellow sticky solid. The material was used as is in subsequent reactions.

MS (ESI) m/z 381.1 (M+H)

121 Preparation of N,N-dicyclopropyl-6-ethyl-1-methyl-4-(5-methyloxazol-2-ylamino)-1,6-dihydroimidazo[4,5-d]pyrrolo[2,3-b]pyridine-7-carboxamide To a solution of N,N-dicyclopropyl-6-ethyl-4-isothiocyanato-1-methyl-1,6-dihydroimidazo[4,5-d]pyrrolo[2,3-b]pyridine-7-carboxamide (example 121B, 45.7 mg, 0.120 mmol) in dioxane (343 µL) was added 1-azidopropan-2-one (14.28 mg, 0.144 mmol) and triphenylphosphine (37.8 mg, 0.144 mmol). The contents of the flask were immersed into a preheated oil bath for 35 min and cooled to room temperature. The residue was diluted with ethyl acetate and quenched with saturated aqueous sodium bicarbonate. The aqueous layer was extracted with ethyl acetate. The combined organics were washed with brine, dried over anhydrous sodium sulfate, filtered and concentrated in vacuo. The crude residue was purified by flash chromatography on an Isco 12 g column eluting with 1-10% MeOH/CH₂Cl₂. The pale yellow solid was taken up in MeOH and further purified by preparative HPLC. N,N-Dicyclopropyl-6-ethyl-1-methyl-4-(5-methyloxazol-2-ylamino)-1,6-dihydro imidazo[4,5-d]pyrrolo[2,3-b]pyridine-7-carboxamide was isolated (10 mg, 25% yield) as a white solid.

MS (ESI) m/z 420.0 (M+H)

1H NMR (400 MHz, DMSO-d₆) δ ppm 9.86 (s, 1H), 8.05 (s, 1H), 7.18 (s, 1H), 6.66 (d, 1H, J=1.51 Hz), 4.41 (q, 2H, J=7.28 Hz), 4.02 (s, 3H), 2.85-2.98 (m, 2H), 2.21-2.29 (m, 3H), 1.27 (t, 3H, J=7.15 Hz), 0.71-0.80 (m, 4H), 0.60-0.70 (m, 4H)

Example 122

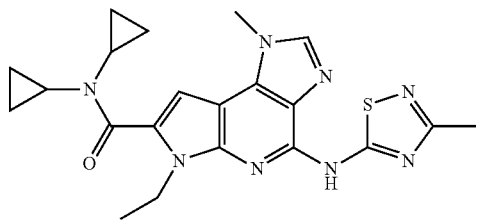 [SMILES: CCn1c(C(=O)N(C2CC2)C2CC2)cc2c3c(ncn3C)c(Nc3nc(C)ns3)nc21]

N,N-dicyclopropyl-6-ethyl-1-methyl-4-(3-methyl-1,2,4-thiadiazol-5-ylamino)-1,6-dihydroimidazo[4,5-d]pyrrolo[2,3-b]pyridine-7-carboxamide A mixture of N,N-dicyclopropyl-6-ethyl-4-isothiocyanato-1-methyl-1,6-dihydroimidazo[4,5-d]pyrrolo[2,3-b]pyridine-7-carboxamide (example 121B, 0.042 g, 0.111 mmol), acetamidine hydrochloride (10.49 mg, 0.111 mmol), and Hünig's Base (0.058 mL, 0.333 mmol) in DMF (0.617 mL) was stirred at rt ON. Diethyl azodicarboxylate (0.088 mL, 0.222 mmol) was added and stirring continued at room temperature for 16 h. The reaction mixture was concentrated. The residue was taken up in MeOH and purified by preparative HPLC. N,N-Dicyclopropyl-6-ethyl-1-methyl-4-(3-methyl-1,2,4-thiadiazol-5-ylamino)-1,6-dihydroimidazo[4,5-d]pyrrolo[2,3-b]pyridine-7-carboxamide (4.32 mg, 9% yield) was isolated as a pale yellow solid.

MS (ESI) m/z 437.1 (M+H)

1H NMR (400 MHz, MeOD) δ ppm 8.10 (s, 1 H), 7.28 (s, 1 H), 4.73 (q, 2 H, J=7.19 Hz), 4.13 (s, 3 H), 2.93-3.01 (m, 2 H), 2.53 (s, 3 H), 1.53 (t, 3 H, J=7.03 Hz), 0.83-0.92 (m, 4 H), 0.76-0.83 (m, 4 H)

Example 123

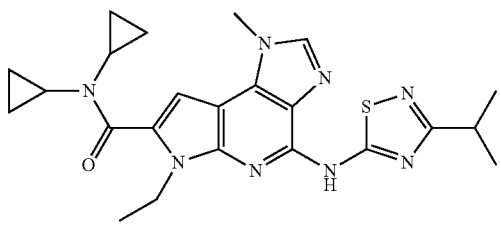 [SMILES: CCn1c(C(=O)N(C2CC2)C2CC2)cc2c3c(ncn3C)c(Nc3nc(C(C)C)ns3)nc21]

Preparation of N,N-dicyclopropyl-6-ethyl-4-(3-isopropyl-1,2,4-thiadiazol-5-ylamino)-1-methyl-1,6-dihydroimidazo[4,5-d]pyrrolo[2,3-b]pyridine-7-carboxamide This compound was prepared according to example 122 using isobutyrimidamide hydrochloride (15.08 mg, 0.123 mmol) and disopropyl azodicarboxylate (47.8 µL, 0.246 mmol). N,N-Dicyclopropyl-6-ethyl-4-(3-isopropyl-1,2,4-thiadiazol-5-ylamino)-1-methyl-1,6-dihydroimidazo[4,5-d]

pyrrolo[2,3-b]pyridine-7-carboxamide (21 mg, 34.9% yield) was isolated as an off-white solid.

MS (ESI) m/z 465.3 (M+H)

1H NMR (400 MHz, DMSO-d$_6$) δ ppm 12.24 (s, 1H), 8.18 (s, 1H), 7.28 (s, 1H), 4.64 (q, 2H, J=6.94 Hz), 4.06 (s, 3H), 3.10 (ddd, 1H, J=13.93, 6.90, 6.78 Hz), 2.86-3.00 (m, 2H), 1.42 (t, 3H, J=7.03 Hz), 1.32 (s, 3H), 1.31 (s, 3H), 0.72-0.81 (m, 4H), 0.63-0.71 (m, 4H)

Example 124

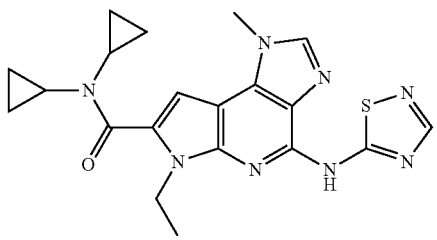 [SMILES: CCn1c(C(=O)N(C2CC2)C2CC2)cc2c3c(ncn3C)c(Nc3ncns3)nc21]

4-(1,2,4-thiadiazol-5-ylamino)-N,N-dicyclopropyl-6-ethyl-1-methyl-1,6-dihydroimidazo[4,5-d]pyrrolo[2,3-b]pyridine-7-carboxamide A mixture of N,N-dicyclopropyl-6-ethyl-1-methyl-4-thioureido-1,6-dihydroimidazo[4,5-d]pyrrolo[2,3-b]pyridine-7-carboxamide (example 2B, 30 mg, 0.075 mmol) and 1,1-dimethoxy-N,N-dimethylmethanamine (1 g, 8.39 mmol) was heated at 50° C. for 2 h. Excess 1,1-dimethoxy-N,N-dimethylmethanamine was evaporated in vacuo and the crude example was dissolved in dichloromethane (1 mL) and O-(mesitylsulfonyl)hydroxylamine (24.4 mg, 0.113 mmol) was added. The reaction mixture was stirred at room temperature for 3 h. Water was added and the layers were separated. The organic layer was dried over magnesium sulfate, filtered and concentrated in vacuo. The crude residue was purified by preparative HPLC to give 4-(1,2,4-thiadiazol-5-ylamino)-N,N-dicyclopropyl-6-ethyl-1-methyl-1,6-dihydroimidazo[4,5-d]pyrrolo[2,3-b]pyridine-7-carboxamide (7 mg, 19.20% yield) as a yellow solid.

MS (ESI) m/z 423.0 (M+H).

¹H NMR (500 MHz, CD$_3$OD) δ: 8.32 (s, 1H), 8.27 (s, 1H), 7.38 (d, J=4.4 Hz, 1H), 7.28 (s, 1H), 4.74 (q, J=7.0 Hz, 2H), 4.15 (s, 3H), 2.94-3.00 (m, 2H), 1.53 (t, J=7.0 Hz, 3H), 0.82-0.89 (m, 4H), 0.75-0.82 (m, 4H)

Example 125

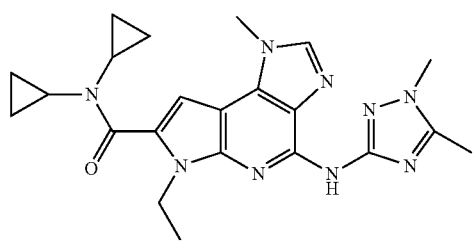 [SMILES: CCn1c(C(=O)N(C2CC2)C2CC2)cc2c3c(ncn3C)c(Nc3nc(C)n(C)n3)nc21]

N,N-dicyclopropyl-4-(1,5-dimethyl-1H-1,2,4-triazol-3-ylamino)-6-ethyl-1-methyl-1,6-dihydroimidazo[4,5-d]pyrrolo[2,3-b]pyridine-7-carboxamide 125A Preparation of 4-(3-acetylthioureido)-N,N-dicyclopropyl-6-ethyl-1-methyl-1,6-dihydroimidazo[4,5-d]pyrrolo[2,3-b]pyridine-7-carboxamide

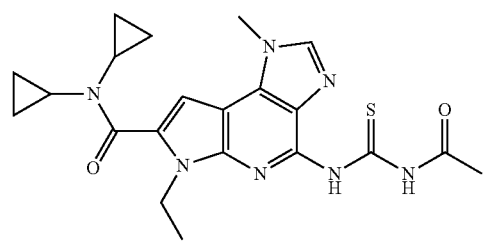 [SMILES: CCn1c(C(=O)N(C2CC2)C2CC2)cc2c3c(ncn3C)c(NC(=S)NC(C)=O)nc21]

To a solution of 4-amino-N,N-dicyclopropyl-6-ethyl-1-methyl-1,6-dihydroimidazo[4,5-d]pyrrolo[2,3-b]pyridine-7-carboxamide (example 1J, 60 mg, 0.177 mmol) in acetone (1.182 mL) was added acetyl isothiocyanate (0.020 mL, 0.230 mmol). The reaction mixture was stirred at room temperature for 6 h. LC/MS showed still half of the starting material left. Another 0.5 equivalent of acetyl isothiocyanate was added and the reaction mixture was heated at 35° C. overnight. Solvent was evaporated and the crude product was purified by flash chromatography on silica gel using an automated ISCO system (24 g column, eluting with 2-8% methanol/dichloromethane). 4-(3-Acetylthioureido)-N,N-dicyclopropyl-6-ethyl-1-methyl-1,6-dihydroimidazo[4,5-d]pyrrolo[2,3-b]pyridine-7-carboxamide (34 mg, 43.6% yield) was obtained as a yellow solid.

MS (ESI) m/z 440.1 (M+H).

125 Preparation of N,N-dicyclopropyl-4-(1,5-dimethyl-1H-1,2,4-triazol-3-ylamino)-6-ethyl-1-methyl-1,6-dihydroimidazo[4,5-d]pyrrolo[2,3-b]pyridine-7-carboxamide A mixture of 4-(3-acetylthioureido)-N,N-dicyclopropyl-6-ethyl-1-methyl-1,6-dihydroimidazo[4,5-d]pyrrolo[2,3-b]pyridine-7-carboxamide (example 125A, 17 mg, 0.039 mmol) and methylhydrazine (2.486 μL, 0.046 mmol) in acetic acid (0.5 mL) was heated at 80° C. for 4 h, LC/MS showed starting material still remaining. Additional methylhydrazine (2.486 μL, 0.046 mmol) was added and heating continued for another 2 h, reaction complete. Solvent was evaporated and the crude was purified by preparative HPLC to furnish N,N-dicyclopropyl-4-(1,5-dimethyl-1H-1,2,4-triazol-3-ylamino)-6-ethyl-1-methyl-1,6-dihydroimidazo[4,5-d]pyrrolo[2,3-b]pyridine-7-carboxamide (5.2 mg, 30.7% yield) as an off-white solid.

MS (ESI) m/z 434.3 (M+H).

¹H NMR (CDCl$_3$) δ: 7.96 (s, 1H), 7.65 (s, 1H), 6.83 (s, 1H), 4.67 (q, J=7.1 Hz, 2H), 4.01 (s, 3H), 3.82 (s, 3H), 2.77-2.84 (m, 2H), 2.43 (s, 3H), 1.48 (t, J=7.2 Hz, 3H), 0.79-0.86 (m, 4H), 0.71-0.77 (m, 4H).

What is claimed is:
1. A method for treating myeloproliferative diseases comprising administering to a mammalian species in need thereof, a therapeutically effective amount of the compound of the formula

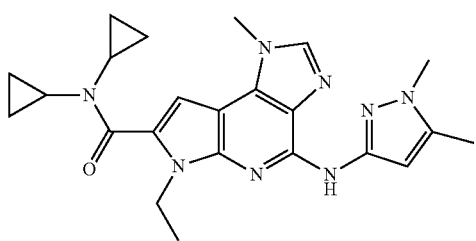 [SMILES: CCn1c(C(=O)N(C2CC2)C2CC2)cc2c3c(ncn3C)c(Nc3cc(C)n(C)n3)nc21]

or a pharmaceutically acceptable salt, tautomer or stereoisomer thereof.

2. The method according to claim 1 wherein the myeloproliferative disease is primary myelofibrosis.

3. The method according to claim 2 further comprising administering to a warm-blooded species in need thereof, a therapeutically effective amount of one or more other anti-cancer or cytotoxic agents in combination with the compound of the formula

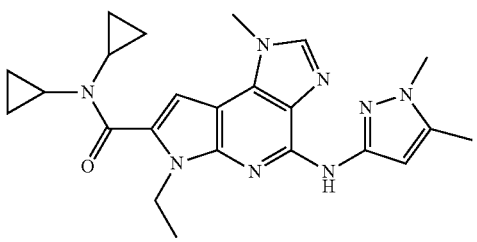 [SMILES: CCn1c(C(=O)N(C2CC2)C2CC2)cc2c3c(ncn3C)c(Nc3cc(C)n(C)n3)nc21]

or a pharmaceutically acceptable salt, tautomer or stereoisomer thereof.

* * * * *